(12) United States Patent
Glick et al.

(10) Patent No.: US 8,673,897 B2
(45) Date of Patent: Mar. 18, 2014

(54) BENZODIAZEPINONE COMPOUNDS AND METHODS OF TREATMENT USING SAME

(75) Inventors: Gary D. Glick, Ann Arbor, MI (US); Alexander Ross Hurd, Ann Arbor, MI (US); Chad Alan Van Huis, Plymouth, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 68 days.

(21) Appl. No.: 13/395,566

(22) PCT Filed: Sep. 17, 2010

(86) PCT No.: PCT/US2010/049282
§ 371 (c)(1),
(2), (4) Date: May 17, 2012

(87) PCT Pub. No.: WO2011/035124
PCT Pub. Date: Mar. 24, 2011

(65) Prior Publication Data
US 2012/0232067 A1    Sep. 13, 2012

Related U.S. Application Data

(60) Provisional application No. 61/243,792, filed on Sep. 18, 2009.

(51) Int. Cl.
*C07D 243/18* (2006.01)
*C07D 243/12* (2006.01)
*A61K 31/55* (2006.01)

(52) U.S. Cl.
USPC .......................................... 514/221; 540/504

(58) Field of Classification Search
USPC .......................................... 540/504; 514/221
See application file for complete search history.

(56) References Cited

U.S. PATENT DOCUMENTS

| | | |
|---|---|---|
| 3,261,828 A | 7/1966 | Uskokovic et al. |
| 3,374,264 A | 3/1968 | Uskokovic |
| 3,384,635 A | 5/1968 | Calabateas et al. |
| 3,415,814 A | 12/1968 | Calabateas et al. |
| 3,847,905 A | 11/1974 | Bub |
| 4,076,823 A | 2/1978 | Wade et al. |
| 4,088,756 A | 5/1978 | Voorhees |
| 4,108,852 A | 8/1978 | Bub |
| 4,110,337 A | 8/1978 | Szarvasi et al. |
| RE30,293 E | 6/1980 | Bub |
| 4,495,101 A | 1/1985 | Klaubert et al. |
| 4,551,480 A | 11/1985 | Stiefel et al. |
| 4,560,684 A | 12/1985 | Sugasawa et al. |
| 4,623,646 A | 11/1986 | Casals-Stenzel |
| 4,751,223 A | 6/1988 | Glamkowski et al. |
| 4,820,834 A | 4/1989 | Evans |
| 4,894,366 A | 1/1990 | Okuhara |
| 4,898,861 A | 2/1990 | Morgan et al. |
| 4,916,138 A | 4/1990 | Ueda |
| 4,929,611 A | 5/1990 | Okuhara |
| 4,946,778 A | 8/1990 | Ladner et al. |
| 5,004,741 A | 4/1991 | Evans |
| 5,041,438 A | 8/1991 | Hsu et al. |
| 5,141,930 A | 8/1992 | Nakao et al. |
| 5,147,872 A | 9/1992 | Golwyn |
| 5,216,148 A | 6/1993 | Klaus et al. |
| 5,288,514 A | 2/1994 | Ellman |
| 5,324,726 A | 6/1994 | Bock et al. |
| 5,391,566 A | 2/1995 | Chakravarty |
| 5,444,092 A | 8/1995 | Collins |
| 5,521,170 A | 5/1996 | Setoi |
| 5,545,568 A | 8/1996 | Ellman |
| 5,559,230 A | 9/1996 | Ogawa et al. |
| 5,591,227 A | 1/1997 | Dinh et al. |
| 5,597,915 A | 1/1997 | Chambers et al. |
| 5,599,352 A | 2/1997 | Dinh et al. |
| 5,633,251 A | 5/1997 | Claremon |
| 5,677,282 A | 10/1997 | Oleksyszyn |
| 5,697,967 A | 12/1997 | Dinh et al. |
| 5,763,437 A | 6/1998 | Sato |
| 5,776,946 A | 7/1998 | McGeer et al. |
| 5,861,380 A | 1/1999 | Gyorkos et al. |
| 5,962,337 A | 10/1999 | Ohlmeyer |
| 6,004,942 A | 12/1999 | Firestein et al. |
| 6,074,859 A | 6/2000 | Hirokawa |
| 6,080,588 A | 6/2000 | Glick et al. |
| 6,100,254 A | 8/2000 | Budde et al. |
| 6,239,131 B1 | 5/2001 | Shinozaki et al. |
| 6,277,844 B1 | 8/2001 | Spector et al. |
| 6,319,931 B1 | 11/2001 | Kroemer et al. |
| 6,506,744 B1 | 1/2003 | Alig |

(Continued)

FOREIGN PATENT DOCUMENTS

| | | |
|---|---|---|
| CA | 2372150 | 11/2000 |
| CA | 2457405 | 2/2003 |

(Continued)

OTHER PUBLICATIONS

Solomko, et al., Chemistry of Heterocyclic Compounds, vol. 11, No. 11, Nov. 1975, pp. 1231-1248.

Algarra, et al., "Application of the Photo-Fries Rearrangement of Aryl N-Chloroacetylanthranylates as Key Step in the . . . ", Heterocycles, vol. 36 1993, pp. 2335-2344.

EP Patent Application No. 06 717616 Supplementary Search Report dated Mar. 26, 2009.

(Continued)

*Primary Examiner* — Bruck Kifle
(74) *Attorney, Agent, or Firm* — Fish & Richardson P.C.

(57) ABSTRACT

The invention provides 1,4-benzodiazepinone compounds, pharmaceutical compositions, and methods of treating autoimmune disorders, chronic inflammatory disorders, and hyperproliferative disorders. For example, the 1,4-benzodiazepinone compounds and pharmaceutical compositions are contemplated to be useful for treating rheumatoid arthritis, graft-versus-host disease, inflammatory bowel disease, and the like.

16 Claims, No Drawings

(56) References Cited

U.S. PATENT DOCUMENTS

| | | | |
|---|---|---|---|
| 6,524,623 | B1 | 2/2003 | Hodosh |
| 6,524,832 | B1 | 2/2003 | Kufe et al. |
| 6,579,854 | B1 | 6/2003 | Mitchell et al. |
| 6,605,593 | B1 | 8/2003 | Naicker |
| 6,613,739 | B1 | 9/2003 | Naicker |
| 6,767,533 | B1 | 7/2004 | Casellas |
| 6,824,561 | B2 | 11/2004 | Soykan et al. |
| 6,916,813 | B2 | 7/2005 | Atwal |
| 7,125,866 | B1 | 10/2006 | Glick |
| 7,144,880 | B2 | 12/2006 | Glick |
| 7,150,433 | B2 | 12/2006 | Healy |
| 7,175,953 | B2 | 2/2007 | Licha |
| 7,220,739 | B2 | 5/2007 | Glick |
| 7,250,410 | B2 | 7/2007 | Bourguignon |
| 7,276,348 | B2 | 10/2007 | Glick |
| 7,351,421 | B2 | 4/2008 | Sung |
| 7,572,788 | B2 | 8/2009 | Glick |
| 7,638,624 | B2 | 12/2009 | Glick |
| 7,683,046 | B2 | 3/2010 | Glick |
| 7,851,465 | B2 | 12/2010 | Glick |
| 2002/0025946 | A1 | 2/2002 | Buchanan et al. |
| 2002/0048566 | A1 | 4/2002 | El-Deiry et al. |
| 2002/0128208 | A1 | 9/2002 | Snyder |
| 2003/0044776 | A1 | 3/2003 | Dykens et al. |
| 2003/0119029 | A1 | 6/2003 | Glick |
| 2004/0009972 | A1 | 1/2004 | Ding |
| 2004/0087489 | A1 | 5/2004 | Ruiz |
| 2004/0157833 | A1 | 8/2004 | Harris |
| 2004/0176358 | A1 | 9/2004 | Glick |
| 2005/0113460 | A1 | 5/2005 | Glick |
| 2005/0261176 | A1 | 11/2005 | Glick |
| 2005/0272723 | A1 | 12/2005 | Glick |
| 2006/0025388 | A1 | 2/2006 | Glick |
| 2006/0052369 | A1 | 3/2006 | Glick |
| 2006/0166975 | A1 | 7/2006 | Glick |
| 2007/0036854 | A1 | 2/2007 | Glick |
| 2007/0043033 | A1 | 2/2007 | Glick |
| 2007/0105844 | A1 | 5/2007 | Glick |
| 2007/0111994 | A1 | 5/2007 | Glick |
| 2007/0135418 | A1 | 6/2007 | Glick |
| 2007/0299059 | A1 | 12/2007 | Glick |
| 2008/0064686 | A1 | 3/2008 | Durrani |
| 2008/0112553 | A1 | 5/2008 | Chen et al. |

FOREIGN PATENT DOCUMENTS

| | | |
|---|---|---|
| CA | 2457405 | 3/2003 |
| DE | 1810423 | 10/1969 |
| EP | 0227539 | 5/1990 |
| EP | 0 349 949 | 10/1990 |
| EP | 0 906 907 | 4/1999 |
| EP | 1143946 | 10/2001 |
| EP | 1423122 | 2/2003 |
| EP | 1398033 | 3/2004 |
| EP | 1622684 | 2/2006 |
| EP | 1742640 | 7/2006 |
| EP | 1778204 | 5/2007 |
| EP | 1786429 | 5/2007 |
| EP | 1845996 | 10/2007 |
| GB | 1363735 | 8/1974 |
| RU | 2096044 | 11/1997 |
| WO | 90/05305 | 5/1990 |
| WO | 90/13332 | 5/1990 |
| WO | 91/12779 | 9/1991 |
| WO | 9201683 | 2/1992 |
| WO | 94/08234 | 4/1994 |
| WO | 97/01560 | 1/1997 |
| WO | 97/30992 | 8/1997 |
| WO | 98/14192 | 4/1998 |
| WO | 98/57161 | 12/1998 |
| WO | 99/19306 | 4/1999 |
| WO | 99/29347 | 6/1999 |
| WO | 99/58117 | 11/1999 |
| WO | 99/66958 | 12/1999 |
| WO | 99/67220 | 12/1999 |
| WO | 00/19200 | 6/2000 |
| WO | 00/66106 | 11/2000 |
| WO | 01/51922 | 7/2001 |
| WO | 02/67988 | 9/2002 |
| WO | 02/098865 | 12/2002 |
| WO | 03/015703 | 2/2003 |
| WO | 03/041658 | 5/2003 |
| WO | 03/045901 | 6/2003 |
| WO | 03/050261 | 6/2003 |
| WO | 03/106628 | 12/2003 |
| WO | 2004/050610 | 6/2004 |
| WO | 2005/004988 | 1/2005 |
| WO | 2006/007532 | 1/2006 |
| WO | 2006014526 | 2/2006 |
| WO | 2006/029245 | 3/2006 |
| WO | 2006002945 | 3/2006 |
| WO | 2006073448 | 7/2006 |
| WO | 2006074358 | 7/2006 |
| WO | 2007050587 | 5/2007 |
| WO | 2007053193 | 5/2007 |
| WO | 2007053725 | 5/2007 |
| WO | 2007146167 | 12/2007 |
| WO | 2008112553 | 9/2008 |
| WO | 2008116156 | 9/2008 |
| WO | 2008/133635 | 11/2008 |
| WO | 2009/036175 | 3/2009 |
| WO | 2009/061916 | 5/2009 |

OTHER PUBLICATIONS

Levitzki, Alexander, "Protein Tyrosine Kinase Inhibitors as Novel Therapeutic Agents," Pharmacol. Ther. vol. 82, Nos. 2-3, pp. 231-239 (1999).

Sanchez, et al., "Tumorigenic activity of the BCR-ABL oncogenes is mediated by BCL2" Proc Natl Acad Sci U S A (Jun. 6, 1995) 92(12) 5287-5291.

Ji Yang, et al., "Prevention of Apoptosis by BCL-2; Release of Cytochrome c from Mitochondria Blocked" Science 275, 1129 (1997).

Prindull, "Apoptosis in the embryo and tumorigenesis" European Journal of Cancer, vol. 31, Issue 1 (1995) pp. 116-123.

Chinese Office Action, CN Patent Application No. 200580029827.4, dated Apr. 17, 2009.

Lowe, "Systemic treatment of severe psoriasis," The New England Journal of Medicine, 324 (5), Feb. 7, 1991, pp. 333-334.

Laupacis, et al., "Cyclosporin A: a powerful immunosuppressant", CMA Journal, May 1, 1982, vol. 126, pp. 1041-1046.

Otto, Michael W., Ph.D., et al., "Benzodiazepine Use, Cognitive Impairment, and Cognitive-Behavioral Therapy for Anxiety Disorders: Issues in the Treatment of a Patient in Need," J. Clin. Psychiatry, 2005, 66 (supp 2).

Yoshi, M., et al., (2005) Nippon Yakurigaku␣asshi 125(1):33-36 (English Abstract attached).

Yasuda, K., (2004) Nippon Rinsho. 62 Suppl. 12:360-363. Abstract not available.

Decaudin, Didier, "Peripheral benzodiazepine receptor and its clinical targeting," Anti-Cancer Drugs, 2004, vol. 15, No. 8.

Bonnot, O., et al., "Exposition in utero au lorazepam et atresie anale: signal epidemiologique," (2003) Encephale. 29(6):553-559.

Lacapere, Jean-Jacques, Vassilios Papadopoulos, "Peripheral-type benzodiazepine receptor: structure and function of a cholesterol-binding protein in steroid and bile acid biosynthesis," Steroids, 68 (2003) 569-585.

Galiegue, S., et al., "The Peripheral Benzodiazepine Receptor: A Promising Therapeutic Drug Target," (2003) Curr. Med. Chem (10(16):1563-1572.

Papadopoulo, V. (2003), Lecture: Peripheral benzodiazepine receptor: structure and function in health and disease, Ann. Pharm. Fr. 61(1):30-50.

Goethals, Ingeborg, et al., "Is central benzodiazepine receptor imaging useful for the identification of epileptogenic foci in localization-related epilepsies?" European Journal of Nuclear Medicine and Molecular Imaging vol. 30, No. 2, Feb. 2003.

Castedo, Marian, et al., "Mitochondrial Apoptosis and the Peripheral Benzodiazepine Receptor: a Novel Target for Viral and Pharmacological Manipulation," The Journal of Experimental Medicine, vol. 196, No. 9, Nov. 4, 2002.

(56) References Cited

OTHER PUBLICATIONS

Buffett-Jerrott S.E. et al., "Cognitive and Sedative Effects of Benzodiazepine Use," Current Pharmaceutical Design, 2002, 8, 45-48.
Smyth, W.F., et al. (1998), "A critical evaluation of the application of capillary electrophoresis to the detection and determination of 1,4-benzodiazepine tranquilizers in formulations and body materials," Electrophoresis 19(16-17):2870-2882.
Yoshii, M., et al. (1998) Nihon Shinkeo Seishin Yakurigaku Zasshi, 18(2):49-54.
Varani, et al., (1994), "All-trans Retinoic Acid (RA) Stimulates Events in Organ-cultured Human Skin that Underlie Repair," J. Clin. Invest., 94:1747-1753.
Griffith, C.E., "Editorial Comment: Ascomycin: an advance in the management of atopic dermatitis," Br. J. Dermatol., Apr. 2001; 144(4):679-81.
Stern, R.S. (1995), "Epidemiology of Psoriasis," Dermatologic Clinics, 13:717-722.
Fry, L (1988), "Psoriasis," Brit. J. Dermatol., 119:445-461.
Krueger GC, et al., (1984), "Psoriasis," J. Am. Acad. Dermatol., 11:937-947.
Varani, J., et al. (2001), "Heparin-Binding Epidermal-Growth-Factor-Like Growth Factor Activation of Keratinocyte ErbB . . . ", J. Invest. Dermatol., 117:1335-1341.
Varani, J., et al., "A Novel Benzodiazepine Selectively Inhibits Keratinocyte Proliferation . . . ", The Journal of Pharmacology and Experimental Therapeutics, 2005, vol. 313, No. 1, pp. 56-63.
International Search Report and Written Opinion, PCT/US2008/082629, mailed Jun. 1, 2009.
Bhagavathula, Narasimharao, et al., "7-Chloro-t-(4-hydroxyphenyl_-1-methyl-3-(naphthalen-2-ylmethyl) . . . ", J. Pharmacol & Exp Ther 324: 938-947 (2008).
Borea, "Stereochemical Features Controlling Binding and Intrinsic Activity Properties of Benzodiazepine Receptor Ligands", Molecular Pharmacology, Apr. 1987, 31 (4), pp. 334-344, p. 344, Abstract.
Mahrle, et al., Br. J. Bermatol. 1974, 91, 529-540.
Mui et al. Br. J. Dermatol. 1975, 92, 255-262.
EP Search Report dated Nov. 26, 2009, EP Patent Application No. 09003224.4.
Nadin, Alan, et al., "New Synthesis of 1,3-Dihydro-1,4-benzodiazepin-2(2H)-ones and 3-Amino-1,3-dihydro-1,4-benzodiazepin-2(2H)-ones: Pd-Catalyzed Cross-Coupling of Imidoyl Chlorides with Organoboronic Acids," J. Org. Chem., 2003, 68, pp. 2844-2852.
Reddy, Pavan, et al., "Interleukin-18 Regulates Acute Graft-Versus-Host Disease by Enhancing Fas-mediated Donor T Cell Apoptosis," J. Exp. Med., 2001, 194: 1433-1440.
Bossu, et al., "IL-18 cDNA vaccination protects mice from spontaneous lupus-like autoimmune disease," PNAS 2003, 100: 14181-14186.
De Bandt, et al., "Systemic lupus erythematosus induced by anti-tumour necrosis factor alpha therapy: a French national survey," Arthritis Res. & Ther., 2005, 7: R545-R551.
Abunasser, et al., "Etanercept-Induced Lupus Erythematosus Presenting as a Unilateral Pleural Effusion," Chest 2008, 134: 850-853.
Busca, et al., "Recombinant human soluble tumor necrosis factor receptor fusion protein as treatment for steroid refractory graft-versus-host disease following allogeneic hematopoietic stem cell transplatation," Am. J. Hematol., 2007, 82: 45-52.
Kyungjin, Kim, Steven K. Volkkan, and Jonathan A. Ellman, Synthesis of 3-Substituted 1,4-Benzodiazepin-2-ones, J. Braz. Chem. Soc. vol. 9(4), 375-379 (1998).
Kluge, et al., "Kinetics of Inactivation of the F1F0 ATPase of Propionigenium modestum by Dicyclohexylcarbodiimide in Relationship to H+ and Na+ Concentration: Probing the Binding Site for the Coupling Ions," Biochemistry 1993, 32, 10378-10386.
Covelli, Vito, "Stress, Neuropsychiatric Disorders and Immunological Effects Exerted by Benzodiazepines," Immunopharmacology and Immunotoxicology, 20(2), 199-209 (1998).
EP Search Report dated Jun. 23, 2010, EP Patent Application No. 10 003 823.1.
EP Search Report dated Aug. 10, 2010, EP Patent Application No. 08731682.4.
Office Action Mailed Apr. 3, 2009, U.S. Appl. No. 11/176,719, filed Jul. 6, 2005.
Office Action Mailed Aug. 19, 2009, U.S. Appl. No. 11/176,719, filed Jul. 6, 2005.
Office Action Mailed May 24, 2010, U.S. Appl. No. 11/176,719, filed Jul. 6, 2005.
Bisaha, S.N., et al., A switch in enantiomer preference between mitochondrial F1F0-ATPase chemotypes, Bioorganic & Medicinal Chemistry Letters, 2005 15(11), pp. 2749-2751.
International Search Report and Written Opinion dated Mar. 27, 2009, PCT/US2008/076021.
Adachi, M., et al., "Aberrant Transcription Caused by the Insertion an Early Transposable Element . . . ," PNAS. USA-90:1756-1760 (1993).
Adelman, N.E., et al., Treatment of (NZB X NZW)F1 Disease with Anti-I—A Monoclonal Antibodies; J. Exp. Med.—158:1350.1355 (1983).
Appleby, et al., "Murine chronic graft-versus-host disease as a model of osystemic lupus erythematosus: effect of immunosuppressive drugs on disease development," Clin. Exp. Immunol. (1989) 78, 449-453.
Atwal, K.S., et al., "N-(1-Aryl-2-(1-imidazolo)ethyl)-guanidine derivates as potent inhibitors of the bovine mitochondrial F140 ATP hydrolase" Bioorganic & Medicinal Chem. Ltr., vol. 14, pp. 1021-1030 (2004).
Atwal, K.S., et al., "Small Molecule Mitochondrial F1F0 ATPase Huydrolase Inhibitors as Cardioprotective Agents" J. Med. Chem. 47, pp. 1081-1084 (2004).
Baader, S.L., et al., Uptake and Cytotoxicity of Ascorbic Acid and Dehydroascorbic Acid . . . Anticancer Research—14:221-228 (1994).
Bastian, et al., "Casein Interference in Bovine Plasmin Assays Using a Synthetic Substrate," (1991) J Dairy Sci 74:4119-4124.
Beale, P.J., et al., "BCL-2 Family Protein Expression and Platinum Drug Resistance in Ovarian Carcinoma," British Journal of Cancer—82 (2) :436-440 (2000).
Beurdeley-Thomas, et al., "The peripheral benzodiazepine receptors: a review," Journal of Neuro-Oncology 46 (2000) 45-56.
Blatt, Neal B., "Benzodiazepine-induced superoxide signals B cell apoptosis: mechanistic insight and potential therapeutic utility", The Journal of Clinical Investigation, Oct. 2002, vol. 110, No. 8., pp. 1123-1132.
Blum, P., et al., "Stiff-Person Syndrome: An Autoimmune Disease," Movement Disorders 6(1):12-20 (1991).
Boitano, Anthony, et al., "Structure activity studies of a novel cytotoxic benzodiazepine", Bioorganic & Medicinal Chemistry Letters, Oxford, GB, vol. 13, No. 19, 2003, pp. 3327-3330.
Bono et al., "Peripheral benzodiazepine receptor agonists exhibit potent antiapoptotic activities," Biochemical and Biophysical Research Communications, 1999, 265, pp. 457-461.
Boojamra, C.G., et al., "Solid-Phase Synthesis of 1,4. Benzodiazepine-2,5-Diones. Library Prep. and Demonstration of Synthesis Generality," J. Org. Chem.—62:1240-1256 (1997).
Bunin et al., "Synthesis and evaluation of 1,4-benzodiazepine libraries", Methods in Enzymology, 1996, 267, pp. 448-465.
Bunin, B.A., et al., "The Combinatorial Synthesis and Chemical and Biological Evaluation of a 1,4-Benzodiazepine Libra ," PNAS USA—91:4708-4712 (1994).
Bunin, BA., et al., "A General and Expedient Method for the Solid-Phase Synthesis of 1,4-Benzodlazepine Derivatives," J. Am. Chem. Soc.—114:10997-10998 (1992).
Chumakov,A.M., et al., "Analysis of p53 Transactivation Through High-Affinity Bindir•g Sites," Oncogene—8:3005o3011 (1993).
Churcher et al., "A new series of potent benzodiazepine y-Secretase inhibitors," Bioorganic & Medicinal Chemistry Letters 13 (2003) 179-.
Cohen, P.L., et al., "Lpr and gld: Single Gen• Models of Systemic Autoimmunity and Lymphoproliferative Disease,"Annu. Rev. Immunol. 9:243-269 (1991).

(56) References Cited

OTHER PUBLICATIONS

Cole et al., "The EBV-Hybridoma Technique and its Application to Human Lung Cancer", Monoclonal Antibodies and Cancer Therapy, Alan R. Liss, Inc., pp. 77-96 [1985].
Colosi, et al,"Mutational analysis of the intracellular domain of the human growth hormone recetor", J. Biol. Chem., 268:12617 [1993].
Crabtree, R.H., "A New Type of Hydrogen Bond," Science 282:2000-2001 1998.
Darrow et al., "Structurally similar small molecule photoaffinity CCK-A Agonists and Antagonists as Novel Tools . . .", Bioorganic & Medicinal Chemistry Letters 8 (1998) 3127-3132.
Desoize, B., "Anticancer Drug Resistance and Inhibition of Apoptosis," Anicancer Research—14:2291-2294 1994.
Dichek, David A., et al., "Seeding of intravascular stents with genetically engineered endothelial cells," Laboratory Investigation, 80:5 pp. 1347-1353 (1989).
Doble, A., et al., "Labelling of Peripheral-Type Benzodiazepine B Human Brain with [aH]I 1195: Anatomical and Subcellular Distribution," Brain Research Bulletin,18:49-61 1987.
Don, A. et al., Cancer Cell, vol. 3, May 2003 497-509.
Donadio, J.V., et al., Immunosuppressive Drug Therapy in Lupus Nephritis, American Journal of Kidney Diseases 21(3):239-250 1993.
EP Search, EP Patent Application No. 05856659.7, dated Dec. 9, 2008.
EP Search, EP Patent Application No. 04 775 923.8, dated Dec. 15, 2008.
Ermak, T.H., et al., "Treatment of Murine Lupus with Monoclonal Antibody to L3T4," Laboratory Investigation 61(4):447-456 1989.
Fuh et al, "Rational design of potent antagonists to the human growth hormone receptor", Science, 256:1677 [1992].
Gallant, J.E., et al.,"Incidence and Natural History of Cytomegalovirus Disease in Patients with Advanced Human . . ." The Journal of Infect. Disease, 166: 1223-1227 (1992).
Garcia-Calvo, M., et al. "Inhibition of Human Caspases by Peptide-Based and Macromolecular Inhibitors," The Journal of Biological Chemistry 273(49):32608-32613 1998.
Gorczyca, W., et al., "Induction of DNA Strand Breaks Associated with Apoptosis During Treatment of Leukemias," Leukemia 7(5):659-670 1993.
Gordon, C., et al.. "Chronic Therapy with Recombinant Tumor Necrosis Factor-α in Autoimmune NZB/NZW Fi Mice," Clinical Immunology and Immunopatholoy, 52:421-434 (1989).
Gordon, E.M., et al., Applications of Combinatorial Technologies to Drug Discovery. 2. Combinatorial Organic 52 Synthesis, Library Screening . . . Journal of Med. Chem. 37(10): (1994).
Grasberger, Bruce L., "Discovery and cocrystal structure of benzodiazepinedione HDM2 antagonists that activate p53 in cells", J. Med. Chem., 48, (2005), 909-912.
Gupta et al., "Psychitripic drugs in dermatology . . . " Database:EMbase (AN:86111413), Journal of the American Academy of Dermatology, 1986, vol. 14, No. 4, pp. 633-645.
Hahn, B.H., et al.; "Influence of Cyclophosphamide and Other Immunosuppressive Drugs on Immune Disorders . . . ," Arthritis and Rheumatism—18(2):145-152 (1975).
Hamann, L.G., et al., "Benzodiazepine-based selective inhibitors of mitochondrial F1F0 ATP hydrolase" Bioorganic & Medicinal Chemistry Ltrs. 14 pp. 1031-1034 (2004).
Hang, L., et al., "A Spontaneous Rheumatoid Arthritis-Like Disease in MR/1 Mice," J. Exp. Mod.—155:1690-1701 1982.
Herranz, R., "Cholesystokinin Antagonists: Pharmacological and Therapeutic Potential", Medicinal Research Reviews 23 (2003) 559-603.
Hirsch, et al., "PK11195, a Ligand of the Mitochondrial Benzodiazepine Receptor, Facilitates the Induction of Apoptosis and Reverses Bcl-2-Mediated Cytoprotection," Experimental Cell Research 241, 426-434 (1998).
Horowitz, R.E., et al., "Cyclophosphamide Treatment of Mouse Systemic Lupus Erythematosus," Laboratory Investigation 21 (3): 199-206 1969.
Hulme, C. J. "Improved procedure for the solution phase preparation of 1,4-benzodiazepine-2,5-dione libraries . . . ", Org. Chem., 63,(1998), 8021-8023.
Tarpley, et al., J. Chroni Diseases (1965), 18 (abstract only).
Dourlat, et al., "Novel 1,4-benzodiazepine derivaties with antiproliferative properties on tumor cell lines," Bioorganic & Medicinal Chemistry Letters, 2007, vol. 17, Issue 9, pp. 2527-2530.
Elz et al., 1989 Eur. J. Med Chem. 259-262.
Atwal et al., Tet Lett. 30, 1989, 7313.
Johnson, K.M., et al., Chemistry & Biology, 2005, 12:485-496.
Francis, T.M., et al., "Identification of cytotoxic, T-cell-selective 1,4-benzodiazepine-2,5-diones," Bioorganic & Medicinal Chemistry Letters, Pergamon, Elsevier Science, GB, vol. 16, No. 9, May 1, 2006, pp. 2423-2427.
Akssira, M., et al., "New Routes to 1,4-benzodiazepin-2,5-diones," Tetrahedron (1994), vol. 50, No. 30, pp. 9051-9060.
Mohiuddin, G., et al., "A Versatile Synthesis of 3H-1(H), 4(H)-Benzodiazepin-2,5-diones," Indian Journal of Chenmistry, 1985, vol. 24B, pp. 905-907.
Boojamra, Constantine G., et al., "An Expedient and High-Yielding Method for the Solid-Phase Synthesis of Diverse 1,4-Benzodiazepine-2, 5-diones," Journal of Organic Chemistry, 1995, vol. 60, No. 18, pp. 5742-5743.
Keating, Thomas A., et al., "A Remarkable Two-Step Synthesis of Diverse 1, 4-Benzodiazepine-2, 5-diones Using the Ugi Four-Component Condensation," Journal of Organic Chemistry, 1996, vol. 61, No. 25, pp. 8935-8939.
Juaristi, Eusebio, et al., "Enantioselective Synthesis of α-Amino Acides from Chiral 1, 4-enzodiazepine-2, 5-diones Contianing the α-Phenethyl Group," Journal of Organic Chemistry, Mar. 26, 1999, vol. 64, No. 8, pp. 2914-2918.
Marc, Gasper, et al., "High Yield Phase Transfer N-Alkylation of Some Benzodiazepinese by Esters of ω-Halo Acids," Synthetic Communications, 1998, vol. 28, No. 7, pp. 1143-1157.
Bolli, M.H., et al., "Novel Benzo[1,4]diazepin-2-one-Derivatives as Endothelin Receptor Antagonists", Journal of Medicinal Chemistry, vol. 47, No. 11, Apr. 23, 2004, pp. 2776-2795.
Cunha, 2006, "The first bismuth(III)-catalyzed guanylation of thioureas", Tetrahedron Letters 47:6955-56.
Cunha, 2002, "Bismuth nitrate pentahydrate: a new and environmentally benign reagent for guanidylation of N-benzoylthioureas", Tetrahedron Letters 43: 49-52.
Yano, Masafumi, et al., "Effect of Milrinone on Left Ventricular Relaxation and Ca2+ Uptake Function of Cardiac Sarcoplasmic Reticulum," Am. J. Physiol. Heart Circ. Physiol, 279: H1898-H1905 (2000).
Gatza, et al., "Manipulating the Bioenergetics of Alloreactive T Cells Causes Their Selective Apoptosis and Arrests Graft-Versus-Host Disease," Sci. Transl. Med. 3(67ra8): 1-8 (2011).
Shoemaker, et al., "The NC160 Human Tumour Cell Line Anticancer Drug Screen," Nat. Rev. Cancer 6:813-823 (2006).
Stevens, S.Y., et al., "Non Nucleic Acid Inhibitors of Protein-DNA Interactions Identified Through Combinatorial Chemistry," J. Am. Chem.Soc.—118:10650-10651 (1996).
Sugimoto, T., et al., Determination of Cell Surface Membrane Antigens . . . JNCI—73: (1):51-57 (1984).
Swanson et al, "Ligand recognition by anti-DNA Autoantibodies," Biochemistry, 35:1624-1633 [1996] (Abstract only).
Swanson, P.C., et al., "Ligand Recognition by Murine Anti-DNA Autoantibodies," J. Clin. Invest 97(7):1748-1760 (1996).
Swanson, P.C.,et al., "High Resolution Ephope Mapping of an Anti-DNA Autoantibody Using Model DNA Ligands," J. Immunology 71 152(5):2601-2612 (1994).
Takahashi, T., et al., "Generalized Lymphoproliferative Disease in Mice, Caused by a Point Mutation in the Fas Ligand;" Cell 76:969-976 (1994).
Tanimoto, Y., et al., Benzodiazepine Receptor Agonists Modulate Thymocyte Apoptosis Through Reduction of the Mitochondrial . . . Jpn. J. Pharmacol. 79:177-183 (1999).
Taupin, V., et al., Endogenous Anxiogenic peptide, ODN-Diazepam-Binding Inhibitor, and Benzodiazepines.. Lymphokine and Cytoklne Research 10(1):7-13 (1991).

(56) References Cited

OTHER PUBLICATIONS

Theoffopoulous, AN, et al., "Murine Models of Systemic Lupus Erythematosus," Advances in Immunology 37:269-390 (1985).
Thompson, C.B., "Apoptosis in the Pathogenesis and Treatment of Disease," Science 267:1456-1462 (1995).
Ursini et al., "Synthesis and SAR of New 5-Phenyl-3-ureido-1,5-benzodiazepines as cholecystokinin-B receptor antagonists", J. Med. Chem. 43 (2000) 3596-3613.
Walser, et al., "Quinazolines and 1,4-benzodiazepines. LILX. Preparation of Pyrrolo[2,1-c]-1,4-benzodiazepin-2-ones", J. Org. Chem. 38:3502-3507 (1973).
Watanabe-Fukunaga, R., et al., "Lymphoproliferation Disorder in Mice Explained by Defects in Fas Antigen that Mediates Apoptosis," Nature 356:314-317 (1992).
White, E., "Life, Death, and the Pursuit of Apoptosis," Genes & Development 10:1-15 (1996).
Williams, D. et al, "Identification of compounds the bind mitochondrial F1F0 ATPase by screening a triazine library . . . " Chemistry & Biol. 11:1251-1259, 9(2004).
Wu, G.Y. et al., "Receptor-Mediated in Vitro Gene Transformation by a Soluble DNA Carrier System," The Journal of Biological Chemistry 262(10):4429-4432 (1987).
Wyllie, A.H., "The Genetic Regulation of Apoptosis," Current Opinion in Genetics & Development 5:97-104 (1995).
Zamzami, N., et al., "Mitochondrial Control of Nuclear Apoptosis," J. Exp. Med. 183:1533-1544 1996.
Zoratti, M., et al., "The Mitochondrial Permeability Transition," Biochimica et Biophysica Acta 1241:139-176 (1995).
International Search Report, International Patent Application No. PCT/US02/26171 dated Aug. 8, 2003.
International Search Report, International Patent Application No. PCT/US01/11599 dated Mar. 6, 2001.
International Search Report, International Patent Application No. PCT/US05/031942 dated Sep. 21, 2006.
International Search Report, International Patent Application No. PCT/US04/013455 dated Jan. 6, 2006.
European Search Report, EP Patent Application No. 03 027 484.9-2117 dated May 3, 2004.
European Search Report, EP Patent Application No. 04 775 923.8-2123 dated Nov. 9, 2007.
European Search Report, EP Patent Application No. 00 928 586.7-2117 dated Apr. 23, 2002.
European Search Report, EP Patent Application No. 05 769 345.9 dated Oct. 22, 2007.
International Search Report, PCT/US2006/042753, dated May 6, 2008.
Written Opinion of the International Searching Authority, PCT/US06/21561, dated Aug. 17, 2007.
International Preliminary Report on Patentability, PCT/US2006/041446, mailed May 8, 2008.
International Search Report and Written Opinion, PCT/US2006/00442, mailed May 12, 2006.
International Report on Patentability, PCT/US2006/000442 mailed Jul. 12, 2007.
Puodziunaite, B., et al., "Bromination of Aromatic Ring of Tetrahydro-1,5-Benzodiazepin-2-Ones", Chemistry of Heterocyclic Compounds, vol. 36, No. 6, 2000.
AU Examiner's Report, AU Patent App. No. 2005323519 dated Nov. 27, 2007.
EP Search, EP Patent App. No. 03 027 484.9-2117, dated Jan. 31, 2005.
Nawrocka, et al., Arch. Pharm. (Weinheim) Jan. 2001, 334(1), 3-10.
International Search Report and Written Opinion, PCT/US08/56231, mailed Jun. 24, 2008.
International Search Report and Written Opinion, PCT/US05/14463, mailed Dec. 4, 2006.
International Search Report and Written Opinion, PCT/US07/11422, mailed Nov. 15, 2007.
International Search Report and Written Opinion, PCT/US07/13576, mailed Nov. 23, 2007.

Godic, "New approaches to psoriasis treatment. A review." 2004, Acta Dermatoven APA, vol. 13, No. 2, pp. 50-57.
International Search Report, PCT/US06/042753, mailed Apr. 19, 2007.
Desjardins, P and Stephanie Ledoux, "The Role of Apoptosis in Neurodegenerative Disease," Metabolic Brian Disease, vol. 13, No. 2, pp. 79-96 (1998).
International Search Report, PCT/US06/41446, mailed Aug. 1, 2007.
AU Patent Application No. 2006203946 Examiner's Report dated Sep. 10, 2008.
Iiangumaran, et al., "CD44 Selectively Associates with Active Src Family Protein Tyrosine Kinases Lck and Lyn in Glycosphingolipid-Rich . . . ", Blood, vol. 91, No. 10 (May 15, 1998), pp. 3901-3908.
Sato, et al., "CD22 negatively and positively regulates signal transduction through the B lymphocyte antigen receptor," seminars in Immunology, vol. 10, 1998, pp. 287-297.
Joshi, et al., "Oligomycin Sensitivey-conferring Protein (OSCP) of Mitochodrial ATP Synthase," The Journal of Biological Chemistry, vol. 267, No. 18,m Issue of Jun. 25, pp. 12860-12867, 1992.
EP Supplementary Search Report, EP Application No. 02794914.8 dated Nov. 6, 2008.
Lee, et al., J. Org. Chem. 1999, 64, 3060-3065.
Huse et al., "Generation of a Large Combinatorial Library of the Immunoglobulin Repertoire in Phage Lambda", Science, 246:1275-1281 [1989].
International Search Report and Written Opinion of PCT/US2008/057827 dated Oct. 6, 2008.
IPER and ISR for PCT/us02/31942 mailed Feb. 2, 2007.
Itoh, N., et al., "The Polypeptide Encoded by the cDNA for Human Cell Surface Antigen Fas Can Mediate Apoptosis," Cell 66:233-243 (1991).
Johnson, et al., "Mechanistic Basis for Therapeutic Targeting of the Mitochondrial FF-ATPase", downloaded from http://pubs.acs.org on Dec. 5, 2008, ASC Chem. Biol. 1 (5), 304-308, Publication Date (WEB): Jun. 9, 2006.
Jones, The non-conalent interaction of pyrrolo[2,1-c][benzodiazepines-5, 11-diones with DNA, Anti-Cancer Drug Design, 5:249-264 (1990).
Kamal, A., "Synthesis of DNA-interactive Pyrrolo[2,1-c][1,4] benzodiazepines by employing polymer-supported reagents . . . ," Synlett, 14,(2004), 2533-35.
Karle Jesper et al., "Diazepam protects against rat hippocampal neuronal cell death induced by antisense oligodeoxynucleotide to GABA-A receptor gamma-2 subunit" Brain Research, vol. 765, No. 1, 1997, pp. 21-29.
Kerver et al, "In situ detection of spontaneous superoxide anion and singlet oxygen production by mitochondria in . . . ", Histochem. J., 29:229-237 [1997] (Abstract only).
Kim et al., "Synthesis of 3-substituted 1,4-benzodiazepin-2-ones," J. Braz. Chem. Soc. 9:375-379 (1998).
Kohler and Milstein, "Continuous cultures of fused cells . . . ", Nature, 256:495-497 [1975].
Koopman, W.J., et al., "The MRL-Ipr/Ipr Mouse. A Model for the Study of Rheumatoid Arthritis," Scan& J. Rheumatolo Suppl 75:284-o289 (1988).
Korsmeyer, S.J., "Bcl-2 Initiates a New Category of Oncogenes: Regulators of Cell Death," Blood 80(4):879-886 (1992).
Kozbor, et al.• "The production of monoclonal antibodies from human lymphocytes", Immunol. Today, 4:72 [1983].
Lee, Sunwoo, et al., "Improved Catalysts for the Palladium-Catalyzed Synthesis of Oxindoles by . . . ", J. Org. Chem. 2001, 66, pp. 3402-3415.
Lewis et al., "Editors' view: Cancer pharmacotherapy: 21st century 'magic bullets' and changing paradigms", British Journal of Clinical Pharmacology, 2006, 62:1,pp. 1-4.
Liu, J.R., et al., "Bclox•. is Expressed in Ovarian Carcinoma and Modulates Chemotherapy-induced Apoptosis," Gynecologic Oncology 70:398-403 (1998).
Los, M., et al., The Role of Caspases in Development, Immunity, and Apoptotic Signal Transduction: Immunity—10:629-639 (1999).
Lowman, et al., "Mutational analysis and protein engineering of receptor-binding determinants in human placental lactogen", J. Biol. Chem. 266:10982 [1991].

(56) References Cited

OTHER PUBLICATIONS

Luria, et al., "Tumor Viruses", General Viology 3rd edition,. 436-446 (1978)—Eds. John Wile & Sons, New York.
Malgrange, B., et al., "I•—Carbolines Induce Apoptotic Death of Cerebellar Granule Neurones in Cultures," NeuroReport 7(18):3041-3045 (1996).
Marino, M., et al., "Prevention of Systemic Lupus Erythematosus in MRL/Ipr Mice by Administration of an Immunoglobulin . . . ," Nature Biotechnology—18:735-739 (2000).
McDonnell'—349:254-256T'J et al., Progression from Lymphoid Hyperplasia to High-Grade . . . Nature—349:254-256 (1991).
Miccoli, et al., "Potentiation of Lonidamine and Diazepam . . . ", Journal of the National Cancer Institute, vol. 90, No. 18, pp. 1400-1406, Sep. 1998.
Miernik et al., "The antimitotic activities of some benzodiazepines", Experientia, 1986, 42, pp. 956-958.
Miller, K.A., et al., "Benzodiazepines Prevent Neuronal Death by Apoptosis & Necrosis . . . ," Society for Neuroscience Abstracts—24(1-2):979 (1998).
Monks, A., et., Feasibility of High-Flux Anticancer Drug Screen Using a Diverse Panel of Cultured Human Tumor Cell Lines, Journal of the National Cancer Institute, 83:757-766 (1991).
Nagata, S., "Human Autoimmune Lymphoproliferative Syndrome, a Defect in the Apoptosis-Inducing Fas Receptor: A 55 Lesson from the Mouse Model," J. Hum. Genet 43:2-8 (1998).
Okuyama, H., et al., "Analysis of Defective Delayed-Type Hypersensitivity in Autoimmune Mice Bearing Ipr Gene," Clln. Ex p. ImmunoL 63:87-94 1986.
Okuyama, H., et al., "Effect of Cyclophosphamide Pretreatment on Defective Delayed-Type Hypersensitivity . . . ," Int Arch. Allergy Appl. Immunol. 88:394-401 (1989).
Ozols, R.F., "Paclitaxel Plus Carboplatin in the Treatment of Ovarian Cancer," Seminars in Oncology 26(1) (Supp.2:84-89 (1999).
Paola Costantini et al., "Mitochondrion as Novel Target of Anticancer Chemotherapy", JNCI Journal of the National Cancer Institute 2000 92(13): 1042-1053; doi:10. 1093/jnci/92. 13. 1042.
Parks, Daniel J. "1,4-benzodiazepine-2,5-diones as small molecule antagonists of the HDM2-p53 interaction . . . " Bioorg Med Chem. Ltrs,. 15,(2005), 765-770.
Paull, K.D., et al., "Display and analysis of patterns of differential activity of drugs against human tumor . . . ", J. Natl. Cancer Inst., 81:1088-1092 [1989] (Abstract only).
Pestell, K.E., et al., "Charactehsation of the P53 Status, BCL-2 Expression and Radiation and Platinum Drug Sensitivity of . . . ," Int J. Cancer—77:913-918 (1998).

Giuseppe Piedimonte, et al., "Association of Tyrosine Protein Kinase Activity With Mitochondria in Human Fibroblasts," Journal of Cellular Biochemistry 32:113-123 (1986).
Raboisson, P. "Structure-based design, synthesis and biological evaluative of novel 1,4-diazepines as HDM2 antagonists," Bioorg Med Chem. Ltrs., 15,(2005), 1857-1861.
Ramdas et al., "Benzodiazepine compounds as inhibitors of the Src protein tyrosine kinase . . . " Archives of Biochemistry and Biophysics 368 (1999) 394-400.
Raynaud, F.I., et al., "Intracellular Metabolism of the Orally Active Platinum Drug JM216: Influence of Glutathione Levels," Br. J. Cancer 74(3) :380-?386 (1996).
Russell, J.H., et al., "Mature T Cells of Autoimmune Ipr/Ipr Mice have a Defect in Antigen-Stimulated Suicide," Proc. Nat. Acad. Sci. USA 90:4409-4413 (1993).
Sakata, K., et al., "Role of Fas/FasL Interaction in Physiology and Pathology: The Good and the Bad," Clinical Immunology and Immunopathology 87(1):1-7 (1998).
Sandstrom, P.A., et al., Autocrine Production of Extracellular Catalase Prevents Apoptosis.. Proc. Natl. Acad. Sci. USA—90:4708-4712 (1993).
Schlumpf, M., et al., "Delayed Developmental Immunotoxicity of Prenatal Benzodiazepines," Toxic. In Vitro—8(5):1061-1065(1994).
Schoemaker, H., et al., "Specific High-Affinity Binding Sites for [3H]Ro5—4864 in Rat Brain and Kidney," The J. of Pharmacology and Experimental Therapeutics; vol. 225(1)61-69 (1983).
Schwab, M., et al., "Amplified DNA with Limited Homology to myc Cellular Oncogene is Shared by Human Neuroblastoma Cell Lines and . . . ," Nature—305:245-248 (1983).
Scott, C.F., et al., "Comparison of Antigen-Specific T Cell Responses in Autoimmune MRL/Mp-Ipr/Ipr and MRL/Mp-+/+ Mice," The Journal of Immunology, vol. 132, No. 2, pp. 633-639 (1984).
Sentman, C.L., et al., "bcl-2 Inhibits Multiple Forms of Apoptosis but not Negative Selection in Thymocytes," Cell 67:879-886 (1991).
Shaughnessy, Kevin, H., et al., "Palladium-Catalyzed Inter- and Intramolecular . . . " J. Org. Chem. 1998, 63, pp. 6546-6553.
Sheppard, R.C., et al., "Acid-Labile Resin Linkage Agents for Use in Solid Phase Peptide Synthesis;" Int J. Peptide Protein Res. 20:451-454 (1982).
Snyder, Jane R., et al, "Dissection of melanogenesis with small molecules identifies prohibition as a regulator", Chemistry & Biol. 12:477-484, 4(2005).
European Search Report, EP Patent Application No. 10817891.4, dated Aug. 2, 2013, 18 pages.
Ishiyama et al., "Palladium(0)-Catalyzed Cross-Coupling Reaction of Alkoxydiboron with Haloarenes: A Direct Procedure for Arylboronic Esters," J. Org. Chem., 1995, 60:7508-7510.

BENZODIAZEPINONE COMPOUNDS AND METHODS OF TREATMENT USING SAME

CROSS REFERENCE TO RELATED APPLICATIONS

This application is a U.S. §371 national stage entry of pending International Patent Application No. PCT/US2010/049282, international filing date Sep. 17, 2010, which claims the benefit of and priority to expired U.S. Provisional Patent Application Ser. No. 61/243,792, filed Sep. 18, 2009, the contents of which are hereby incorporated by reference for all purposes.

FIELD OF THE INVENTION

The present invention relates to inhibitors of $F_1F_0$-ATPases (e.g., mitochondrial $F_1F_0$-ATPases), and their therapeutic use. In particular, the present invention relates to 1,4-benzodiazepinone compounds that inhibit $F_1F_0$-ATPase, and methods of using 1,4-benzodiazepinone compounds as therapeutic agents to treat a number of medical conditions.

BACKGROUND OF THE INVENTION

Multicellular organisms exert precise control over cell number. A balance between cell proliferation and cell death achieves this homeostasis. Cell death occurs in nearly every type of vertebrate cell via necrosis or through a suicidal form of cell death, known as apoptosis. Apoptosis is triggered by a variety of extracellular and intracellular signals that engage a common, genetically programmed death mechanism.

Multicellular organisms use apoptosis to instruct damaged or unnecessary cells to destroy themselves for the good of the organism. Control of the apoptotic process therefore is very important to normal development, for example, fetal development of fingers and toes requires the controlled removal, by apoptosis, of excess interconnecting tissues, as does the formation of neural synapses within the brain. Similarly, controlled apoptosis is responsible for the sloughing off of the inner lining of the uterus (the endometrium) at the start of menstruation. While apoptosis plays an important role in tissue sculpting and normal cellular maintenance, it is also a component of the primary defense against cells and invaders (e.g., viruses) which threaten the well being of the organism.

Not surprisingly many diseases are associated with dysregulation of apoptotic cell death. Experimental models have established a cause-effect relationship between aberrant apoptotic regulation and the pathagenicity of various neoplastic, autoimmune and viral diseases. For instance, in the cell-mediated immune response, effector cells (e.g., cytotoxic T lymphocytes "CTLs") destroy virus-infected cells by inducing the infected cells to undergo apoptosis. The organism subsequently relies on the apoptotic process to destroy the effector cells when they are no longer needed. Autoimmunity is normally prevented by the CTLs inducing apoptosis in each other and even in themselves. Defects in this process are associated with a variety of immune diseases such as lupus erythematosus and rheumatoid arthritis.

Multicellular organisms also use apoptosis to instruct cells with damaged nucleic acids (e.g., DNA) to destroy themselves prior to becoming cancerous. Some cancer-causing viruses overcome this safeguard by reprogramming infected (transformed) cells to abort the normal apoptotic process. For example, several human papilloma viruses (HPVs) have been implicated in causing cervical cancer by suppressing the apoptotic removal of transformed cells by producing a protein (E6) which inactivates the p53 apoptosis promoter. Similarly, the Epstein-Barr virus (EBV), the causative agent of mononucleosis and Burkitt's lymphoma, reprograms infected cells to produce proteins that prevent normal apoptotic removal of the aberrant cells thus allowing the cancerous cells to proliferate and to spread throughout the organism.

Still other viruses destructively manipulate a cell's apoptotic machinery without directly resulting in the development of a cancer. For example, the destruction of the immune system in individuals infected with the human immunodeficiency virus (HIV) is thought to progress through infected $CD4^+$ T cells (about 1 in 100,000) instructing uninfected sister cells to undergo apoptosis.

Some cancers that arise by non-viral means have also developed mechanisms to escape destruction by apoptosis. Melanoma cells, for instance, avoid apoptosis by inhibiting the expression of the gene encoding Apaf-1. Other cancer cells, especially lung and colon cancer cells, secrete high levels of soluble decoy molecules that inhibit the initiation of CTL mediated clearance of aberrant cells. Faulty regulation of the apoptotic machinery has also been implicated in various degenerative conditions and vascular diseases.

It is apparent that controlled regulation of the apoptotic process and its cellular machinery is vital to the survival of multicellular organisms. Typically, the biochemical changes that occur in a cell instructed to undergo apoptosis occur in an orderly procession. However, as shown above, flawed regulation of apoptosis can cause serious deleterious effects in the organism.

There have been various attempts to control and restore regulation of the apoptotic machinery in aberrant cells (e.g., cancer cells). For example, much work has been done to develop cytotoxic agents to destroy aberrant cells before they proliferate. As such, cytotoxic agents have widespread utility in both human and animal health and represent the first line of treatment for nearly all forms of cancer and hyperproliferative immune disorders like lupus erythematosus and rheumatoid arthritis.

Many cytotoxic agents in clinical use exert their effect by damaging DNA (e.g., cis-diaminodichloroplatanim(II) cross-links DNA, whereas bleomycin induces strand cleavage). The result of this nuclear damage, if recognized by cellular factors like the p53 system, is to initiate an apoptotic cascade leading to the death of the damaged cell.

However, existing cytotoxic chemotherapeutic agents have serious drawbacks. For example, many known cytotoxic agents show little discrimination between healthy and diseased cells. This lack of specificity often results in severe side effects that can limit efficacy and/or result in early mortality. Moreover, prolonged administration of many existing cytotoxic agents results in the expression of resistance genes (e.g., bcl-2 family or multi-drug resistance (MDR) proteins) that render further dosing either less effective or useless. Some cytotoxic agents induce mutations in p53 and related proteins. Based on these considerations, ideal cytotoxic drugs should only kill diseased cells and not be susceptible to chemoresistance.

One strategy to selectively kill diseased cells or block their growth is to develop drugs that selectively recognize molecules expressed in diseased cells. Thus, effective cytotoxic chemotherapeutic agents, would recognize disease indicative molecules and induce (either directly or indirectly) the death of the diseased cell. Although markers on some types of cancer cells have been identified and targeted with therapeutic antibodies and small molecules, unique traits for diagnostic and therapeutic exploitation are not known for most cancers. Moreover, for diseases like lupus, specific molecular targets for drug development have not been identified.

The need exists for improved compositions and methods for regulating the apoptotic processes in subjects afflicted with diseases and conditions characterized by faulty regulation of these processes (e.g., viral infections, hyperproliferative autoimmune disorders, chronic inflammatory conditions, and cancers). The present invention addresses this need and has other related advantages.

SUMMARY

The present invention provides inhibitors of $F_1F_0$-ATPases (e.g., mitochondrial $F_1F_0$-ATPases), and methods for treating various conditions using such inhibitors.

In one aspect, the invention provides a family of compounds represented by Formula I:

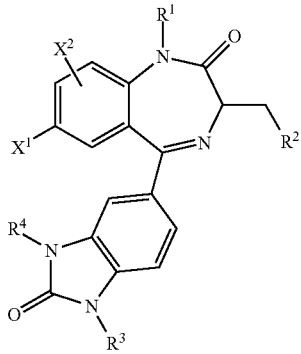

I including a pharmaceutically acceptable salt thereof, wherein the variables are as defined in the detailed description.

In another aspect, the invention provides a family of compounds represented by Formula II:

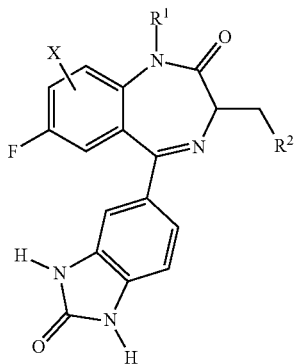

II including a pharmaceutically acceptable salt thereof, wherein the variables are as defined in the detailed description.

In another aspect, the invention provides a family of compounds represented by Formula III:

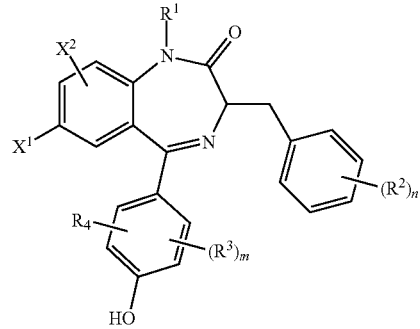

III including a pharmaceutically acceptable salt thereof, wherein the variables are as defined in the detailed description.

The foregoing compounds can be present in pharmaceutical compositions comprising a compound described herein and a pharmaceutically acceptable carrier.

In another aspect, the invention provides a method of treating a patient suffering from a medical condition, comprising administering to the patient a therapeutically effective amount of one or more benzodiazepinone compounds described herein. A large number of diseases can be treated using the benzodiazepinone compounds described herein. For example, the compounds described herein may be used to treat diseases characterized by dysregulation of necrosis and/or apoptosis processes in a cell or tissue, diseases characterized by aberrant cell growth and/or hyperproliferation, etc. In particular, the compounds described herein may be used to treat, for example, rheumatoid arthritis, psoriasis, graft-versus-host disease, Crohn's disease, inflammatory bowel disease, multiple sclerosis, psoriasis, systemic lupus erythematosus, Celiac Sprue, idiopathic thrombocytopenic thrombotic purpura, myasthenia gravis, Sjogren's syndrome, scleroderma, ulcerative colitis, asthma, cardiovascular disease, myeloma, lymphoma, cancer, and bacterial infection.

In certain embodiments, the compositions of the present invention are used to treat immune/chronic inflammatory conditions (e.g., psoriasis, autoimmune disorders, organ-transplant rejection, epidermal hyperplasia, Crohn's disease, inflammatory bowel disease, and multiple sclerosis). In even further embodiments, the compositions of the present invention are used in conjunction with stenosis therapy to treat compromised (e.g., occluded) vessels. In some embodiments, the composition comprising a benzodiazepinone compound is administered under conditions (e.g., timing, dose, co-administration with other agent, mode of administration, selection of subject, use of targeting agents, etc.) that maximize desired effects directed at the $F_1F_0$-ATPase. In some embodiments, the subject is also administered Bz-423 or a related compound (see, e.g., U.S. Pat. Nos. 7,144,880 and 7,125,866, U.S. patent application Ser. Nos. 12/044,589, 11/586,097, 11/585,492, 11/445,010, 11/324,419, 11/176,719, 11/110, 228, 10/935,333, 10/886,450, 10/795,535, 10/634,114, 10/427, 211, 10/217,878, and 09/767,283, and U.S. Provisional Patent Nos. 60/878,519, 60/812,270, 60/802,394, 60/732,045, 60/730,711, 60/704,102, 60/686,348, 60/641, 040, 60/607,599, and 60/565,788).

In another aspect, the invention provides a method of treating a disorder selected from the group consisting of rheumatoid arthritis, psoriasis, graft-versus-host disease, Crohn's disease, inflammatory bowel disease, multiple sclerosis, systemic lupus erythematosus, Celiac Sprue, idiopathic thrombocytopenic thrombotic purpura, myasthenia gravis, Sjogren's syndrome, scleroderma, ulcerative colitis, asthma, epidermal hyperplasia, cardiovascular disease, myeloma, lymphoma, cancer, and bacterial infection, comprising administering a therapeutically effective amount of a compound described herein, e.g., as Formula I, II, or III as described herein, to a patient in need thereof to ameliorate a symptom of the disorder.

In certain embodiments, the compound is embraced by Formula I described above. In certain other embodiments, the compound is one of the compounds listed in Tables 1-4. In certain embodiments, the disorder is Crohn's disease, inflammatory bowel disease, multiple sclerosis, graft-versus-host disease, systemic lupus erythematosus, rheumatoid arthritis, or psoriasis. In certain other embodiments, the disorder is rheumatoid arthritis, graft-versus-host disease, or inflammatory bowel disease. In certain other embodiments, the disorder is myeloma, lymphoma, cardiovascular disease, or cancer. In certain embodiments, the disorder is a bacterial infection. In certain other embodiments, the patient is a human.

In another aspect, the invention provides a method of inhibiting an $F_1F_0$-ATPase, for example, a mitochondrial $F_1F_0$-ATPase. The method comprises exposing the $F_1F_0$-ATPase to a compound of described herein, e.g., a Formula of I, II, or III as described herein, to inhibit said $F_1F_0$-ATPase.

DEFINITIONS

To facilitate an understanding of the present invention, a number of terms and phrases are defined below.

The term "chemical moiety" refers to any chemical compound containing at least one carbon atom. Examples of chemical moieties include, but are not limited to, aromatic chemical moieties, chemical moieties comprising sulfur, chemical moieties comprising nitrogen, oxygen, hydrophilic chemical moieties, and hydrophobic chemical moieties.

The term "alkyl" is art-recognized and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "alkylene" is art-recognized and refers to a straight or branched, saturated aliphatic, divalent radical having the number of carbon atoms indicated (e.g., $(C_{1-6})$alkylene includes methylene ($-CH_2-$), ethylene ($-CH_2CH_2-$), trimethylene ($-CH_2CH_2CH_2-$), and the like.)

The term "haloalkyl" is art-recognized and refers to an alkyl group that is substituted with at least one halogen. For example, $-CH_2F$, $-CHF_2$, $-CF_3$, $-CH_2CF_3$, $-CF_2CF_3$, and the like.

The term "hydroxyalkyl" refers to an alkyl group that is substituted with an $-OH$ group. For example, $-CH_2OH$, $-CH_2CH_2OH$, $-CH_2CH_2OH$, $-CH_2C(H)(OH)CH_3$, $-CH_2CH_2CH_2OH$, and the like.

The term "alkoxy" is art-recognized and refers to an alkyl group attached to an oxygen atom ($-O$-alkyl). Exemplary alkoxy groups include, but are not limited to methoxy, ethoxy, propoxy, etc.

The term "aralkyl" refers to an alkyl group substituted with an aryl group.

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to a carbocyclic aromatic group. Representative aryl groups include phenyl, naphthyl, anthracenyl, and the like. The aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, $-C(O)$alkyl, $-CO_2$alkyl, carbonyl, carboxyl, alkylthio, sulfonyl, sulfonamido, sulfonamide, ketone, aldehyde, ester, heterocyclyl, aryl or heteroaryl moieties, $-CF_3$, $-CN$, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. In certain embodiments, the aromatic ring is not substituted, i.e., an unsubstituted aryl. The term "haloaryl" refers to an aryl group that is substituted with at least one halogen.

The "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. The heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, $-C(O)$alkyl, $-CO_2$alkyl, carbonyl, carboxyl, alkylthio, sulfonyl, sulfonamido, sulfonamide, ketone, aldehyde, ester, heterocyclyl, aryl or heteroaryl moieties, $-CF_3$, $-CN$, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaromatic ring is not substituted, i.e., an unsubstituted heteroaryl. The term "haloheteroaryl" refers to an heteroaryl group that is substituted with at least one halogen.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

As used herein, the term "substituted aryl" refers to an aromatic ring or fused aromatic ring system consisting of at least one aromatic ring, and where at least one of the hydrogen atoms on a ring carbon has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to an aliphatic structure containing a fused ring system. Examples of such include, but are not limited to, decalin and the like.

As used herein, the term "substituted cycloaliphatic" refers to a cycloaliphatic structure where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicyclo-heptanes, octanes, and nonanes (e.g., nonrbornyl) and the like.

As used herein, the term "heterocyclic" represents, for example, an aromatic or nonaromatic ring containing one or more heteroatoms. The heteroatoms can be the same or different from each other. Examples of heteratoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like.

The term "derivative" of a compound, as used herein, refers to a chemically modified compound wherein the chemical modification takes place either at a functional group of the compound (e.g., aromatic ring) or on the benzodiazepine backbone. Such derivatives include, but are not limited to, esters of alcohol-containing compounds, esters of carboxy-containing compounds, amides of amine-containing compounds, amides of carboxy-containing compounds, imines of amino-containing compounds, acetals of aldehyde-containing compounds, ketals of carbonyl-containing compounds, and the like.

The term "IC$_{50}$" is art-recognized and refers to the concentration of a compound that is required for 50% inhibition of its target.

The term "EC$_{50}$" is art-recognized and refers to the concentration of a compound at which 50% of its maximal effect is observed.

As used herein, the terms "subject" and "patient" refer to organisms to be treated by the methods of the present invention. Such organisms preferably include, but are not limited to, mammals (e.g., murines, simians, equines, bovines, porcines, canines, felines, and the like), and most preferably includes humans. In the context of the invention, the terms "subject" and "patient" generally refer to an individual who will receive or who has received treatment (e.g., administration of a compound of the present invention and optionally one or more other agents) for a condition characterized by the dysregulation of apoptotic processes.

In some embodiments, the "target cells" of the compositions and methods of the present invention include, refer to, but are not limited to, lymphoid cells or cancer cells. Lymphoid cells include B cells, T cells, and granulocytes. Granulocyles include eosinophils and macrophages. In some embodiments, target cells are continuously cultured cells or uncultered cells obtained from patient biopsies.

In one specific embodiment, the target cells exhibit pathological growth or proliferation. As used herein, the term "pathologically proliferating or growing cells" refers to a localized population of proliferating cells in an animal that is not governed by the usual limitations of normal growth.

As used herein, the term "un-activated target cell" refers to a cell that is either in the $G_o$ phase or one to which a stimulus has not been applied.

As used herein, the term "activated target lymphoid cell" refers to a lymphoid cell that has been primed with an appropriate stimulus to cause a signal transduction cascade, or alternatively, a lymphoid cell that is not in $G_o$ phase. Activated lymphoid cells may proliferate, undergo activation induced cell death, or produce one or more cytotoxins, cytokines, or other related membrane-associated proteins characteristic of the cell type (e.g., CD8$^+$ or CD4$^+$). They are also capable of recognizing and binding any target cell that displays a particular antigen on its surface, and subsequently releasing its effector molecules.

As used herein, the term "activated cancer cell" refers to a cancer cell that has been primed with an appropriate stimulus to cause signal transduction. An activated cancer cell may or may not be in the $G_O$ phase.

An activating agent is a stimulus that upon interaction with a target cell results in a signal transduction cascade. Examples of activating stimuli include, but are not limited to, small molecules, radiant energy, and molecules that bind to cell activation cell surface receptors. Responses induced by activation stimuli can be characterized by changes in, among others, intracellular $Ca^{2+}$, superoxide, or hydroxyl radical levels; the activity of enzymes like kinases or phosphatases; or the energy state of the cell. For cancer cells, activating agents also include transforming oncogenes.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route.

As used herein, the term "dysregulation of the process of cell death" refers to any aberration in the ability (e.g., predisposition) of a cell to undergo cell death via either necrosis or apoptosis. Dysregulation of cell death is associated with or induced by a variety of conditions, including for example, immune disorders (e.g., systemic lupus erythematosus, autoimmune disorders, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes, papilloma, HIV), and other conditions such as osteoarthritis and atherosclerosis.

It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

A "hyperproliferative disorder," as used herein refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A metastatic cell or tissue means that the cell can invade and destroy neighboring body structures. Hyperplasia is a form of cell proliferation involving an increase in cell number in a tissue or organ, without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium.

The pathological growth of activated lymphoid cells often results in an immune disorder or a chronic inflammatory condition. As used herein, the term "immune disorder" refers to any condition in which an organism produces antibodies or immune cells which recognize the organism's own molecules, cells or tissues. Non-limiting examples of immune disorders include autoimmune disorders, immune hemolytic anemia, immune hepatitis, Berger's disease or IgA nephropathy, Celiac Sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjorgren syndrome, systemic lupus erythematosus, type 1 diabetes, ulcerative colitis, vitiligo, tuberculosis, and the like.

As used herein, the term "chronic inflammatory condition" refers to a condition wherein the organism's immune cells are activated. Such a condition is characterized by a persistent inflammatory response with pathologic sequelae. This state is characterized by infiltration of mononuclear cells, proliferation of fibroblasts and small blood vessels, increased connective tissue, and tissue destruction. Examples of chronic inflammatory diseases include, but are not limited to, Crohn's disease, psoriasis, chronic obstructive pulmonary disease, inflammatory bowel disease, multiple sclerosis, and asthma. Immune diseases such as rheumatoid arthritis and systemic lupus erythematosus can also result in a chronic inflammatory state.

As used herein, the term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "sample" as used herein is used in its broadest sense. A sample suspected of indicating a condition characterized by the dysregulation of apoptotic function may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the terms "purified" or "to purify" refer to the removal of undesired components from a sample. As used herein, the term "substantially purified" refers to molecules that are at least 60% free, preferably 75% free, and most preferably 90%, or more, free from other components with which they usually associated.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "modulate" refers to the activity of a compound (e.g., a compound of the present invention) to affect (e.g., to promote or retard) an aspect of cellular function, including, but not limited to, cell growth, proliferation, apoptosis, and the like.

As used herein, the term "competes for binding" is used in reference to a first molecule (e.g., a first compound of the present invention) with an activity that binds to the same target (e.g., the oligomycin sensitivity conferring protein in mitochondrial ATP synthase) as does a second molecule (e.g., a second compound of the present invention or other molecule that binds to the oligomycin sensitivity conferring protein in mitochondrial ATP synthase, etc.). The efficiency (e.g., kinetics or thermodynamics) of binding by the first molecule may be the same as, or greater than, or less than, the efficiency of the target binding to the second molecule. For example, the equilibrium binding constant ($K_D$) for binding to the substrate may be different for the two molecules.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that modulate apoptosis in cells.

As a general matter, compositions specifying a percentage are by weight unless otherwise specified.

Further, if a variable is not accompanied by a definition, then the previous definition of the variable controls. Generic chemical structures are intended to encompass all stereoisomeric forms (e.g., racemic mixtures, enantiomers, diastereomers, etc.) unless indicated otherwise. From the description herein, it will be apparent to the skilled artisan that many specific examples are represented by the generic chemical formulae, definitions for variables associated with the generic chemical formulae, and, in certain embodiments, methods of using such compounds to treat various medical disorders. To illustrate, in one example, $X^1$ is Cl and $X^2$ is H in Formula I. Whereas, in another example, $X^1$ is F and $X^2$ is halogen in Formula I. A wide variety of such combinations arising from selecting a particular group at each substituent position are possible and all such combinations are within the scope of this invention. Furthermore, use of particular families of compounds, e.g., a compound of Formula I, or, alternatively for example, a compound of Formula II, are contemplated for use in methods of treating one or more of the medical disorders described herein. To illustrate, in one example, a compound of Formula I is used in a method of treating rheumatoid arthritis. Whereas, in another example, a compound of Formula I is used in a method of treating graft-versus-host disease. Further combinations will be appreciated by the skilled artisan upon review of the description herein.

DETAILED DESCRIPTION OF THE INVENTION

The present invention relates to inhibitors of $F_1F_0$-ATPases (e.g., mitochondrial $F_1F_0$-ATPases) and their therapeutic use. In particular, the present invention provides benzodiazepinone compounds useful as $F_1F_0$-ATPase inhibitors, and methods of using such compounds as therapeutic agents to treat a number of different conditions.

Exemplary compositions and methods of the present invention are described in more detail in the following sections: I. Modulators of $F_1F_0$-ATPase Activity; II. 1,4-Benzodiazepinone Compounds; III. Therapeutic Applications of 1,4-Benzodiazepinone Compounds; and IV. Pharmaceutical Compositions, Formulations, and Exemplary Administration Routes and Dosing Considerations.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as "Comprehensive Organic Synthesis" (B. M. Trost & I. Fleming, eds., 1991-1992); "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Modulators of $F_1F_0$-ATPase Activity

In some embodiments, the present invention regulates $F_1F_0$-ATPase activity (e.g., mitochondrial $F_1F_0$-ATPase activity) through the exposure of cells to compounds of the present invention. In some embodiments, the compounds inhibit ATP synthesis and ATP hydrolysis. The effect of the compounds can be measured by detecting any number of cellular changes. For example, mitochondrial $F_1F_0$-ATPase activity and/or cell death may be assayed as described herein and in the art. In some embodiments, cell lines are maintained under appropriate cell culturing conditions (e.g., gas ($CO_2$), temperature and media) for an appropriate period of time to attain exponential proliferation without density dependent constraints. Cell number and or viability are measured using standard techniques, such as trypan blue exclusion/hemocytometry, or a MTT dye conversion assay. Alternatively, the cell may be analyzed for the expression of genes or gene products associated with aberrations in apoptosis or necrosis.

In some embodiments, exposing the compounds of the present invention to a cell induces apoptosis. In some embodiments, the present invention induces apoptosis or arrest of cell proliferation through interacting with the mitochondrial $F_1F_0$-ATPase. In some embodiments, the compounds of the present invention inhibit mitochondrial $F_1F_0$-ATPase activity through binding the OSCP. In some embodiments, the compounds of the present invention bind the junction between the OSCP and the $F_1$ subunit of the mitochondrial $F_1F_0$-ATPase. In some embodiments, the compounds of the present invention bind the $F_1$ subunit. In certain embodiments, screening assays of the present invention permit detection of binding partners of the OSCP, $F_1$, or OSCP/$F_1$ junction.

In some embodiments, exposing a compound described herein to a cell induces apoptosis. In some embodiments, the compound causes an initial increase in cellular ROS levels (e.g., $O_2^-$). In further embodiments, exposure of the compound to a cell causes an increase in cellular $O_2^-$ levels. In still further embodiments, the increase in cellular $O_2^-$ levels resulting from the compound is detectable with a redox-sensitive agent that reacts specifically with $O_2^-$ (e.g., dihydroethidium (DHE)).

In other embodiments, increased cellular $O_2^-$ levels resulting from compounds described herein diminish after a period of time (e.g., 10 minutes). In other embodiments, increased cellular $O_2^-$ levels resulting from the compounds diminish after a period of time and increase again at a later time (e.g., 10 hours). In further embodiments, increased cellular $O_2^-$ levels resulting from the compounds diminish at 1 hour and increase again after 4 hours. In some embodiments, an early increase in cellular $O_2^-$ levels, followed by a diminishing in cellular $O_2^-$ levels, followed by another increase in cellular $O_2^-$ levels resulting from the compounds is due to different cellular processes (e.g., bimodal cellular mechanisms).

In some embodiments, a compound described herein causes a collapse of a cell's mitochondrial transmembrane potential ($\Delta\Psi_m$). In some embodiments, a collapse of a cell's mitochondrial $\Delta\Psi_m$ resulting from the compound is detectable with a mitochondria-selective potentiometric probe (e.g., 3,3'-Dihexyloxacarbocyanine iodide, $DiOC_6$). In further embodiments, a collapse of a cell's mitochondrial $\Delta\Psi_m$ resulting from the compound occurs after an initial increase in cellular $O_2^-$ levels.

In some embodiments, the present invention enables caspase activation. In other embodiments, a compound described herein causes the release of cytochrome c from mitochondria. In further embodiments, the compound alters cystolic cytochrome c levels. In still other embodiments, altered cystolic cytochrome c levels resulting from compound are detectable by immunoblotting cytosolic fractions. In some embodiments, diminished cystolic cytochrome c levels resulting from the compound are detectable after a period of time (e.g., 10 hours). In further preferred embodiments, diminished cystolic cytochrome c levels resulting from the compound are detectable after 5 hours.

In other embodiments, the present invention causes the opening of the mitochondrial permeability transition pore. In some embodiments, the cellular release of cytochrome c resulting from a compound described herein is consistent with a collapse of mitochondrial $\Delta\Psi_m$. In still further preferred embodiments, the compound causes an increase in cellular $O_2^-$ levels after a mitochondrial $\Delta\Psi_m$ collapse and a release of cytochrome c. In further preferred embodiments, a rise in cellular $O_2^-$ levels is caused by a mitochondrial $\Delta\Psi_m$ collapse and release of cytochrome c resulting from the compound.

In other embodiments, the present invention causes cellular caspase activation. In some embodiments, caspase activation resulting from a compound described herein is measurable with a pan-caspase sensitive fluorescent substrate (e.g., FAM-VAD-fmk). In still further embodiments, caspase activation resulting from the compound tracks with a collapse of mitochondrial $\Delta\Psi_m$. In other embodiments, the compound causes an appearance of hypodiploid DNA. In some embodiments, an appearance of hypodiploid DNA resulting from the compound is slightly delayed with respect to caspase activation.

In some embodiments, the molecular target for the present invention is found within mitochondria. In further embodiments, the molecular target of the present invention involves the mitochondrial ATPase. The primary sources of cellular ROS include redox enzymes and the mitochondrial respiratory chain (hereinafter MRC). In some embodiments, cytochrome c oxidase (complex IV of the MRC) inhibitors (e.g., $NaN_3$) preclude a present invention dependent increase in cellular ROS levels. In other preferred embodiments, the ubiquinol-cytochrome c reductase component of MRC complex III inhibitors (e.g., FK506) preclude a present invention dependent increase in ROS levels.

In some embodiments, an increase in cellular ROS levels result from the binding of the compounds of the present invention to a target within mitochondria. In some embodiments, the compounds of the present invention oxidize 2',7'-dichlorodihydrofluorescin (hereinafter DCF) diacetate to DCF. DCF is a redox-active species capable of detecting ROS. In further embodiments, the rate of DCF production resulting from the present invention increases after a lag period.

Antimycin A generates $O_2^-$ by inhibiting ubiquinol-cytochrome c reductase. In some embodiments, the present invention provides compounds that increase cellular ROS and this ROS is believed to arise from ubiquinol-cytochrome c. In further embodiments, the present invention increases cellular ROS production under aerobic conditions supporting state 3 respiration. In further embodiments, the compounds of the present invention do not directly target the MPT pore. In additional embodiments, the compounds of the present invention do not generate substantial ROS in the subcellular S15 fraction (e.g., cytosol; microsomes). In even further embodiments, the compounds of the present invention do not stimulate ROS if mitochondria are in state 4 respiration.

MRC complexes I-III are the primary sources of ROS within mitochondria. In some embodiments, the primary source of an increase in cellular ROS levels resulting from the compounds of the present invention emanates from these complexes as a result of inhibiting the $F_1F_0$-ATPase. Indeed, in still further embodiments, the present invention inhibits ATPase activity of bovine sub-mitochondrial particles (hereinafter SMPs). In particularly preferred embodiments, the compounds of the present invention bind to the OSCP component of the $F_1F_0$-ATPase.

Oligomycin is a macrolide natural product that binds to the $F_1F_0$-ATPase, induces a state 3 to 4 transition, and as a result, generates ROS (e.g., $O_2$). In some embodiments, the compounds of the present invention bind the OSCP component of the $F_1F_0$-ATPase. In some embodiments, the compounds of the present invention bind the junction between the OSCP and the $F_1$ subunit of the $F_1F_0$-ATPase. In some embodiments, the compounds of the present invention bind the $F_1$ subunit. In certain embodiments, screening assays of the present invention permit detection of binding partners of the OSCP, $F_1$, or OSCP/$F_1$ junction. OSCP is an intrinsically fluorescent protein. In certain embodiments, titrating a solution of test compounds of the present invention into an *E. Coli* sample overexpressing OSCP and/or an OSCP analog attached with a fluorescent label results in quenching of the intrinsic OSCP fluorescence. In other embodiments, fluorescent or radioactive test compounds can be used in direct binding assays. In other embodiments, competition binding experiments can be conducted. In this type of assay, test compounds are assessed for their ability to compete with a known binding compound for binding to, for example, the OSCP. In some embodiments, the compounds of the present invention cause an increase in cellular ROS levels and apoptosis in cells through regulation of the OSCP gene (e.g., altering expression of the OSCP gene). In further embodiments, the present invention functions by altering the molecular motions of the ATPase motor.

II. 1,4-Benzodiazepinone Compounds

In one aspect, the invention provides a family of compounds represented by Formula I:

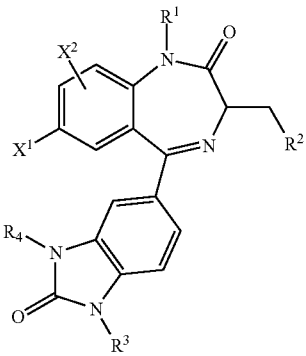

I including a pharmaceutically acceptable salt thereof, wherein:

$X^1$ is Cl or F;

$X^2$ is hydrogen, halogen, hydroxyl, methoxy, ethoxy, methyl, or ethyl;

$R^1$ is hydrogen, $C_1$-$C_3$ alkyl, hydroxyethyl, or hydroxypropyl;

$R^2$ is

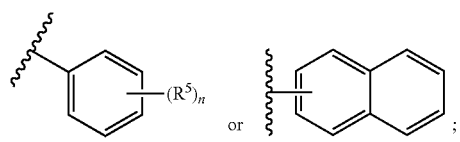

$R^3$ and $R^4$ are independently hydrogen, $C_1$-$C_5$ alkyl, or Z; provided that both $R^3$ and $R^4$ are not hydrogen, and provided that both $R^3$ and $R^4$ are not Z;

$R^5$ represents independently for each occurrence halogen, trifluoromethyl, or $C_1$-$C_5$ alkyl;

$R^6$ represents independently for each occurrence hydrogen or $C_1$-$C_5$ alkyl;

Z is $C_1$-$C_4$alkylene-$CO_2R^6$, $C_1$-$C_4$alkylene-C(O)N($R^6$)$_2$, or $C_1$-$C_4$alkyl substituted with —O$R^6$;

n is 1 or 2; and the stereochemical configuration at a stereocenter in a compound represented by Formula I is R, S, or a mixture thereof.

In certain embodiments, $X^1$ is Cl. In certain other embodiments, $X^1$ is F. In certain embodiments, $X^2$ is hydrogen or halogen. In certain other embodiments, $X^2$ is hydrogen. In certain embodiments, $R^1$ is hydrogen. In certain other embodiments, $R^1$ is $C_1$-$C_3$ alkyl. In certain embodiments, $R^2$ is

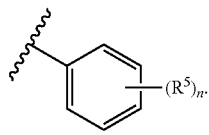

In certain other embodiments, $R^2$ is

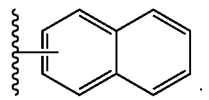

In certain embodiments, $R^3$ and $R^4$ are independently hydrogen or $C_1$-$C_5$ alkyl; provided that both $R^3$ and $R^4$ are not hydrogen. In certain other embodiments, $R^3$ is hydrogen; and $R^4$ is $C_1$-$C_5$ alkyl or Z. In certain other embodiments, $R^3$ is $C_1$-$C_5$ alkyl or Z; and $R^4$ is hydrogen. In certain other embodiments, $R^3$ is hydrogen; and $R^4$ is methyl, ethyl or propyl. In certain other embodiments, $R^3$ is methyl, ethyl or propyl; and $R^4$ is hydrogen. In certain embodiments, $R^5$ is halogen. In certain other embodiments, $R^5$ is chloro. In certain other embodiments, $R^5$ is chloro or fluoro. In certain embodiments, n is 1. In certain embodiments, n is 2.

In certain embodiments, the compound is represented by Formula IA:

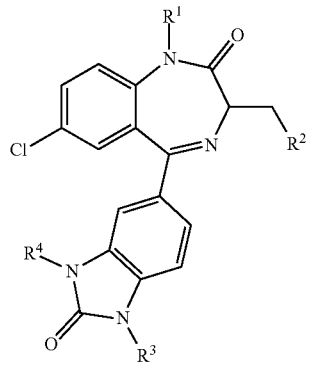

IA including a pharmaceutically acceptable salt thereof, wherein:

$R^1$ is hydrogen, methyl, or ethyl;

$R^2$ is

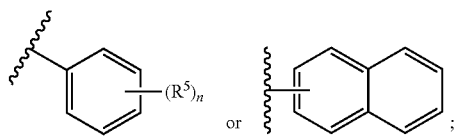

$R^3$ and $R^4$ are independently hydrogen, methyl, ethyl, propyl, butyl, or Z; provided that both $R^3$ and $R^4$ are not hydrogen, and provided that both $R^3$ and $R^4$ are not Z;

$R^5$ represents independently for each occurrence Cl or F;

Z is hydroxyethyl, hydroxylpropyl, or hydroxybutyl;

n is 1 or 2; and the stereochemical configuration at a stereocenter in a compound represented by Formula IA is R, S, or a mixture thereof In certain embodiments, $R^2$ is

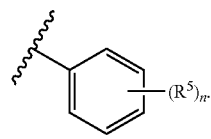

In certain embodiments, $R^3$ and $R^4$ are independently hydrogen, methyl, ethyl, or propyl; provided that both $R^3$ and $R^4$ are not hydrogen. In certain other embodiments, $R^3$ is hydrogen; and $R^4$ is methyl, ethyl or propyl. In certain other embodiments, $R^3$ is methyl, ethyl or propyl; and $R^4$ is hydrogen. In certain other embodiments, $R^5$ is Cl, and n is 1. In certain embodiments, $R^2$ is

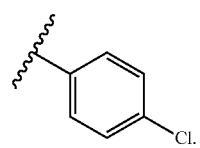 [SMILES: *c1ccc(Cl)cc1]

In certain embodiments, the compound is represented by Formula IB:

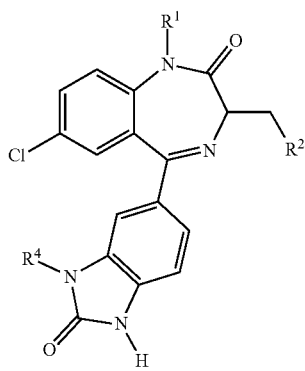

including a pharmaceutically acceptable salt thereof, wherein:

$R^1$ is hydrogen or methyl; $R^2$ is

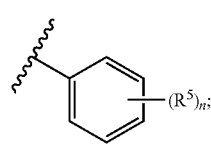

$R^4$ is methyl, ethyl, propyl, butyl, hydroxyethyl, hydroxylpropyl, or hydroxybutyl; $R^5$ represents independently for each occurrence Cl or F; n is 1 or 2; and the stereochemical configuration at a stereocenter in a compound represented by Formula IB is R, S, or a mixture thereof. In certain embodiments, $R^1$ is hydrogen and n is 1. In certain embodiments, $R^1$ is hydrogen, n is 1, and $R^4$ is methyl, ethyl, or propyl. In certain embodiments, $R^2$ is

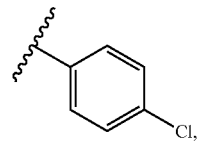

and $R^4$ is methyl, ethyl, or propyl.

In certain embodiments, the compound is represented by Formula IC:

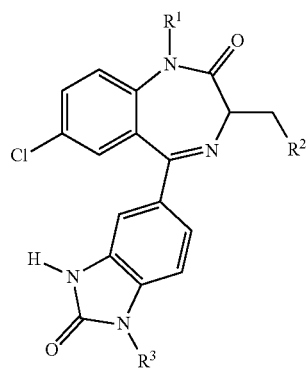

including a pharmaceutically acceptable salt thereof, wherein:

$R^1$ is hydrogen or methyl; $R^2$ is

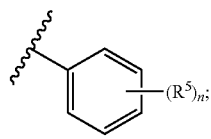

$R^3$ is methyl, ethyl, propyl, butyl, hydroxyethyl, hydroxylpropyl, or hydroxybutyl; $R^5$ represents independently for each occurrence Cl or F; n is 1 or 2; and the stereochemical configuration at a stereocenter in a compound represented by Formula IC is R, S, or a mixture thereof. In certain embodiments, $R^1$ is hydrogen and n is 1. In certain embodiments, $R^1$ is hydrogen, n is 1, and $R^3$ is methyl, ethyl, or propyl. In certain embodiments, $R^2$ is

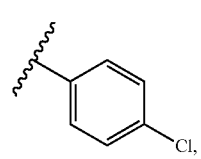 [SMILES: *c1ccc(Cl)cc1]

and $R^3$ is methyl, ethyl, or propyl.

In another aspect, the invention provides a family of compounds represented by Formula II:

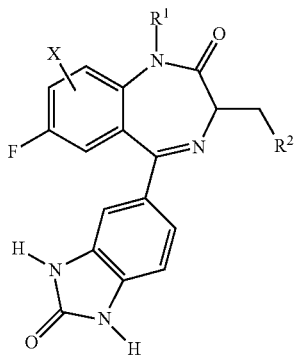

II

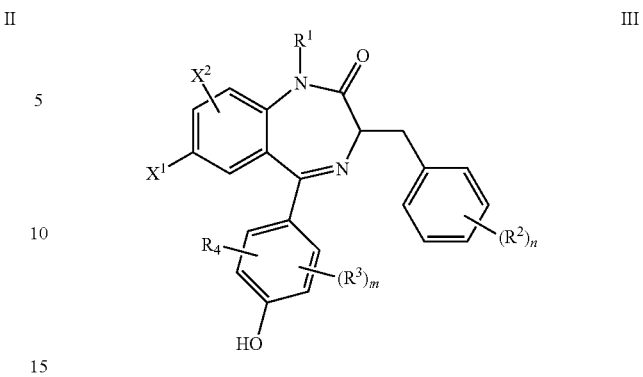

III including a pharmaceutically acceptable salt thereof, wherein:

X is hydrogen, halogen, hydroxyl, methoxy, ethoxy, methyl, or ethyl;

$R^1$ is hydrogen, $C_1$-$C_3$ alkyl, hydroxyethyl, or hydroxypropyl;

$R^2$ is

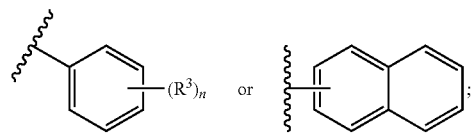

$R^3$ represents independently for each occurrence halogen, trifluoromethyl, or $C_1$-$C_5$ alkyl;

n is 1 or 2; and the stereochemical configuration at a stereocenter in a compound represented by Formula II is R, S, or a mixture thereof.

In certain embodiments, X is hydrogen. In certain embodiments, $R^1$ is hydrogen or $C_1$-$C_3$ alkyl. In certain embodiments, $R^2$ is

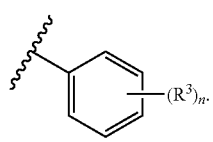

In certain other embodiments, $R^2$ is

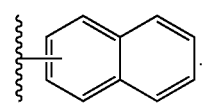

In certain embodiments, $R^3$ is halogen. In certain other embodiments, $R^3$ is Cl. In certain embodiments, $R^3$ is trifluoromethyl. In certain embodiments, n is 1. In certain other embodiments, $R^3$ represents independently for each occurrence Cl or F, and n is 2.

In another aspect, the invention provides a family of compounds represented by Formula III:

including a pharmaceutically acceptable salt thereof, wherein:

$X^1$ is Cl, F, or —$CF_3$;

$X^2$ is hydrogen, halogen, hydroxyl, methoxy, ethoxy, methyl, or ethyl;

$R^1$ is hydrogen, $C_1$-$C_3$ alkyl, hydroxyethyl, or hydroxypropyl;

$R^2$ represents independently for each occurrence halogen, trifluoromethyl, or $C_1$-$C_3$ alkyl;

$R^3$ represents independently for each occurrence $C_1$-$C_3$ alkyl, $C_1$-$C_4$alkylene-$CO_2R^5$, or $C_1$-$C_4$alkylene-C(O)N($R^5$)$_2$;

$R^4$ is hydrogen or halogen;

$R^5$ represents independently for each occurrence hydrogen or $C_1$-$C_5$ alkyl;

m and n are independently 1 or 2; and the stereochemical configuration at a stereocenter in a compound represented by Formula III is R, S, or a mixture thereof.

In certain embodiments, $X^1$ is Cl. In certain other embodiments, $X^1$ is F. In certain other embodiments, $X^1$ is —$CF_3$. In certain embodiments, $X^2$ is hydrogen. In certain other embodiments, $X^2$ is halogen. In certain embodiments, $R^1$ is hydrogen. In certain other embodiments, $R^1$ is $C_1$-$C_3$ alkyl. In certain embodiments, $R^2$ is trifluoromethyl. In certain embodiments, $R^2$ is halogen. In certain other embodiments, $R^2$ is Cl or F. In certain embodiments, $R^3$ is $C_1$-$C_3$ alkyl. In certain other embodiments, $R^3$ is methyl. In certain embodiments, $R^4$ is hydrogen. In certain other embodiments, $R^4$ is halogen. In certain other embodiments, $R^4$ is fluoro or chloro. In certain embodiments, n is 1. In certain other embodiments, n is 2. In certain embodiments, m is 1.

In certain embodiments, the invention provides a family of compounds represented by Formula IIIA:

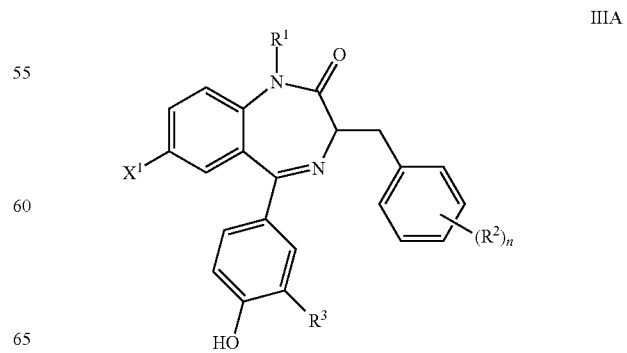

IIIA including a pharmaceutically acceptable salt thereof, wherein: $X^1$ is Cl, F, or $CF_3$; $R^1$ is hydrogen, $C_1$-$C_3$ alkyl, hydroxyethyl, or hydroxypropyl; $R^2$ represents independently for each occurrence halogen or trifluoromethyl; $R^3$ is $C_1$-$C_3$ alkyl; n is 1 or 2; and the stereochemical configuration at a stereocenter in a compound represented by Formula IIIA is R, S, or a mixture thereof. In certain embodiments, $X^1$ is Cl. In certain embodiments, $R^1$ is hydrogen or $C_1$-$C_3$ alkyl. In certain embodiments, $R^2$ is chloro or fluoro. In certain embodiments, $R^3$ is methyl.

In certain other embodiments, the compound is one of the compounds listed in Tables 1-4 herein below, or a pharmaceutically acceptable salt of said compounds. It is understood that the foregoing compounds can be combined with a pharmaceutically acceptable carrier to produce a pharmaceutical composition.

TABLE 1

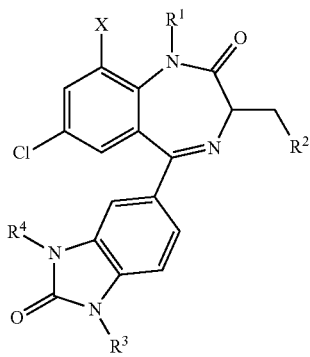

| Compound No. | X | $R^1$ | $R^2$ | $R^3$ | $R^4$ |
|---|---|---|---|---|---|
| I-1 | H | methyl | 2-naphthyl | H | ethyl |
| I-2 | H | H | 2-chlorophenyl | H | methyl |
| I-3 | H | H | 2-chlorophenyl | H | —CH$_2$CO$_2$H |
| I-4 | H | H | 2-chlorophenyl | H | —CH$_2$C(O)N(H)CH$_3$ |
| I-5 | H | H | 2-chlorophenyl | H | —(CH$_2$)$_3$OH |
| I-6 | H | H | 2-chlorophenyl | H | —(CH$_2$)$_2$OH |
| I-7 | H | methyl | 2-chlorophenyl | H | —(CH$_2$)$_3$OH |
| I-8 | H | —(CH$_2$)$_2$OH | 2-chlorophenyl | H | methyl |
| I-9 | —OCH$_3$ | H | 2-chlorophenyl | H | methyl |
| I-10 | —OH | H | 2-chlorophenyl | H | methyl |
| I-11 | H | methyl | 2-chlorophenyl | H | methyl |
| I-12 | F | H | 2-chlorophenyl | H | methyl |
| I-13 | H | H | 4-chlorophenyl | H | methyl |
| I-14 | H | H | 2-naphthyl | ethyl | H |
| I-15 | H | H | 2-chlorophenyl | H | methyl |
| I-16 | H | H | 2-chlorophenyl | H | —(CH$_2$)$_3$OH |
| I-17 | H | H | 2-chloro-4-fluorophenyl | H | methyl |
| I-18 | H | H | 2-fluoro-4-chlorophenyl | H | methyl |
| I-19 | H | H | 4-chlorophenyl | H | methyl |
| I-20 | H | H | 4-cyclopropyl-phenyl | H | methyl |
| I-21 | H | H | 2-chloro-4-fluorophenyl | H | —(CH$_2$)$_3$OH |
| I-22 | H | H | 2-fluoro-4-chlorophenyl | H | —(CH$_2$)$_3$OH |
| I-23 | H | H | 4-chlorophenyl | H | —(CH$_2$)$_3$OH |
| I-24 | H | H | 4-cyclopropyl-phenyl | H | —(CH$_2$)$_3$OH |
| I-25 | H | H | 2-chloro-4-fluorophenyl | methyl | H |
| I-26 | H | H | 2-fluoro-4-chlorophenyl | methyl | H |
| I-27 | H | H | 4-chlorophenyl | methyl | H |
| I-28 | H | H | 4-cyclopropyl-phenyl | methyl | H |
| I-29 | OH | H | 2-trifluoromethyl-phenyl | methyl | H |
| I-30 | H | H | 2-trifluoromethyl-phenyl | methyl | H |
| I-31 | H | H | 2-trifluoromethyl-phenyl | H | methyl |
| I-32 | H | H | 4-chlorophenyl | —(CH$_2$)$_3$CH$_3$ | H |
| I-33 | H | —(CH$_2$)$_2$OH | 4-chlorophenyl | methyl | H |
| I-34 | —OCH$_3$ | H | 4-chlorophenyl | methyl | H |
| I-35 | —OH | H | 4-chlorophenyl | methyl | H |
| I-36 | F | H | 4-chlorophenyl | methyl | H |
| I-37 | H | H | 2-chlorophenyl | H | methyl |

TABLE 1-continued

| Compound No. | X | R¹ | R² | R³ | R⁴ |
|---|---|---|---|---|---|
| I-38 | H | H | 3-chlorophenyl | H | methyl |
| I-39 | H | H | 2,3-dichlorophenyl | H | methyl |
| I-40 | H | H | 2,4-dichlorophenyl | H | methyl |
| I-41 | H | H | 2,6-dichlorophenyl | H | methyl |
| I-42 | H | methyl | 2-chlorophenyl | H | methyl |
| I-43 | H | methyl | 3-chlorophenyl | H | methyl |
| I-44 | H | methyl | 2,3-dichlorophenyl | H | methyl |
| I-45 | H | methyl | 2,4-dichlorophenyl | H | methyl |
| I-46 | H | methyl | 2,6-dichlorophenyl | H | methyl |
| I-47 | H | H | 2-chlorophenyl | methyl | H |
| I-48 | H | H | 3-chlorophenyl | methyl | H |
| I-49 | H | H | 2,3-dichlorophenyl | methyl | H |
| I-50 | H | H | 2,4-dichlorophenyl | methyl | H |
| I-51 | H | H | 2,6-dichlorophenyl | methyl | H |
| I-52 | H | methyl | 2-chlorophenyl | methyl | H |
| I-53 | H | methyl | 3-chlorophenyl | methyl | H |
| I-54 | H | methyl | 2,3-dichlorophenyl | methyl | H |
| I-55 | H | methyl | 2,4-dichlorophenyl | methyl | H |
| I-56 | H | methyl | 2,6-dichlorophenyl | methyl | H |
| I-57 | H | H | 2-fluorophenyl | methyl | H |
| I-58 | H | H | 3-fluorophenyl | methyl | H |
| I-59 | H | H | 2,3-difluorophenyl | methyl | H |
| I-60 | H | H | 2,4-difluorophenyl | methyl | H |
| I-61 | H | H | 2,6-difluorophenyl | methyl | H |
| I-62 | H | methyl | 2-fluorophenyl | methyl | H |
| I-63 | H | methyl | 3-fluorophenyl | methyl | H |
| I-64 | H | methyl | 2,3-difluorophenyl | methyl | H |
| I-65 | H | methyl | 2,4-difluorophenyl | methyl | H |
| I-66 | H | methyl | 2,6-difluorophenyl | methyl | H |
| I-67 | F | methyl | 2-naphthyl | H | methyl |
| I-68 | F | H | 2-chlorophenyl | H | methyl |
| I-69 | F | H | 2-fluorophenyl | H | —CH$_2$CO$_2$H |
| I-70 | F | H | 2-bromophenyl | H | —CH$_2$C(O)N(H)CH$_3$ |
| I-71 | F | H | 2-fluorophenyl | H | —(CH$_2$)$_3$OH |
| I-72 | F | H | 2-chloro-4-fluorophenyl | H | —(CH$_2$)$_2$OH |
| I-73 | F | —(CH$_2$)$_2$OH | 2-chlorophenyl | methyl | H |
| I-74 | F | ethyl | 2-naphthyl | methyl | H |
| I-75 | F | H | 4-chlorophenyl | methyl | H |
| I-76 | OH | methyl | 2-trifluoromethyl-phenyl | H | methyl |

TABLE 1-continued

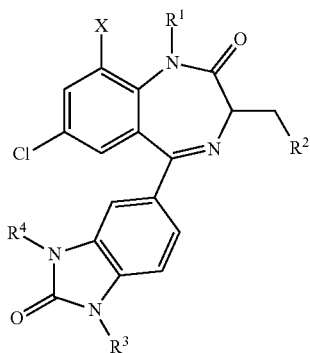

| Compound No. | X | R¹ | R² | R³ | R⁴ |
| --- | --- | --- | --- | --- | --- |
| I-77 | OH | ethyl | 2-naphthyl | methyl | H |
| I-78 | OH | H | 4-chlorophenyl | methyl | H |
| I-79 | OH | H | 4-chlorophenyl | methyl | H |
| I-80 | OH | methyl | 4-chlorophenyl | methyl | H |
| I-81 | H | ethyl | 2-naphthyl | H | methyl |
| I-82 | H | methyl | 2-naphthyl | H | methyl |
| I-83 | H | ethyl | 2-naphthyl | H | ethyl |
| I-84 | H | methyl | 2-naphthyl | H | —(CH₂)₃OH |
| I-85 | H | methyl | 2-naphthyl | H | —CH₂CO₂H |

TABLE 2

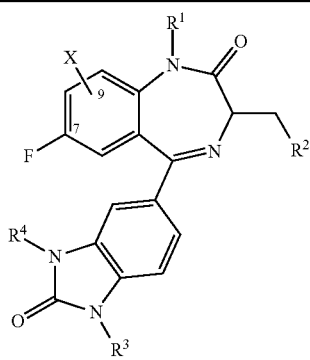

| Compound No. | X | R¹ | R² | R³ | R⁴ |
| --- | --- | --- | --- | --- | --- |
| II-1 | 9-H | H | 2-chlorophenyl | H | H |
| II-2 | 9-H | H | 2-chloro-4-fluorophenyl | H | methyl |
| II-3 | 9-H | H | 2-fluoro-4-chlorophenyl | H | methyl |
| II-4 | 9-H | H | 4-chlorophenyl | H | methyl |
| II-5 | 9-H | H | 4-cyclopropyl-phenyl | H | methyl |
| II-6 | 9-H | H | 2-chloro-4-fluorophenyl | H | —(CH₂)₃OH |
| II-7 | 9-H | H | 2-fluoro-4-chlorophenyl | H | —(CH₂)₃OH |
| II-8 | 9-H | H | 4-chlorophenyl | H | —(CH₂)₃OH |
| II-9 | 9-H | H | 4-cyclopropyl-phenyl | H | —(CH₂)₃OH |
| II-10 | 9-H | H | 2-chloro-4-fluorophenyl | methyl | H |

TABLE 2-continued

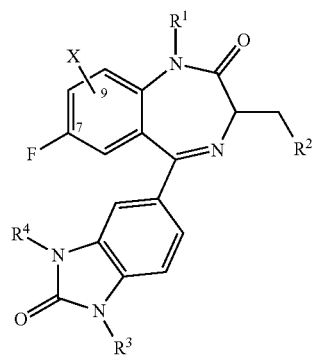

| Compound No. | X | $R^1$ | $R^2$ | $R^3$ | $R^4$ |
|---|---|---|---|---|---|
| II-11 | 9-H | H | 2-fluoro-4-chlorophenyl | methyl | H |
| II-12 | 9-H | H | 4-chlorophenyl | methyl | H |
| II-13 | 9-H | H | 4-cyclopropyl-phenyl | methyl | H |
| II-14 | 9-H | H | 2-trifluoromethyl-4-chlorophenyl | methyl | H |
| II-15 | 9-H | H | 2-trifluoromethyl-phenyl | H | methyl |
| II-16 | 9-H | H | 2-trifluoromethyl-phenyl | methyl | H |
| II-17 | 9-H | H | 4-chlorophenyl | —(CH$_2$)$_3$OCH$_3$ | H |
| II-18 | 9-H | —(CH$_2$)$_2$OCH$_3$ | 4-chlorophenyl | H | H |
| II-19 | 9-H | —(CH$_2$)$_3$OCH$_3$ | 4-chlorophenyl | H | H |
| II-20 | 9-H | —(CH$_2$)$_2$OCH$_3$ | 4-chlorophenyl | methyl | H |
| II-21 | 9-CH$_3$ | H | 4-chlorophenyl | methyl | H |
| II-22 | 9-F | H | 4-chlorophenyl | methyl | H |
| II-23 | 9-Cl | H | 4-chlorophenyl | methyl | H |
| II-24 | 8-F | H | 4-chlorophenyl | methyl | H |
| II-25 | 8-Cl | H | 4-chlorophenyl | methyl | H |
| II-26 | 9-H | H | 2-trifluoromethyl-4-chlorophenyl | H | H |
| II-27 | 9-H | H | 2-trifluoromethyl-phenyl | H | H |
| II-28 | 8-Cl | H | 4-chlorophenyl | H | H |
| II-29 | 9-Cl | H | 4-chlorophenyl | H | H |
| II-30 | 8-CH$_3$ | H | 4-chlorophenyl | H | H |
| II-31 | 9-H | —(CH$_2$)$_2$OCH$_3$ | 4-chlorophenyl | H | H |
| II-32 | 9-H | —(CH$_2$)$_3$OCH$_3$ | 4-chlorophenyl | H | H |
| II-33 | 9-H | —(CH$_2$)$_2$OCH$_3$ | 2-trifluoromethyl-4-chlorophenyl | H | H |
| II-34 | 9-H | —(CH$_2$)$_3$OCH$_3$ | 2-trifluoromethyl-4-chlorophenyl | H | H |
| II-35 | 9-H | —(CH$_2$)$_2$OCH$_3$ | 2-fluoro-4-chlorophenyl | H | H |
| II-36 | 9-H | —(CH$_2$)$_3$OCH$_3$ | 2-fluoro-4-chlorophenyl | H | H |
| II-37 | 9-H | —(CH$_2$)$_2$OCH$_3$ | 2-chloro-4-fluorophenyl | H | H |
| II-38 | 9-H | —(CH$_2$)$_3$OCH$_3$ | 2-chloro-4-fluorophenyl | H | H |
| II-39 | 9-CH$_3$ | H | 2-chloro-4-fluorophenyl | H | H |
| II-40 | 9-CH$_3$ | H | 2-chloro-4-fluorophenyl | H | methyl |

TABLE 3

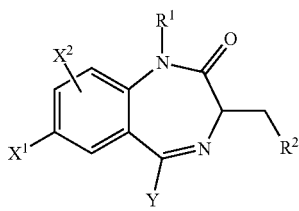

| Compound No. | X¹ | X² | R¹ | R² | Y |
|---|---|---|---|---|---|
| III-1 | Cl | H | H | 3,4-diethylphenyl | 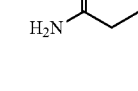 |
| III-2 | Cl | H | H | 2-chloro-5-fluoro-phenyl | 3-methyl-4-hydroxyphenyl |
| III-3 | Cl | H | H | 4-chlorophenyl | 3-methyl-4-hydroxyphenyl |
| III-4 | Cl | H | H | 2-chloro-4-fluoro-phenyl | 3-methyl-4-hydroxyphenyl |
| III-5 | Cl | H | H | 2-trifluoromethyl phenyl | 3-methyl-4-hydroxyphenyl |
| III-6 | Cl | H | H | 4-trifluoromethyl phenyl | 3-methyl-4-hydroxyphenyl |
| III-7 | Cl | H | H | 2-chlorophenyl | 3-methyl-4-hydroxyphenyl |
| III-8 | Cl | H | H | 2-fluoro-4-chlorophenyl | 3-methyl-4-hydroxyphenyl |
| III-9 | Cl | H | H | 3-fluoro-4-chlorophenyl | 3-methyl-4-hydroxyphenyl |
| III-10 | Cl | 8-fluoro | H | 3-fluoro-4-chlorophenyl | 3-methyl-4-hydroxyphenyl |
| III-11 | Cl | H | H | 4-chlorophenyl | 2-fluoro-3-methyl-4-hydroxyphenyl |
| III-12 | Cl | H | H | 4-chlorophenyl | 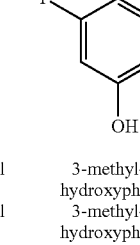 |
| III-13 | Cl | 9-methoxy | H | 4-chlorophenyl | 3-methyl-4-hydroxyphenyl |
| III-14 | Cl | 9-ethoxy | H | 4-chlorophenyl | 3-methyl-4-hydroxyphenyl |
| III-15 | Cl | 9-hydroxy | H | 4-chlorophenyl | 3-methyl-4-hydroxyphenyl |
| III-16 | Cl | 9-fluoro | H | 4-chlorophenyl | 3-methyl-4-hydroxyphenyl |
| III-17 | Cl | H | methyl | 2-chloro-5-fluoro-phenyl | 3-methyl-4-hydroxyphenyl |
| III-18 | Cl | H | methyl | 4-chlorophenyl | 3-methyl-4-hydroxyphenyl |
| III-19 | Cl | H | methyl | 2-chloro-4-fluoro-phenyl | 3-methyl-4-hydroxyphenyl |
| III-20 | Cl | H | methyl | 2-trifluoromethyl phenyl | 3-methyl-4-hydroxyphenyl |
| III-21 | Cl | H | methyl | 4-trifluoromethyl phenyl | 3-methyl-4-hydroxyphenyl |
| III-22 | Cl | H | methyl | 2-chlorophenyl | 3-methyl-4-hydroxyphenyl |
| III-23 | Cl | H | methyl | 2-fluoro-4-chlorophenyl | 3-methyl-4-hydroxyphenyl |
| III-24 | Cl | H | methyl | 3-fluoro-4-chlorophenyl | 3-methyl-4-hydroxyphenyl |
| III-25 | Cl | H | methyl | 2-chloro-5-fluoro-phenyl | 3,5-dimethyl-4-hydroxyphenyl |
| III-26 | Cl | H | methyl | 4-chlorophenyl | 3,5-dimethyl-4-hydroxyphenyl |
| III-27 | Cl | H | methyl | 2-chloro-4-fluoro-phenyl | 3,5-dimethyl-4-hydroxyphenyl |
| III-28 | Cl | H | methyl | 2-trifluoromethyl phenyl | 3,5-dimethyl-4-hydroxyphenyl |
| III-29 | Cl | H | methyl | 4-trifluoromethyl phenyl | 3,5-dimethyl-4-hydroxyphenyl |
| III-30 | Cl | H | methyl | 2-chlorophenyl | 3,5-dimethyl-4-hydroxyphenyl |
| III-31 | Cl | H | methyl | 2-fluoro-4-chlorophenyl | 3,5-dimethyl-4-hydroxyphenyl |
| III-32 | Cl | H | methyl | 3-fluoro-4-chlorophenyl | 3,5-dimethyl-4-hydroxyphenyl |
| III-33 | Cl | F | methyl | 2-chloro-5-fluoro-phenyl | 3-methyl-4-hydroxyphenyl |
| III-34 | Cl | F | methyl | 4-chlorophenyl | 3-methyl-4-hydroxyphenyl |
| III-35 | Cl | F | methyl | 2-chloro-4-fluoro-phenyl | 3-methyl-4-hydroxyphenyl |
| III-36 | Cl | F | methyl | 2-trifluoromethyl phenyl | 3-methyl-4-hydroxyphenyl |
| III-37 | Cl | F | methyl | 4-trifluoromethyl phenyl | 3-methyl-4-hydroxyphenyl |
| III-38 | Cl | F | methyl | 2-chlorophenyl | 3-methyl-4-hydroxyphenyl |
| III-39 | Cl | F | H | 2-chloro-5-fluoro-phenyl | 3-methyl-4-hydroxyphenyl |
| III-40 | Cl | F | H | 4-chlorophenyl | 3-methyl-4-hydroxyphenyl |
| III-41 | Cl | F | H | 2-chloro-4-fluoro-phenyl | 3-methyl-4-hydroxyphenyl |
| III-42 | Cl | H | methyl | 2-trifluoromethyl-phenyl | 3-methyl-4-hydroxyphenyl |
| III-43 | Cl | H | methyl | 2-trifluoromethyl-phenyl | 3-methyl-4-hydroxyphenyl |
| III-44 | Cl | H | methyl | 2-trifluoromethyl-phenyl | 3,5-dimethyl-4-hydroxyphenyl |
| III-45 | Cl | H | methyl | 2-trifluoromethyl-phenyl | 3,5-dimethyl-4-hydroxyphenyl |
| III-46 | F | H | methyl | 2-trifluoromethyl-phenyl | 3-methyl-4-hydroxyphenyl |
| III-47 | F | H | methyl | 2-trifluoromethyl-phenyl | 3-methyl-4-hydroxyphenyl |
| III-48 | F | H | methyl | 2-trifluoromethyl-phenyl | 3,5-dimethyl-4-hydroxyphenyl |
| III-49 | F | H | methyl | 2-trifluoromethyl-phenyl | 3,5-dimethyl-4-hydroxyphenyl |
| III-50 | Cl | H | H | 2-fluoro-4-chlorophenyl | 4-hydroxyphenyl |
| III-51 | Cl | H | H | 2-fluoro-3-chlorophenyl | 4-hydroxyphenyl |
| III-52 | Cl | H | H | 2-fluoro-5-chlorophenyl | 4-hydroxyphenyl |
| III-53 | Cl | H | H | 2-fluoro-6-chlorophenyl | 4-hydroxyphenyl |
| III-54 | Cl | H | H | 2-chloro-4-fluorophenyl | 4-hydroxyphenyl |
| III-55 | Cl | H | H | 3-chloro-4-fluorophenyl | 4-hydroxyphenyl |
| III-56 | Cl | H | methyl | 2-fluoro-4-chlorophenyl | 4-hydroxyphenyl |
| III-57 | Cl | H | methyl | 2-fluoro-3-chlorophenyl | 4-hydroxyphenyl |

TABLE 3-continued

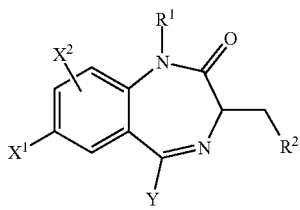

| Compound No. | X¹ | X² | R¹ | R² | Y |
|---|---|---|---|---|---|
| III-58 | Cl | H | methyl | 2-fluoro-5-chlorophenyl | 4-hydroxyphenyl |
| III-59 | Cl | H | methyl | 2-fluoro-6-chlorophenyl | 4-hydroxyphenyl |
| III-60 | Cl | H | methyl | 2-chloro-4-fluorophenyl | 4-hydroxyphenyl |
| III-61 | Cl | H | methyl | 3-chloro-4-fluorophenyl | 4-hydroxyphenyl |

In certain embodiments, the invention provides enantiomerically pure compounds. Exemplary enantiomerically pure compounds are provided in Table 4 below.

TABLE 4

| Compound No. | Compound Structure |
|---|---|
| IV-1 | 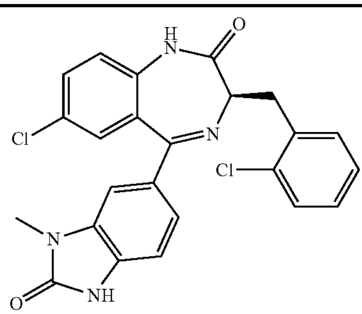 |
| IV-2 | 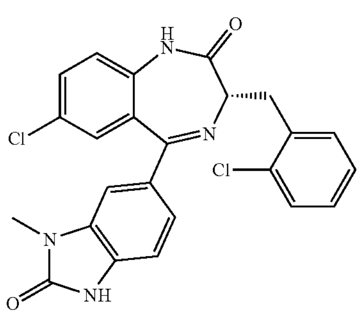 [SMILES: Cn1c(=O)[nH]c2ccc(C3=N[C@@H](Cc4ccccc4Cl)C(=O)Nc4ccc(Cl)cc43)cc21] |
| IV-3 | 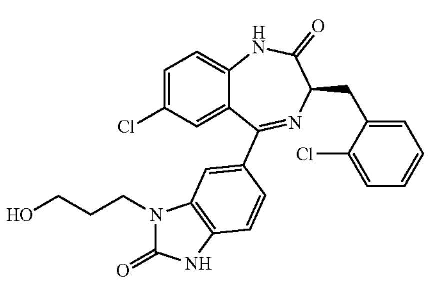 [SMILES: O=C1Nc2ccc(Cl)cc2C(c2ccc3[nH]c(=O)n(CCCO)c3c2)=N[C@@H]1Cc1ccccc1Cl] |

TABLE 4-continued

| Compound No. | Compound Structure |
|---|---|
| IV-4 | 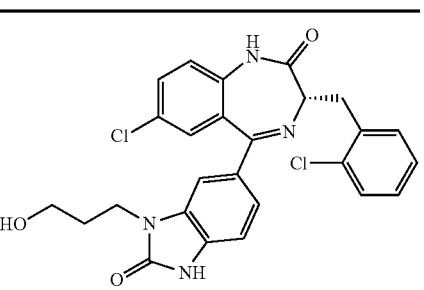 |
| IV-5 | 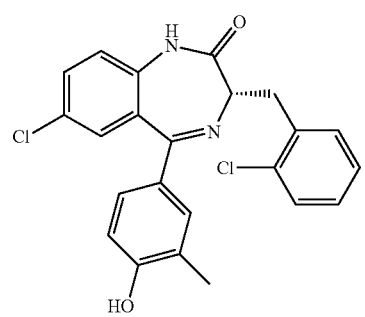 [SMILES: Cc1cc(C2=N[C@@H](Cc3ccccc3Cl)C(=O)Nc3ccc(Cl)cc32)ccc1O] |
| IV-6 | 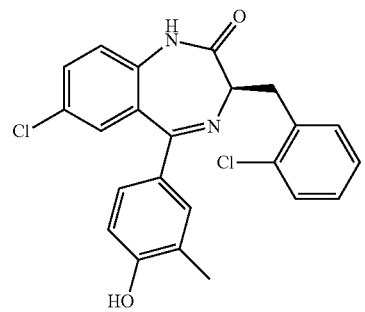 [SMILES: Cc1cc(C2=N[C@H](Cc3ccccc3Cl)C(=O)Nc3ccc(Cl)cc32)ccc1O] |
| IV-7 | 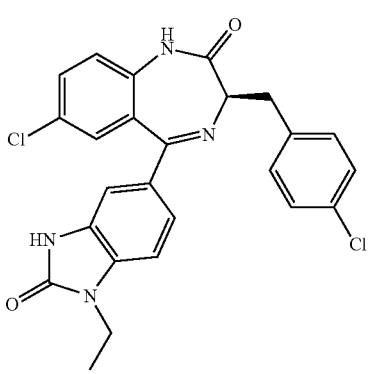 [SMILES: CCn1c(=O)[nH]c2cc(C3=N[C@H](Cc4ccc(Cl)cc4)C(=O)Nc4ccc(Cl)cc43)ccc21] |

TABLE 4-continued

| Compound No. | Compound Structure |
|---|---|
| IV-8 | 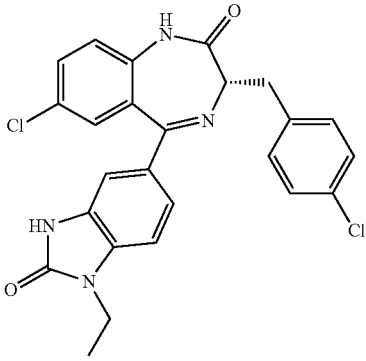 [SMILES: CCn1c(=O)[nH]c2cc(C3=N[C@@H](Cc4ccc(Cl)cc4)C(=O)Nc4ccc(Cl)cc43)ccc21] |
| IV-9 | 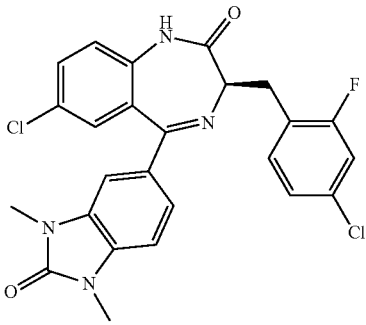 [SMILES: Cn1c(=O)n(C)c2cc(C3=N[C@H](Cc4ccc(Cl)cc4F)C(=O)Nc4ccc(Cl)cc43)ccc21] |
| IV-10 | 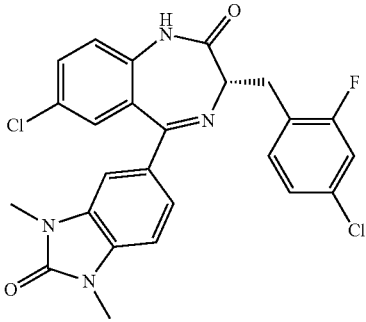 [SMILES: Cn1c(=O)n(C)c2cc(C3=N[C@@H](Cc4ccc(Cl)cc4F)C(=O)Nc4ccc(Cl)cc43)ccc21] |

Methods for preparing 1,4-benzodiazepinone compounds described herein are illustrated in the following synthetic schemes. The schemes are given for the purpose of illustrating the invention, but not for limiting the scope or spirit of the invention. Consistent with this purpose, Schemes 1-3 show exemplary methods of preparing a benzodiazepine core. The starting material, e.g., 5-chloroisatoic anhydride (A), for these routes is commercially available or can be prepared based on procedures described in the literature.

The synthetic route illustrated in Scheme 1 involves combining isatoic anhydride A and an amino acid, such as glycine, in an organic solvent such as acetic acid and applying heat to facilitate the formation of benzodiazepine C. Functional groups can be added to the N1-position of benzodiazepine C using standard alkylation chemistry described in the art. For example, amide protection of benzodiazepine C can be performed by reacting the compound with a base, such as potassium tert-butoxide, followed by a benzyl bromide, such as p-methoxy benzylbromide. Introduction of other alkyl groups at the N1-position can be performed at this stage. For example, a protected hydroxyethyl group can be installed at the N1-position by reacting benzodiazepine C with 2-bromoethyl acetate in the presence of a base. Saponification of the acetate ester provides a hydroxyethyl group at the N1-position.

Scheme 1

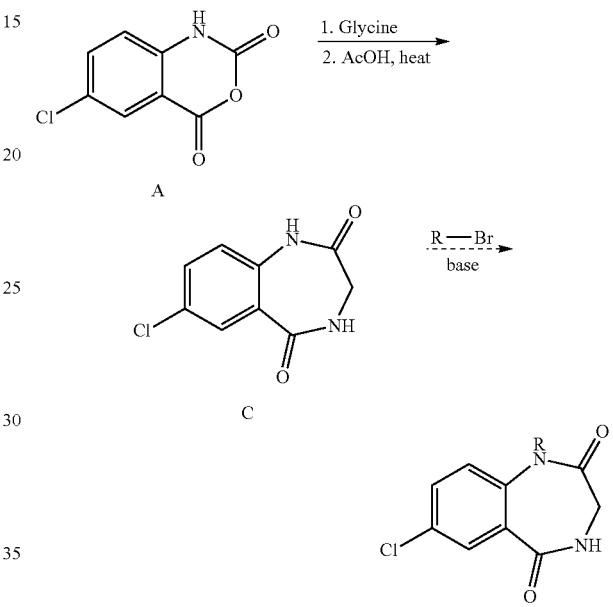

The synthetic route illustrated in Scheme 2 begins by installing a protecting group (e.g., p-methoxybenzyl (PMB)) onto the nitrogen atom of the amide, or, alternatively, alkylating the nitrogen atom to install the substituent desired at this location of the benzodiazepine final product. Alkylation of A to provide intermediate B may be carried out by treating A with an inorganic base, such as sodium carbonate or sodium hydride, and an alkyl or benzyl halide. A large number of alkyl halides and benzyl halides are known in the art and contemplated to be amenable to the synthetic route.

The second step illustrated in Scheme 2 involves combining isatoic anhydride B and an amino acid, such as glycine in an organic solvent such as acetic acid or N,N-dimethylformamide, and heating the mixture to a temperature in the range of about 60-130° C. for about 12-36 hours. Alternatively, the condensation reaction may be performed in two steps. The first step involves combining an amino acid and isatoic anhydride B in a solvent such as pyridine or acetonitrile, with or without water, containing triethylamine at a temperature in the range of about 20-100° C. for approximately 12-18 hours followed by removing the solvents in vacuo. The second step involves addition of an organic solvent, such as acetic acid or N,N-dimethylformamide, and heating the mixture to a temperature in the range of about 80-130° C. for about 12-24 hours.

Scheme 2

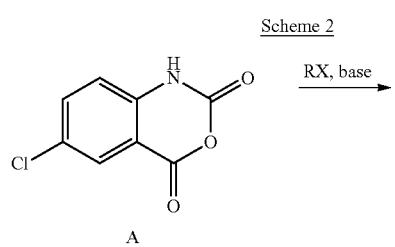

A

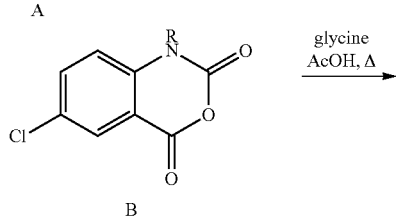

B

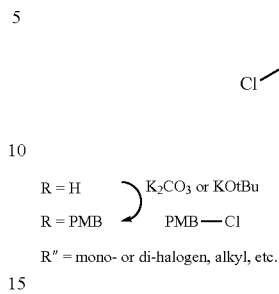

C

R = PMB or alkyl, e.g., Me.
X = halogen.

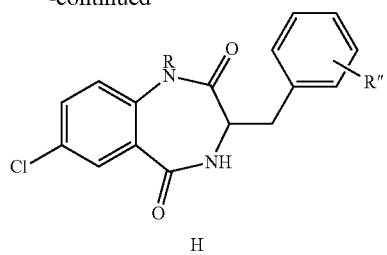

H

R = H  ⎫ K$_2$CO$_3$ or KOtBu
R = PMB ⎭   PMB—Cl

R" = mono- or di-halogen, alkyl, etc.

The synthetic route in Scheme 3 illustrates a one-step process for constructing the benzodiazepine core and installing C3-functionality. The reaction involves combining an amino acid and an isatoic anhydride, such as A, in an organic solvent such as acetic acid or N,N-dimethylformamide, and heating the mixture to a temperature in the range of about 60-130° C. for about 12-36 hours. Alternatively, the condensation reaction may be performed in two steps. The first step involves combining an amino acid, such as a phenylalanine derivative, and an isatoic anhydride, in a solvent such as pyridine or acetonitrile, with or without water, containing triethylamine at a temperature in the range of about 20-100° C. for approximately 12-18 hours followed by removing the solvents in vacuo. The second step involves adding an organic solvent, such as acetic acid or N,N-dimethylformamide, and heating the mixture to a temperature in the range of about 80-130° C. for about 12-24 hours to provide intermediate H. Notably, a protecting group can be installed at the N1-position by reacting intermediate H with a mild base and p-methoxybenzyl (PMB) chloride.

Scheme 3

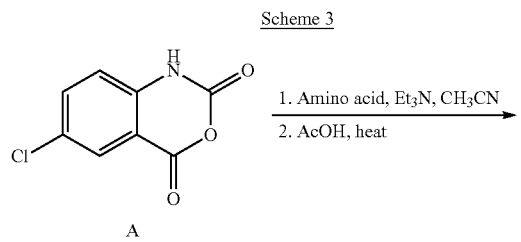

A

1. Amino acid, Et$_3$N, CH$_3$CN
2. AcOH, heat

The next phase of the synthesis involves installing the C3 and/or C5 functional groups, as illustrated in Scheme 4. Treatment of compound C with a chlorinating agent, such as phosphoryl chloride in toluene buffered with N,N-dimethylaniline, provides imidoyl chloride D. This reaction is generally performed at elevated temperature (e.g. 90° C.) for several hours (e.g., 4-18 hours). Other chlorinating agents are known in the art and are contemplated to be amenable to the synthetic route.

Compound G can be prepared from compound D using either of the two synthetic strategies shown in Scheme 4. In the first approach, compound D is treated with a strong base, e.g., potassium tert-butoxide, and then a benzyl halide, to provide intermediate F. Imidoyl chloride F may be converted to compound G using Suzuki cross-coupling conditions employing a boronic acid or boronate ester coupling partner in the presence of an appropriate palladium catalyst. Exemplary Suzuki cross-coupling procedures are described by Nadin and co-workers. See Nadin et al. in *J. Org. Chem.* 2003, 68, 2844-2852. A large number of boron-containing reagents for use in Suzuki cross-coupling are known in the art and contemplated to be amenable to the synthetic route. However, boron-containing reagents that are not commercially available may be prepared from the requisite aryl halide (e.g., iodide or bromide) under standard conditions, e.g., by treatment with bis(pinacolato)diboron in hot 1,4-dioxane containing a catalytic amount of a palladium catalyst.

In the second approach, compound D is combined with a boronic acid or boronate ester coupling partner under Suzuki cross-coupling conditions to form intermediate E. Next, intermediate E is alkylated at the C3-position to introduce a C3-aralkyl group. The alkylation step is carried out by treating intermediate E with a base, e.g., potassium tert-butoxide, at reduced temperature, e.g., −78° C. to −20° C., followed by addition of a benzyl halide. A large number of benzyl halides are known in the art and contemplated to be amenable to the synthetic route. However, benzyl halides that are not commercially available may be prepared by one of several routes that will be familiar to one skilled in the art of organic synthesis: for example, reduction of a commercially available carboxylic acid (e.g., reduction using lithium aluminum hydride), formylation of an appropriate aromatic compound followed by reduction and conversion of the resulting alcohol to a halide in one step or two steps, such as via a sulfonate ester.

Scheme 4

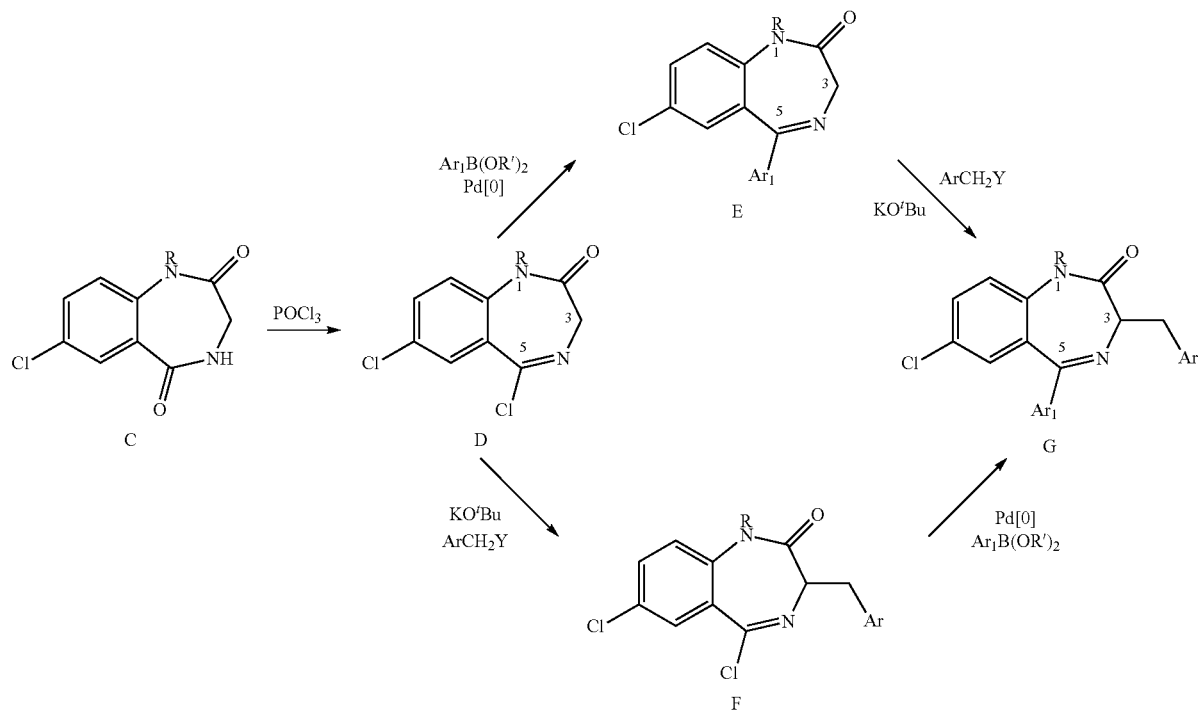

R = PMB or alkyl, e.g., Me.
R' = H or alkyl.
Y is a leaving group, e.g., Br or I.

The $Ar_1$ group installed at the C5-position during palladium-catalyzed cross coupling may be the substituent which appears in the final product, or it may be a precursor to the substituent at the C5-position in the final product. Scheme 5 illustrates preparation of an aryl boronic acid for use in a palladium-catalyzed cross coupling reaction to install the $Ar_1$ group, where the installed $Ar_1$ group serves as a precursor to the C5-substituent in the final product. The required Suzuki coupling partner (boronate or boronic acid) can be prepared from readily available aryl bromides, such as 4-bromo-2-fluoro-1-nitrobenzene and 4-bromo-1-fluoro-2-nitrobenzene. Displacement of the fluorine atom with an alkyl amine occurs under $S_NAr$ conditions according to procedures described in the literature, and borylation at the bromine position can be performed using bis(pinacolato)diboron and a palladium catalyst according to standard conditions.

Scheme 5

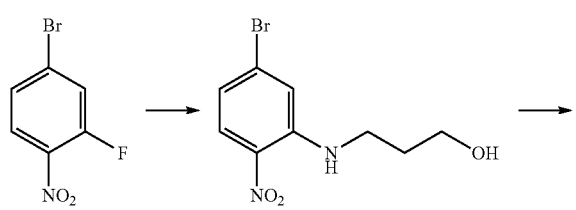

-continued

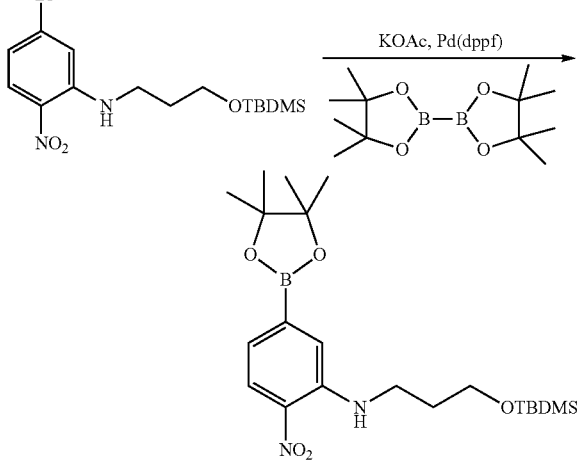

Additional description of starting materials and synthetic procedures for preparing aryl boronate ester compounds are provided by Ishiyama et al. in J. Org. Chem. (1995) Vol. 60, page 7508, and GB 1363735. For example, 5-bromo-1H-benzo[d]imidazol-2(3H)-one can be prepared according to procedures in GB 1363735, and this bromobenzimidazolone can be converted to a boronate ester.

Scheme 6 illustrates installation of an $Ar_1$ group at the C5-position and conversion of the $Ar_1$ group to the C5-substituent that appears in the final product. A palladium-catalyzed cross-coupling reaction (e.g., Suzuki Reaction) is used to install the C5 aryl group onto the benzodiazepine core.

Reduction of the nitro group to an amine using a reducing metal such as iron, or other standard nitro reducing conditions, is followed by cyclic urea formation using triphosgene or a related carbonyl donor reagent such as carbonyl-1,1'-diimidazole. A final deprotection step can be used to remove the para-methoxybenzyl (PMB) group at N1 and the tert-butyldimethylsilyl (TBDMS) group protecting the hydroxyl group.

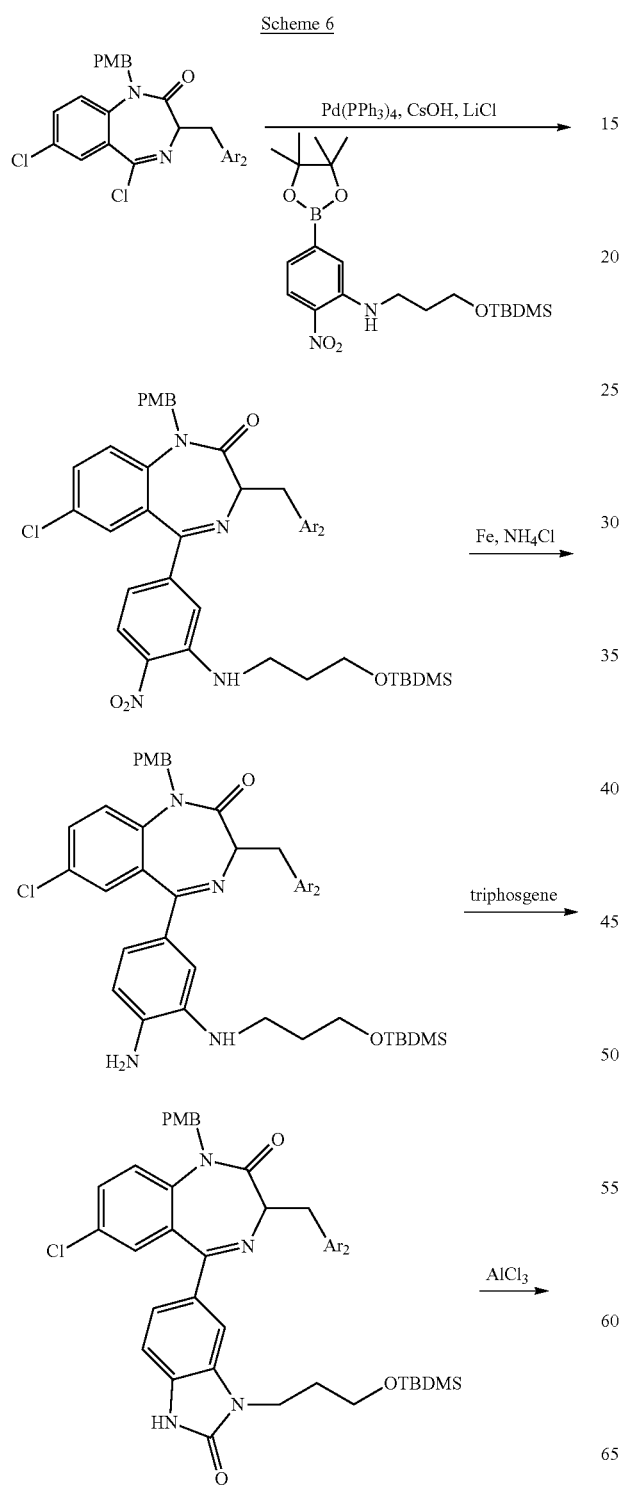

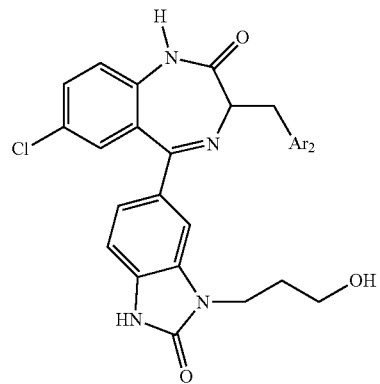

The breadth of compounds that can be prepared by the procedures described above can be further expanded by modifying the functional groups attached to the C3-aralkyl group of compound G. For example, as illustrated in Scheme 7, it is contemplated that a halogen atom attached to the aralkyl group can be converted to an alkyl group using an alkyl Grignard reagent in the presence of an iron catalyst. Procedures for carrying out reactions of this type are known in the art.

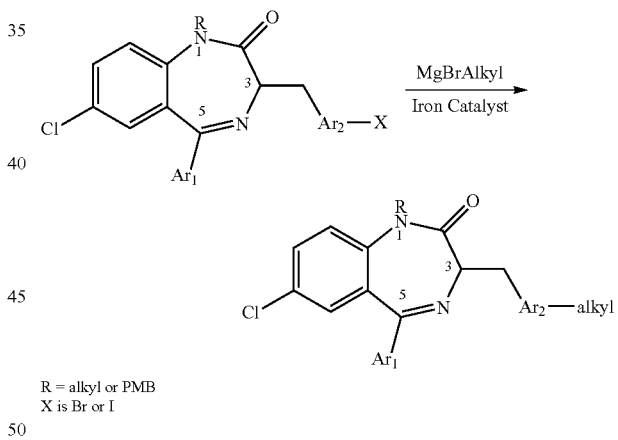

R = alkyl or PMB
X is Br or I

In situations where compound G contains one or more protecting groups, the protecting groups can be removed using standard deprotection procedures known in the art. See, for example, Greene, T. W.; Wuts, P. G. M. *Protective Groups in Organic Synthesis*, 2$^{nd}$ ed.; Wiley: New York, 1991. For instance, removal of a nitrogen protecting group such as a p-methoxybenzyl (PMB) group at the $N_1$-position may be performed using $AlCl_3$ or cerium ammonium nitrate (CAN). Similarly, demethylation or debenzylation of a phenolic ether in the $Ar_1$-group may be performed using $BBr_3$, EtSH or $AlCl_3$ to provide phenols. Representative deprotection procedures are illustrated in Scheme 8.

Scheme 8

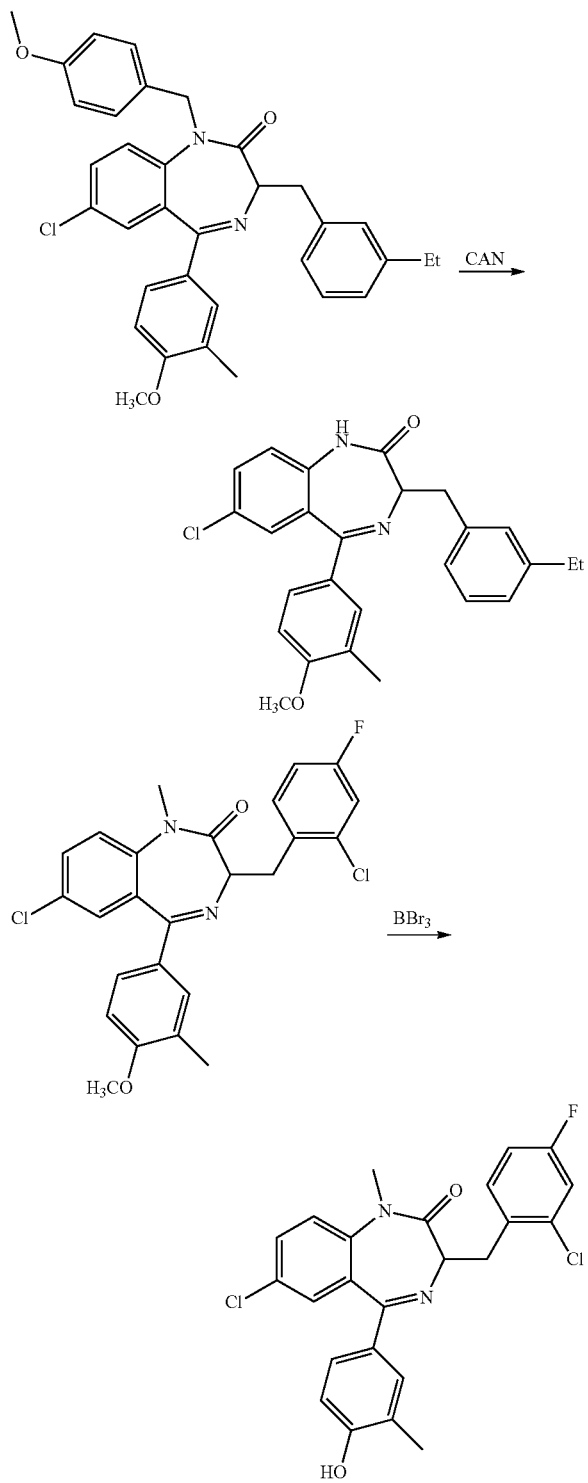

Additional synthetic procedures are described in detail in the examples below. Further, additional synthetic procedures can be found in, for example, "Comprehensive Organic Synthesis" (B. M. Trost & I. Fleming, eds., 1991-1992); Carey, F. A. and Sundberg, R. J. Advanced Organic Chemistry Part B: Reactions and Synthesis, $3^{rd}$ Ed.; Plenum Press: New York, 1990; J. March, Advanced Organic Chemistry, McGraw Hill Book Company, New York, (1992, $4^{th}$ edition); US Patent Application Publication No. 2008/112553; and International Application Publication No. WO2009/061916; each of which is hereby incorporated by reference.

III. Therapeutic Applications of 1,4-Benzodiazepinone Compounds

It is contemplated that the 1,4-benzodiazepinone compounds of Formulae I, II, and III and related 1,4-benzodiazepinone compounds, provide therapeutic benefits to patients suffering from any one or more of a number of conditions, e.g., diseases characterized by dysregulation of $F_1F_0$-ATPase activity, diseases characterized by dysregulation of necrosis and/or apoptosis processes in a cell or tissue, disease characterized by aberrant cell growth and/or hyperproliferation. The compounds described herein can also be used to treat a variety of dysregulatory disorders related to cellular death as described elsewhere herein. Additionally, the compounds described herein can be used to inhibit both ATP synthesis and hydrolysis.

A large number of diseases can be treated using the 1,4-benzodiazepinone compounds described herein. For example, the compounds described herein can be used to treat diseases characterized by dysregulation of necrosis and/or apoptosis processes in a cell or tissue, diseases characterized by aberrant cell growth and/or hyperproliferation, etc., or lupus, rheumatoid arthritis, psoriasis, graft-versus-host disease, Crohn's disease, inflammatory bowel disease, multiple sclerosis, epidermal hyperplasia, cardiovascular disease, myeloma, lymphoma, cancer, and bacterial infection. Although not wishing to be bound to a particular theory, it is believed that the compounds impart therapeutic benefit by modulating (e.g., inhibiting or promoting) the activity of the $F_1F_0$-ATPase complexes (e.g., mitochondrial $F_1F_0$-ATPase complexes) in affected cells or tissues. In some embodiments, the compositions of the present invention are used to treat immune/chronic inflammatory conditions (e.g., psoriasis, autoimmune disorders, organ-transplant rejection, and epidermal hyperplasia). In further embodiments, the compositions of the present invention are used in conjunction with stenosis therapy to treat compromised (e.g., occluded) vessels.

In certain embodiments, a composition comprising a 1,4-benzodiazepinone compound is administered under conditions (e.g., timing, dose, co-administration with other agent, mode of administration, selection of subject, use of targeting agents, etc.) that maximize desired effects directed at the $F_1F_0$-ATPase.

In certain embodiments, the invention provides a method of treating a disorder selected from the group consisting of rheumatoid arthritis, psoriasis, graft-versus-host disease, Crohn's disease, inflammatory bowel disease, multiple sclerosis, psoriasis, systemic lupus erythematosus, Celiac Sprue, idiopathic thrombocytopenic thrombotic purpura, myasthenia gravis, Sjogren's syndrome, scleroderma, ulcerative colitis, asthma, epidermal hyperplasia, cardiovascular disease, myeloma, lymphoma, cancer, and bacterial infection, comprising administering a therapeutically effective amount of a compound of Formula I, II, or III to a patient in need thereof to ameliorate a symptom of the disorder, wherein the definition of Formula I, II, and III are as provided above.

In certain embodiments, said compound is one of the compounds listed in Tables 1-4. In certain embodiments, said compound is one of the compounds listed in Table 1.

In certain embodiments, the disorder is Crohn's disease, inflammatory bowel disease, multiple sclerosis, graft-versus-host disease, lupus, rheumatoid arthritis, or psoriasis. In certain embodiments, the disorder is rheumatoid arthritis, graftversus-host disease, or inflammatory bowel disease. In certain other embodiments, the disorder is Crohn's disease, inflammatory bowel disease, multiple sclerosis, graft-versus-host disease, systemic lupus erythematosus, rheumatoid arthritis, or psoriasis. In certain other embodiments, the disorder is cardiovascular disease, myeloma, lymphoma, or cancer. In certain other embodiments, the disorder is systemic lupus erythematosus, rheumatoid arthritis, psoriasis, graft-versus-host disease, myeloma, or lymphoma. In certain other embodiments, the disorder is cardiovascular disease or cancer. In certain other embodiments, the disorder is Crohn's disease, inflammatory bowel disease, or multiple sclerosis. In certain other embodiments, the disorder is graft-versus-host disease. In further embodiments, the disorder is a bacterial infection. In certain embodiments, the patient is a human.

Additionally, the 1,4-benzodiazepinone compounds described herein can be used in combination with at least one other therapeutic agent, such as Bz-423 (a benzodiazepine compound as described in U.S. Pat. Nos. 7,144,880 and 7,125,866, U.S. patent application Ser. Nos. 12/044,589, 11/586,097, 11/585,492, 11/445,010, 11/324,419, 11/176,719, 11/110,228, 10/935,333, 10/886,450, 10/795,535, 10/634,114, 10/427, 211, 10/217,878, and 09/767,283, and U.S. Provisional Patent Nos. 60/878,519, 60/812,270, 60/802,394, 60/732,045, 60/730,711, 60/704,102, 60/686, 348, 60/641,040, 60/607,599, 60/565,788), potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents selected from ACE inhibitors, AT-1 receptor antagonists, ET receptor antagonists, dual ET/AII receptor antagonists, and vasopepsidase inhibitors, or an antiplatelet agent selected from GPIIb/IIIa blockers, $P2Y_1$ and $P2Y_{12}$ antagonists, thromboxane receptor antagonists, and aspirin) in along with a pharmaceutically-acceptable carrier or diluent in a pharmaceutical composition.

Additionally, any one or more of these compounds can be used to treat a $F_1F_0$-ATP hydrolase associated disorder (e.g., myocardial infarction, ventricular hypertrophy, coronary artery disease, non-Q wave MI, congestive heart failure, cardiac arrhythmias, unstable angina, chronic stable angina, Prinzmetal's angina, high blood pressure, intermittent claudication, peripheral occlusive arterial disease, thrombotic or thromboembolic symptoms of thromboembolic stroke, venous thrombosis, arterial thrombosis, cerebral thrombosis, pulmonary embolism, cerebral embolism, thrombophilia, disseminated intravascular coagulation, restenosis, atrial fibrillation, ventricular enlargement, atherosclerotic vascular disease, atherosclerotic plaque rupture, atherosclerotic plaque formation, transplant atherosclerosis, vascular remodeling atherosclerosis, cancer, surgery, inflammation, systematic infection, artificial surfaces, interventional cardiology, immobility, medication, pregnancy and fetal loss, and diabetic complications comprising retinopathy, nephropathy and neuropathy) in a patient.

As indicated above, the 1,4-benzodiazepinone compounds described herein can be used in the treatment of a bacterial infection. A variety of bacteria are contemplated to be susceptible to the benzodiazepinone compounds. Representative bacteria include Staphylococci species, e.g., *S. aureus*; Enterococci species, e.g., *E. faecalis* and *E. faecium*; Streptococci species, e.g., *S. pyogenes* and *S. pneumoniae; Escherichia* species, e.g., *E. coli*, including enterotoxigenic, enteropathogenic, enteroinvasive, enterohemorrhagic and enteroaggregative *E. coli* strains; *Haemophilus* species, e.g., *H. influenza*; and *Moraxella* species, e.g., *M. catarrhalis*. Other examples include *Mycobacteria* species, e.g., *M. tuberculosis, M. avian-intracellulare, M. kansasii, M. bovis, M. africanum, M. genavense, M. leprae, M. xenopi, M. simiae, M. scrofulaceum, M. malmoense, M. celatum, M. abscessus, M. chelonae, M. szulgai, M. gordonae, M. haemophilum, M. fortuni* and *M. marinum; Corynebacteria* species, e.g., *C. diphtheriae; Vibrio* species, e.g., *V. cholerae; Campylobacter* species, e.g., *C. jejuni; Helicobacter* species, e.g., *H. pylori; Pseudomonas* species, e.g., *P. aeruginosa; Legionella* species, e.g., *L. pneumophila; Treponema* species, e.g., *T. pallidum; Borrelia* species, e.g., *B. burgdorferi; Listeria* species, e.g., *L. monocytogenes; Bacillus* species, e.g., *B. cereus; Bordatella* species, e.g., *B. pertussis; Clostridium* species, e.g., *C. perfringens, C. tetani, C. difficile* and *C. botulinum; Neisseria* species, e.g., *N. meningitidis* and *N. gonorrhoeae; Chlamydia* species, e.g., *C. psittaci, C. pneumoniae* and *C. trachomatis; Rickettsia* species, e.g., *R. rickettsii* and *R. prowazekii; Shigella* species, e.g., *S. sonnei; Salmonella* species, e.g., *S. typhimurium; Yersinia* species, e.g., *Y. enterocolitica* and *Y. pseudotuberculosis; Klebsiella* species, e.g., *K. pneumoniae; Mycoplasma* species, e.g., *M. pneumoniae*; and *Trypanosoma brucei*. In certain embodiments, the benzodiazepinone compounds described herein are used to treat a subject suffering from a bacterial infection selected from the group consisting of *S. aureus, E. faecalis, E. faecium, S. pyogenes, S. pneumonia,* and *P. aeruginosa*. In certain embodiments, the benzodiazepinone compounds described herein are used to treat a subject suffering from a *Trypanosoma brucei* infection.

The antibacterial activity of the compounds described herein may be evaluated using standard assays known in the art, such as the microbroth dilution minimum inhibition concentration (MIC) assay, as further described in National Committee for Clinical Laboratory Standards. Performance Standards for Antimicrobial Susceptibility Testing; Fourteenth Informational Supplement. NCCLS document M100-S14 {ISBN 1-56238-5,6-X}. This assay may be used to determine the minimum concentration of a compound necessary to prevent visible bacterial growth in a solution. In general, the drug to be tested is serially diluted into wells, and aliquots of liquid bacterial culture are added. This mixture is incubated under appropriate conditions, and then tested for growth of the bacteria. Compounds with low or no antibiotic activity (a high MIC) will allow growth at high concentrations of compound, while compounds with high antibiotic activity will allow bacterial growth only at lower concentrations (a low MIC).

The assay uses stock bacterial culture conditions appropriate for the chosen strain of bacteria. Stock cultures from the permanent stock culture collection can be stored as frozen suspensions at −70° C. Cultures may be suspended in 10% skim milk (BD) prior to snap freezing in dry ice/ethanol and then placed in a −70° C. freezer. Cultures may be maintained on Tryptic Soy Agar containing 5% Sheep Blood at room temperature (20° C.), and each culture may be recovered from frozen form and transferred an additional time before MIC testing. Fresh plates are inoculated the day before testing, incubated overnight, and checked to confirm purity and identity.

The identity and purity of the cultures recovered from the stock culture can be confirmed to rule out the possibility of contamination. The identity of the strains may be confirmed by standard microbiological methods (See, e.g., Murray et al., Manual of Clinical Microbiology, Eighth Edition. ASM Press {ISBN 1-55581-255-4}). In general, cultures are streaked onto appropriate agar plates for visualization of purity, expected colony morphology, and hemolytic patterns. Gram stains can also be utilized. The identities are confirmed using a MicroScan WalkAway 40 SI Instrument (Dade Behring, West Sacramento, Calif.). This device utilizes an automated incubator, reader, and computer to assess for identification purposes the biochemical reactions carried out by each organism. The MicroScan WalkAway can also be used to determine a preliminary MIC, which may be confirmed using the method described below.

Frozen stock cultures may be used as the initial source of organisms for performing microbroth dilution minimum inhibition concentration (MIC) testing. Stock cultures are passed on their standard growth medium for at least 1 growth cycle (18-24 hours) prior to their use. Most bacteria may be prepared directly from agar plates in 10 mL aliquots of the appropriate broth medium. Bacterial cultures are adjusted to the opacity of a 0.5 McFarland Standard (optical density value of 0.28-0.33 on a Perkin-Elmer Lambda EZ150 Spectrophotometer, Wellesley, Mass., set at a wavelength of 600 nm). The adjusted cultures are then diluted 400 fold (0.25 mL inoculum+100 mL broth) in growth media to produce a starting suspension of approximately 5×105 colony forming units (CFU)/mL. Most bacterial strains may be tested in cation adjusted Mueller Hinton Broth (CAMHB).

Test compounds ("drugs") are solubilized in a solvent suitable for the assay, such as DMSO. Drug stock solutions may be prepared on the day of testing. Microbroth dilution stock plates may be prepared in two dilution series, 64 to 0.06 µg drug/mL and 0.25 to 0.00025 µg drug/mL. For the high concentration series, 200 µL of stock solution (2 mg/mL) is added to duplicate rows of a 96-well microtiter plate. This is used as the first well in the dilution series. Serial two-fold decremental dilutions are made using a BioMek FX robot (Beckman Coulter Inc., Fullerton, Calif.) with 10 of the remaining 11 wells, each of which will contain 100 µL of the appropriate solvent/diluent. Row 12 contains solvent/diluent only and serves as the control. For the first well of the low concentration series, 200 µL of an 8 µg/mL stock are added to duplicate rows of a 96-well plate. Serial two-fold dilutions are made as described above.

Daughter 96-well plates may be spotted (3.2 µL/well) from the stock plates listed above using the BioMek FX robot and used immediately or frozen at −70° C. until use. Aerobic organisms are inoculated (100 µL volumes) into the thawed plates using the BioMek FX robot. The inoculated plates are be placed in stacks and covered with an empty plate. These plates are then incubated for 16 to 24 hours in ambient atmosphere according to CLSI guidelines (National Committee for Clinical Laboratory Standards, Methods for Dilution, Antimicrobial Tests for Bacteria that Grow Aerobically; Approved Standard-Sixth Edition. NCCLS document M7-A6 {ISBN 1-56238-486-4}).

After inoculation and incubation, the degree of bacterial growth can be estimated visually with the aid of a Test Reading Mirror (Dynex Technologies 220 16) in a darkened room with a single light shining directly through the top of the microbroth tray. The MIC is the lowest concentration of drug that prevents macroscopically visible growth under the conditions of the test.

IV. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present invention are useful in the preparation of medicaments to treat or study a variety of conditions associated with dysregulation of cell death, aberrant cell growth and hyperproliferation.

In addition, the compounds are also useful for preparing medicaments for treating or studying other disorders wherein the effectiveness of the compounds are known or predicted. Such disorders include, but are not limited to, neurological (e.g., epilepsy) or neuromuscular disorders. The methods and techniques for preparing medicaments of a compound of the present invention are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as discussed above, together with a solid support or alternatively, together with one or more pharmaceutically acceptable carriers and optionally other therapeutic agents (e.g., those described in section III hereinabove). Each carrier should be "acceptable" in the sense that it is compatible with the other ingredients of the formulation and not injurious to the subject.

Contemplated formulations include those suitable for oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprise a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, and include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer therapeutic agents (e.g., exemplary compounds as described above) of the present invention, e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified can be administered to subjects or individuals susceptible to or at risk of developing pathological growth of target cells and correlated conditions. When the agent is administered to a subject such as a mouse, a rat or a human patient, the agent can be added to a pharmaceutically acceptable carrier and systemically or topically administered to the subject. To identify patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent. One example of an animal model is MLR/MpJ-lpr/lpr ("MLR-lpr") (available from Jackson Laboratories, Bar Harbor, Me.). MLR-lpr mice develop systemic autoimmune disease. Alternatively, other animal models can be developed by inducing tumor growth, for example, by subcutaneously inoculating nude mice with about $10^5$ to about $10^9$ hyperproliferative, cancer or target cells as defined herein. When the tumor is established, the compounds described herein are administered, for example, by subcutaneous injection around the tumor. Tumor measurements to determine reduction of tumor size are made in two dimensions using venier calipers twice a week. Other animal models may also be employed as appropriate. Such animal models for the above-described diseases and conditions are well-known in the art.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or non-aqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or by oral administration, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-administration Routes and Dosing Considerations

The invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depend on the type of condition being treated. For example, when the condition being treated is cancer, the additional agent can be a chemotherapeutic agent or radiation. When the condition being treated is an immune disorder, the additional agent can be an immunosuppressant or an anti-inflammatory agent. When the condition being treated is chronic inflammation, the additional agent can be an anti-inflammatory agent. The additional agents to be co-administered, such as anticancer, immunosuppressant, anti-inflammatory, can be any of the well-known agents in the art, including, but not limited to, those that are currently in clinical use. The determination of appropriate type and dosage of radiation treatment is also within the skill in the art or can be determined with relative ease.

Treatment of the various conditions associated with abnormal apoptosis is generally limited by the following two major factors: (1) the development of drug resistance and (2) the toxicity of known therapeutic agents. In certain cancers, for example, resistance to chemicals and radiation therapy has been shown to be associated with inhibition of apoptosis. Some therapeutic agents have deleterious side effects, including non-specific lymphotoxicity, renal and bone marrow toxicity.

The methods described herein address both these problems. Drug resistance, where increasing dosages are required to achieve therapeutic benefit, is overcome by co-administering the compounds described herein with the known agent. The compounds described herein sensitize target cells to known agents (and vice versa) and, accordingly, less of these agents are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases where drug resistance has increased the requisite dosage. When the claimed compounds are co-administered with the known agent, they reduce the dosage required which, in turn, reduces the deleterious effects.

EXAMPLES

The invention now being generally described, will be more readily understood by reference to the following examples, which are included merely for purposes of illustration of certain aspects and embodiments of the present invention, and are not intended to limit the invention.

Example 1

Representative General Procedures for Synthesis of a Benzodiazepine Core Containing a C7-Chloro Group Part I:

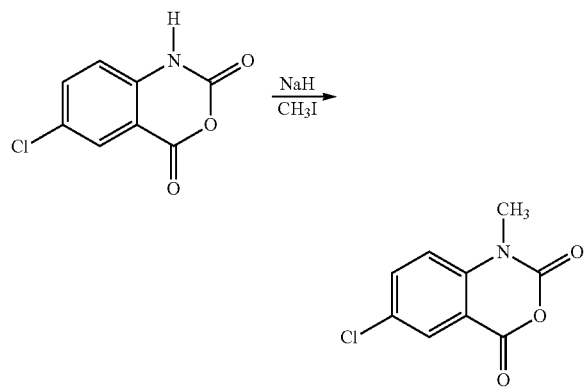

6-Chloro-1-methyl-1H-benzo[d][1,3]oxazine-2,4-dione

In a 3 L, 3 neck RBF equipped with mechanical stir, addition funnel, thermocouple and $N_2$ inlet, NaH (30.4 g) was suspended in anhydrous THF (400 mL). While stirring at room temperature, a suspension of 5-chloroisatoic anhydride in THF (400 mL) was added in portion-wise manner over 45 min. The reaction mixture was stirred for 50 min (reaction temperature went up from 18 to 28° C.). To this was added $CH_3I$ (285 g, 125 mL) over 15 min. The mixture was then stirred at 42° C. for 16 h. Because TLC showed that some unreacted starting material was still present in the reaction mixture, an additional 30 mL of $CH_3I$ was added and the reaction mixture stirred at 42° C. for an additional 3 h. Reaction mixture was cooled (RT) and quenched by the slow (40 min) addition of AcOH (55 mL). Reaction mixture was concentrated to give 275 g thick syrupy product, which was used without any further purification. $^1H$ NMR (300 MHz, $CDCl_3$) δ 3.35 (s, 3H), 7.54 (d, 1H), 7.85 (d, 1H), 7.90 (s, 1H).

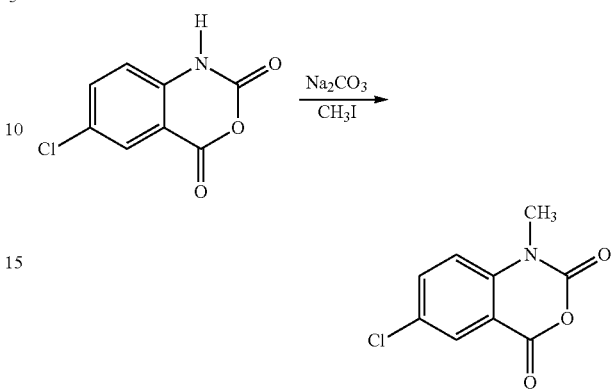

6-Chloro-1-methyl-1H-benzo[d][1,3]oxazine-2,4-dione

6-Chloro-1Hbenzo[d][1,3]oxazine-2,4-dione (22.88 g, 116 mmol) was dissolved in dimethylformamide (150 mL), and sodium carbonate (14.73 g, 139 mmol) was added. Methyl iodide (10.86 mL, 174 mmol) was then added dropwise. The reaction was stirred at room temperature overnight. Water (150 mL) was then added, and the mixture was stirred for 1 hour. The solid was collected by filtration. The impure solid was sonicated in methyl-tert-butyl ether for several minutes, and then collected by filtration yielding the product as a white solid (19.38 g, 79%). $^1HNMR$ (300 MHz, DMSO-$d_6$) δ 3.45 (s, 3H), 7.47 (d, 1H), 7.89 (dd, 1H), 7.94 (d, 1H).

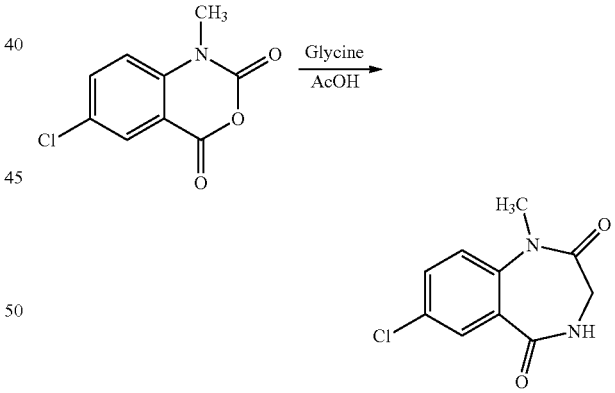

7-Chloro-1-methyl-3,4-dihydro-1H-benzo[e][1,4]diazepine-2,5-dione

In a 2 L RBF equipped with mechanical stir, condenser and $N_2$ inlet, glycine (38 g, 0.506 mol) was added to crude 6-chloro-1-methyl-1H-benzo[d][1,3]oxazine-2,4-dione (107 g, 0.506 mol) followed by the addition of AcOH (500 mL). Reaction flask was heated in a 130° C. oil bath for 7 h. Solvent was evaporated under suction with heating (50-60° C.). To the thick syrupy crude product was added 1 L of EtOAc followed by the slow addition of aqueous $NaHCO_3$ (saturated) to adjust the pH to ~7. Then 10 mL of 2 M NaOH was added to adjust the pH to ~9-10. The mixture gave a solid along with organic and aqueous layers. Solid was filtered to give product containing some impurity. Solid was partitioned between 400 mL DCM and 200 mL NaHCO$_3$ and the slurry was stirred for 20 min, then filtered to remove the insoluble impurity. The DCM layer was separated and washed with 3% NaHCO$_3$ and then brine (200 mL). The DCM layer was dried (MgSO$_4$), filtered and concentrated to give 50 g of pure product. EtOAc layer was concentrated to give 67 g of solid product with some impurity. Aqueous layer was extracted with EtOAc (2×400 mL). Combined organics were dried over Na$_2$SO$_4$, filtered and concentrated to give an additional 6.7 g of crude product. Total of 123.4 g of product was obtained, 50 g of which was very clean. $^1$H NMR (300 MHz, CDCl$_3$) δ 3.2 (s, 3H), 3.5 (m, 1 H), 3.8 (m, 1H), 7.35 (d, 1H), 7.6 (m, 2H), 8.8 (t, 1H).

Part II:

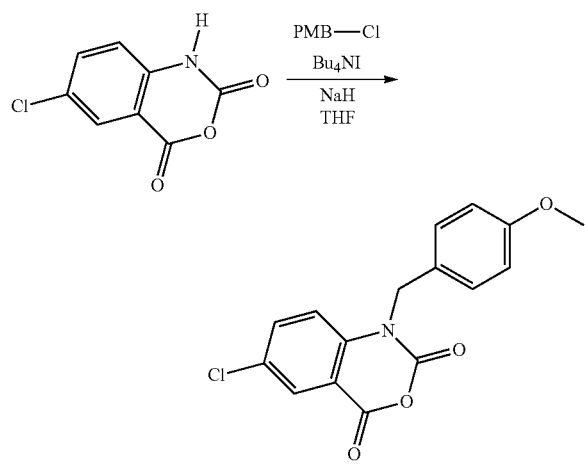

6-Chloro-1-(4-methoxybenzyl)-1H-benzo[d][1,3]
oxazine-2,4-dione

In a 3 L, 3-neck RBF equipped with mechanical stir, thermocouple and N$_2$ inlet, 90 g (0.455 mol) of 5-chloroisatoic anhydride was suspended in anhydrous THF (0.9 L). Under N$_2$, 4-methoxybenzylchloride (75 g, 0.48 mol) was added followed by the addition of tetrabutylammonium iodide (84 g, 0.23 mol). The reaction mixture was stirred for 5 min at room temperature and then 20 g (0.5 mol) of NaH was added portion-wise over 20 min (reaction temperature increased to 29° C. due to an exotherm and therefore reaction mixture was placed into water bath to keep the temperature below 30° C.). Reaction was stirred for 16 h (RT). Next day HPLC showed about 26% unreacted 5-chloroisatoic anhydride. Additional NaH (1 g) was added and the reaction mixture was heated to 32° C. and stirred for another 5 h. NMR showed that all of the starting material had been consumed. Reaction was quenched by adding 10 g of glacial acetic acid slowly followed by stirring for 30 min. Reaction mixture was filtered through celite and filter cake was washed with THF. Filtrate was concentrated to give 280 g of crude product (yellow-brown solid), which was used with no further purification. $^1$H NMR (300 MHz, DMSO-d$_6$) δ 3.8 (s, 3H), 5.25 (s, 2H), 6.8 (d, 2H), 7.2 (m, 3H), 7.75 (d, 1 H), 7.9 (d, 1H).

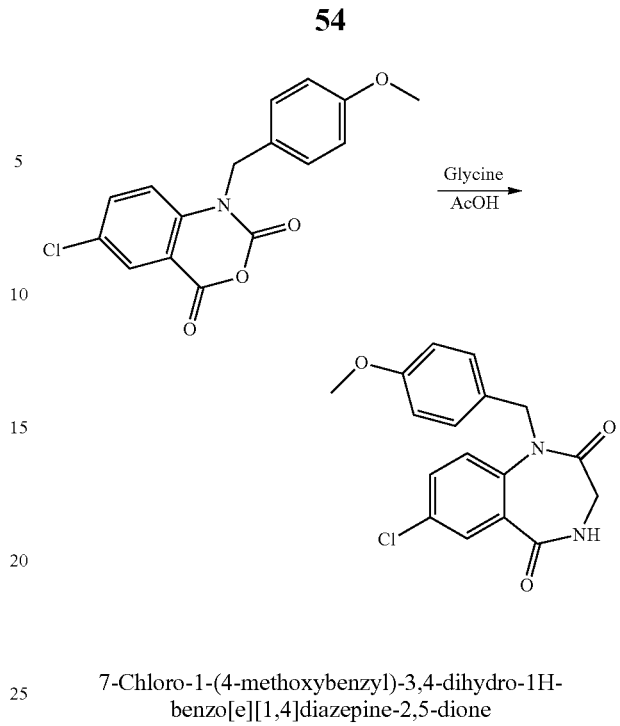

7-Chloro-1-(4-methoxybenzyl)-3,4-dihydro-1H-
benzo[e][1,4]diazepine-2,5-dione

In a 2 L RBF equipped with mechanical stir, condenser and N$_2$ inlet, glycine (34 g, 0.45 mol) was added to 6-chloro-1-(4-methoxybenzyl)-1H-benzo[d][1,3]oxazine-2,4-dione (280 g) followed by the addition of AcOH (500 mL). Reaction flask was heated in a 130° C. oil bath for 8 h. Solvent was removed on the rotary evaporator at 50-60° C. To the thick syrupy crude product was added heptane (1 L) and H$_2$O (1 L) followed by the addition of NaHCO$_3$ to adjust the pH to ~8-9. The mixture gave a solid along with organic and aqueous layers. The organic and aqueous layers were decanted and the solid was slurried with 500 mL of 5% NaHCO$_3$ solution. NaHCO$_3$ layer was decant and sticky solid was suspended in 700 mL EtOAc and 300 mL of dichloromethane (DCM). The mixture was stirred for 20 min, filtered and the filter cake was washed with 1 L of DCM. The filtrate was concentrated and residue was pass through 330 g silica gel plug using 25/75 to 75/25 EtOAC/heptane (total of 8 L). Clean fractions were combined to give 58 g of pure product. An additional 13 g of ~70% pure product was obtained from less pure fractions. Yield was 47% over two steps. $^1$H NMR (300 MHz, DMSO-d$_6$) δ 3.45 (m, 1H), 3.6 (s, 3H), 3.8 (m, 1H), 4.8 (d, 1H), 5.3 (d, 1H), 6.8 (d, 2H), 7.1 (d, 2H), 7.7-7.5 (m, 3H), 8.9 (t, 1H).

Example 2

Representative General Procedure for Simultaneous
Synthesis of the Benzodiazepine Core and
Installation of C3 Functionality

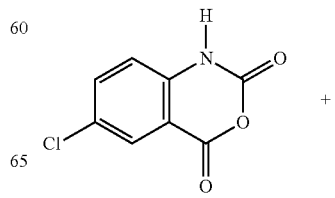

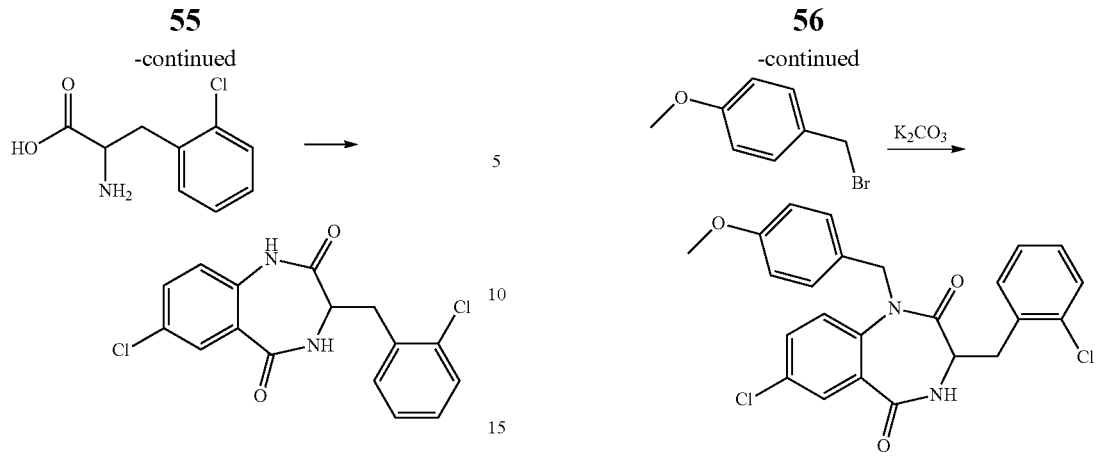

7-Chloro-3-(2-chlorobenzyl)-3,4-dihydro-1H-benzo[e][1,4]diazepine-2,5-dione

2-Amino-3-(2-chlorophenyl)propanoic acid hydrochloride (3.0 g, 12.7 mmol) was suspended in acetonitrile (50 mL) and water (5 mL), triethylamine (3.57 mL, 25.4 mmol) was added which caused a precipitate to form and inefficient stirring. Water (10 mL) was added until all solids were dissolved. 5-Chloroisatoic anhydride (2.51 g, 12.7 mmol) was added in portions, waiting until each portion dissolved before adding the next. Successive portions required longer periods of time, up to 15 minutes for the last portions. After the last portion was added, the suspension was sonicated for several minutes then stirred at ambient temperature overnight. The clear solution was concentrated in vacuo then azeotroped twice with acetone. The residue was redissolved in acetic acid (30 mL) and heated to 130° C. for 6 hours. The mixture was concentrated in vacuo to an oil, diluted with ethyl acetate (150 mL), washed with water (3×50 mL) then brine, dried with sodium sulfate, filtered and concentrated to a brown solid. This solid was resuspended in ethyl acetate (20 mL) and hexanes (10 mL) then slurried at ambient temperature for 30 minutes. Filtration provided 7-chloro-3-(2-chlorobenzyl)-3,4-dihydro-1H-benzo[e][1,4]diazepine-2,5-dione (2.4 g, 56%). $^1$H-NMR (300 MHz, DMSO-$d_6$) δ 2.97 (m, 1H), 3.23 (m, 1H), 4.00 (m, 1H), 7.12 (d, 1H, J=8.79 Hz), 7.27 (m, 2H), 7.40 (m, 2H), 7.58 (dd, 1H, J1=8.79 Hz, J2=2.64 Hz), 7.67 (d, 1H, J=2.64 Hz), 8.73 (d, 1H, J=6.15 Hz), 10.59 (s, 1H); ESI m/z 335.0, 337.0.

Example 3

Representative General Procedure for Installation of a Para-MethoxylBenzyl (PMB) Protecting Group on the NI Amide Nitrogen Atom

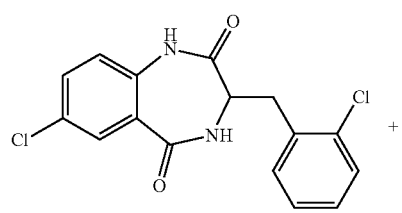 +

7-Chloro-3-(2-chlorobenzyl)-1-(4-methoxybenzyl)-3,4-dihydro-1H-benzo[e][1,4]diazepine-2,5-dione 7-Chloro-3-(2-chlorobenzyl)-3,4-dihydro-1H-benzo[e][1,4]diazepine-2,5-dione (0.8 g, 2.39 mmol), powdered potassium carbonate (0.495 g, 3.58 mmol) and 4-methoxybenzyl chloride (0.39 mL, 2.86 mmol) were suspended in N,N-dimethylformamide (20 mL) and stirred at ambient temperature overnight. The solution was poured into water (100 mL) and ethyl acetate (150 mL). The layers were separated and the organic layer was washed with water (2×100 mL) then brine, and dried with sodium sulfate, decanted and concentrated in the presence of silica gel. The product was purified by column chromatography eluting with a gradient of 0-50% ethyl acetate in hexanes to yield 7-chloro-3-(2-chlorobenzyl)-1-(4-methoxybenzyl)-3,4-dihydro-1H-benzo[e][1,4]diazepine-2,5-dione (0.65 g, 60%). $^1$H NMR (300 MHz, DMSO-$d_6$) δ 3.06 (m, 1H), 3.30 (m, 2H), 3.66 (s, 3H), 4.13 (m, 1H), 4.82 (d, 1H), 5.34 (d, 1H), 6.76 (d, 2H, J=8.79 Hz), 6.96 (d, 2H, J=8.79 Hz), 7.21-29 (m, 2H), 7.36-45 (m, 2H), 7.54-7.61 (m, 3H), 8.97 (d, 1H, J=5.86 Hz); ESI m/z 455.1.

Example 4

Representative General Procedure for Synthesis of (E)-5,7-Dichloro-benzodiazepin-2(3H)-one Part I:

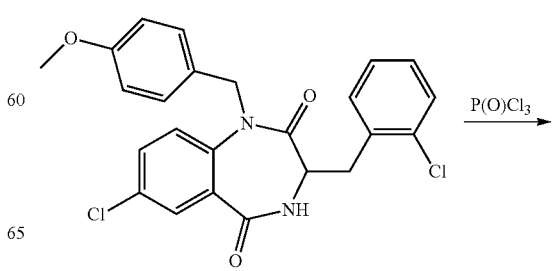

-continued

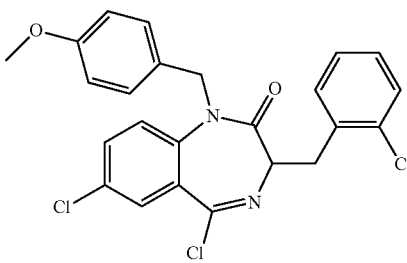

(E)-5,7-Dichloro-3-(2-chlorobenzyl)-1-(4-methoxy-benzyl)-1H-benzo[e][1,4]diazepin-2(3H)-one 7-Chloro-3-(2-chlorobenzyl)-1-(4-methoxybenzyl)-3,4-dihydro-1H-benzo[e][1,4]diazepine-2,5-dione (0.65 g, 1.43 mmol) was suspended in anhydrous toluene (10 mL) under a nitrogen atmosphere. N,N-Dimethylaniline (0.36 mL, 2.9 mmol) was added followed by phosphorus oxychloride (0.20 mL, 2.1 mmol) and the mixture was heated at 90° C. for 4 hours. After cooling to ambient temperature, the mixture was diluted with 40 mL of ethyl acetate:hexanes (1:2), washed with ice water (10 mL), ice cold 1 M hydrogen chloride (2×10 mL), and brine, then dried with sodium sulfate, decanted and concentrated in vacuo. The residue was redissolved in a small amount of ethyl acetate, then poured onto a silica plug. The product was eluted with 100 mL of ethyl acetate:hexanes (1:2) to yield (E)-5,7-dichloro-3-(2-chlorobenzyl)-1-(4-methoxybenzyl)-1H-benzo[e][1,4]diazepin-2(3H)-one (680 mg, 100%) which was used without further purification.

Part II:

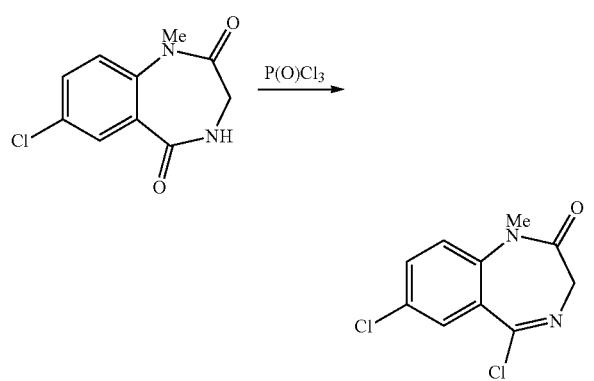

(E)-5,7-Dichloro-1-methyl-1H-benzo[e][1,4]diazepin-2(3H)-one

In a 1 L 2 neck RBF equipped with mechanical stir, condenser and N₂ inlet, 7-chloro-1-methyl-3,4-dihydro-1H-benzo[e][1,4]diazepine-2,5-dione (42.5 g, 0.189 mol) was suspended into 400 mL of toluene. To this was added N,N-dimethylanaline (45.5 g. 0.375 mol) followed by the addition of POCl₃ (29 g, 0.189 mol) and the reaction mixture stirred for 3 min (RT). Reaction flask was placed in a 90° C. oil bath and the reaction mixture stirred/heated for 7 h and then at RT for 9 h. Reaction was quenched by adding 500 mL of ice water and stirred for 15 min. Organic layer was separated and quickly washed with cold 0.5 M HCl (300 mL), cold water (300 mL), and then cold saturated NaHCO₃ (300 mL). Organic layer was dried (MgSO₄), filtered and concentrated on a rotary evaporator to give 40 g of yellow solid. Yield 87.5%. ¹HNMR (300 MHz, DMSO-$d_6$) δ 3.25 (s, 3H), 3.8-3.9 (s, 1H, br), 4.3-4.4 (s, 1H, br), 7.4 (d, 1H), 7.7-7.8 (m, 2H).

Part III:

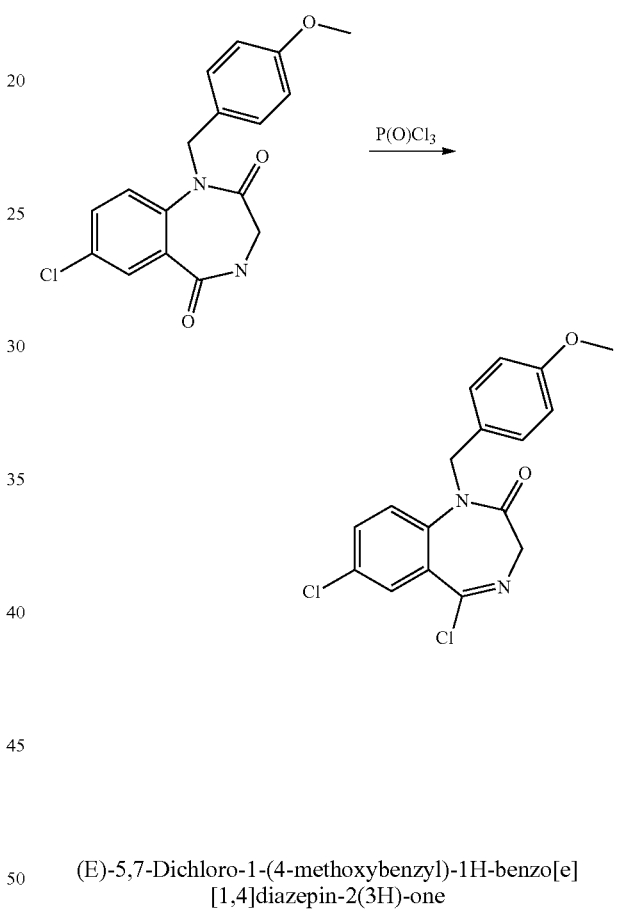

(E)-5,7-Dichloro-1-(4-methoxybenzyl)-1H-benzo[e][1,4]diazepin-2(3H)-one

In a 1 L 3 neck RBF equipped with magnetic stir bar, condenser and N₂ inlet, 7-chloro-1-(4-methoxybenzyl)-3,4-dihydro-1H-benzo[e][1,4]diazepine-2,5-dione (45 g, 0.136 mol) was suspended in 400 mL of toluene. To this was added N,N-dimethylanaline (33 g, 0.272 mol) followed by the addition of POCl₃ (23 g) and the reaction stirred for 3 min (RT). Reaction flask was placed into a 90° C. oil bath and the reaction mixture was heated for 5 h and then cooled. The reaction was quenched by adding 450 mL of ice water and stirred for 15 min. The organic layer was separated and quickly washed with cold water (2×250 mL) and brine (300 mL). Then, the organic layer was dried over MgSO₄, filtered and concentrated on a rotary evaporator to give 57 g of black crude product. Crude product was used for next step with no further purification. Yield 87.5%.

Example 5

Representative General Procedure for Installation of a C3-Substituent on (E)-5,7-Dichloro-benzodiazepin-2(3H)-one

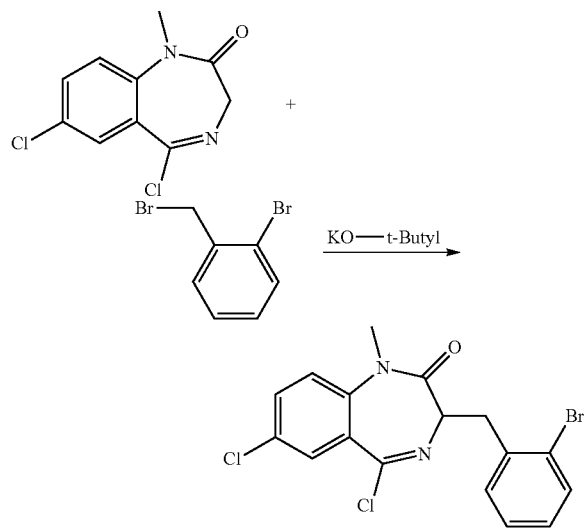

(E)-3-(2-bromobenzyl)-5,7-dichloro-1-methyl-1H-benzo[e][1,4]diazepin-2(3H)-one (E)-5,7-Dichloro-1-methyl-1H-benzo[e][1,4]diazepin-2(3H)-one (400 mg, 1.65 mmol) was dissolved in anhydrous tetrahydrofuran (5 mL) under a nitrogen atmosphere, cooled to −78° C., then a 1 M solution of potassium tert-butoxide in tetrahydrofuran (1.7 mL, 1.7 mmol) was added dropwise. The reaction mixture was stirred for 10 minutes before a solution of the 2-bromobenzyl bromide (411 mg, 1.65 mmol) in tetrahydrofuran (2 mL) was added dropwise. The mixture was stirred at −78° C. for 20 minutes then the cooling bath removed and the mixture was allowed to warm to ambient temperature and stirred at ambient temperature for 18 hours. Piperazine (283 mg, 3.29 mmol) was added to remove excess 2-bromobenzyl bromide and the mixture was stirred at ambient temperature for 30 minutes, diluted with ethyl acetate, and washed with cold 1 M aqueous hydrogen chloride (2×40 mL). The organic layers were dried with sodium sulfate, decanted and concentrated in vacuo to approximately 20 mL of a red liquid. The product was purified on a short pad of silica gel eluting with 100 mL of ethyl acetate:hexanes (1:2) to yield (E)-3-(2-bromobenzyl)-5,7-dichloro-1-methyl-1H-benzo[e][1,4]diazepin-2(3H)-one (0.44 g, 65%). $^1$H NMR (300 MHz, CDCl$_3$) δ 3.40 (s, 3H) 3.75 (m, 2H), 4.15 (m, 1H), 7.05-7.55 (m, 7H).

Example 6

Representative Procedures for the Preparation of Benzyl Halides

Benzyl halides can be prepared from the corresponding benzyl alcohol using known procedures, such as by treating a benzyl alcohol with thionyl chloride. A variety of benzyl alcohols are commercially available. In addition, a variety of benzyl alcohols can be prepared using the following methods: i) reduction of a commercially available carboxylic acid (e.g., reduction using lithium aluminum hydride); ii) conversion of a dibromo-benzyl alcohol to a dialkyl-benzyl alcohol using, for example, a dialkylzinc reagent in the presence of a palladium catalyst, such as PdCl$_2$(dppf); iii) conversion of a dibromobenzyl acetate to a dialkyl benzyl acetate followed by hydrolysis; iv) formylation of the appropriate aromatic followed by reduction; or v) conversion of a reactive chlorobenzoate ester to the respective alkyl benzoate ester using, for example, a Grignard reagent in the presence of an iron catalyst, such as Fe(acac)$_3$, followed by reduction.

Part I: Representative Procedures for the Preparation of a Substituted Benzyl Alcohol from Dibromotoluene.

1,3-Dibromo-2-(bromomethyl)benzene

A mixture of 2,6-dibromotoluene (22.9 g, 92 mmol), N-bromosuccinimide (NBS) (15 g, 84 mmol), CCl$_4$ (250 mL) and benzoyl peroxide (0.03 eq) was stirred at 85° C. (hot oil bath temperature) for 16 h, cooled to RT, filtered, washed with aq. NaHSO$_3$, dried (Na$_2$SO$_4$), filtered, and evaporated to give 29.5 g (yield of 98%) of title product as a white solid. This solid contained 10% unreacted starting material but was successfully used without further purification. $^1$H NMR (300 MHz, CDCl$_3$) δ 4.81 (s, 2H), 7.01 (t, 1H), 7.53 (d, 2H).

2,6-Dibromobenzyl acetate

A mixture of 1,3-dibromo-2-(bromomethyl)benzene (27.6 g, 84 mmol), NaOAc (35.5 g, 5 eq.) and dimethylformamide (DMF) (150 mL) was stirred at 100° C. (hot oil bath temperature) for 1.75 h, allowed to cool, and then partitioned between heptane (500 mL) and water (200 mL). After removing the organic layer, the aqueous layer was extracted with heptane (200 mL). The combined organics were washed with H$_2$O (2×300 mL), dried (Na$_2$SO$_4$), filtered, and evaporated to give 24.57 g (yield of 95%) of title product as a colorless oil. This oil contained 13% unreacted starting material but was successfully used without further purification. $^1$H NMR (300 MHz, CDCl$_3$) δ 2.10 (s, 3H), 5.41 (s, 2H), 7.08 (t, 1H), 7.58 (d, 2H).

2,6-Diethylbenzyl acetate

To a cooled (dry ice-acetone bath) mixture of 2,6-dibromobenzyl acetate (5.05 g, 16.4 mmol) and PdCl$_2$(dppf) (0.08 eq) in dry THF (50 mL) was added 1.1 M Et$_2$Zn (60 mL, 66 mmol, 4 eq). The resulting mixture was allowed to warm to RT, stirred at 45° C. (programmed block temperature, ~40 h), and added to a stirred mixture of dilute HCl and heptane/EtOAc. The organic layer was dried (Na$_2$SO$_4$), filtered, and evaporated. Chromatography (2%-10% EtOAc/heptane stepwise gradient) gave 2.12 g (yield of 63%) of the title product, along with 0.20 g of 2,6-diethylbenzyl alcohol. $^1$H NMR (300 MHz, CDCl$_3$) δ 1.21 (t, 6H), 2.07 (s, 3H), 2.70 (q, 4H), 5.19 (s, 2H), 7.09 (d, 2H), 7.22 (dd, 1H). The following compound was prepared by making appropriate substitutions to the above procedure:

2,6-Dimethylbenzyl acetate $^1$H NMR (300 MHz, CDCl$_3$) δ 2.06 (s, 3H), 2.39 (s, 6H), 5.17 (s, 2H), 7.02 (d, 2H), 7.12 (dd, 1H).

(2,6-Diethylphenyl)methanol

A mixture of 2,6-diethylbenzyl acetate (2.11 g, 10.2 mmol), MeOH (20 mL), H$_2$O (6 mL), and NaOH (1.99 g, 50 mmol, 5 eq) was stirred at RT overnight.

After concentrating, the mixture was extracted with heptane (50 mL). The organic layer was dried (Na$_2$SO$_4$), filtered, and evaporated to give 1.90 g of title product. $^1$H NMR (300 MHz, CDCl$_3$) δ 1.23 (t, 1H, OH), 1.24 (t, 6H), 1.37 (br s, 1H), 2.79 (q, 4H), 4.75 (d, 2H), 7.09 (d, 2H), 7.21 (dd, 1H). The following compound was prepared by making appropriate substitutions to the above procedure: (2,6-Dimethylphenyl)methanol. $^1$H NMR (300 MHz, CDCl$_3$) δ 1.25 (t, 1H, OH), 2.41 (s, 6H), 4.72 (d, 2H), 7.0-7.15 (m, 3H).

Part 2: Representative Procedure for the Synthesis of an Alkyl-Substituted Benzoate Ester from a Halo-Substituted Benzoate Ester.

Methyl 2,4-diethylbenzoate

To a mixture of Fe(acac)$_3$ (0.34 g, 0.96 mmol), methyl 2,4-dichlorobenzoate (4.0 g, 19.6 mmol), and N-methyl-2-pyrrolidinone (8 mL) in THF (100 mL) at −20° C. under nitrogen was added a tetrahydrofuran (THF) solution (1.0 M) of ethylmagnesium bromide (40.0 mL, 40.0 mmol) over a period of ~5 min. The resulting mixture was stirred while gradually warming to ambient temperature. Stirring was continued for an additional 17 h. The reaction mixture was partitioned between water and dichloromethane. The organic layer was separated, washed with brine, dried (MgSO$_4$), and pumped to dryness under reduced pressure. The brown residue was purified by column chromatography (SiO$_2$, 20% EtOAc/heptane) to give 1.2 g of the desired product as a clear oil (yield of 32%), along with 1.1 g of methyl 4-ethylbenzoate. $^1$H NMR (300 MHz, DMSO-d$_6$) δ1.15 (t, 3H), 1.20 (t, 3H), 2.66 (q, 2H), 2.92 (q, 2H), 3.82 (s, 3H), 7.15 (d, 1H), 7.23 (s, 1H), 7.76 (d, 1H).

Part 3: Representative Procedure for the Synthesis of an Alkyl-Substituted Benzaldehyde from Alkyl-Substituted Benzene.

2,5-Diisopropylbenzaldehyde

In a 200 mL single neck RBF, equipped with magnetic stir bar, 1,4-diisopropylbenzene (4 g, 25 mmol) was dissolved into 50 mL of chloroform. To this solution was added SnCl$_4$ (11.5 g, 5.2 mL, 4.5 mmol) via syringe over 5 min. The reaction mixture was stirred for 5 min and then Cl$_2$CHOMe (2.8 g, 24 mmol) was added via syringe over 15 min. The reaction mixture was stirred for 20 h (RT) and reaction progress was followed by GC/MS. Reaction was quenched by adding 70 mL of water and stirring the mixture for 10 min. Organic layer was separated and washed with 3 N HCl (2×50 mL). The organic layer was dried over MgSO$_4$, filtered and concentrated to give 4 g of crude product. This was subjected to column chromatography using 80 g of silica and from 100% heptane to 95:5 Heptane:EtOAc as a mobile phase to give 2.4 g of product (yield of 56%). $^1$H NMR (300 MHz, CDCl$_3$) δ 1.17 (d, 6H), 1.25 (d, 6H), 2.9 (septet, 1H), 4.9 (septet, 1H), 7.4 (m, 2H), 7.65 (d, 1H), 10.35 (s, 1H).

The following compound was prepared based on the above procedure: 3,4-Diethylbenzaldehyde. $^1$H NMR (300 MHz, DMSO-d$_6$) δ1.21 (m, 6H), 2.72 (q, 4H), 7.41 (d, 1H), 7.71 (d, 1H), 7.75 (s, 1H).

Part 4: Representative Procedure for the Synthesis of an Alkyl-Substituted Benzyl Alcohol from an Alkyl-Substituted Benzaldehyde.

(2,5-Diisopropylphenyl)methanol

In a 2-neck RBF equipped with magnetic stir bar and N$_2$ inlet, 2,5-diisopropylbenzaldehyde (1.7 g, 9 mmol) was dissolved into 30 mL of EtOH and NaBH$_4$ (0.37 g, 10 mmol) was added over 20 min (portion-wise). After 18 h stirring at RT, ~95% of solvent was removed on a rotary evaporator and then 5 mL of 0.5 M HCl was added and product was extracted with 25 mL of EtOAc. Organic layer was washed with 15 mL of H$_2$O and 15 mL of brine, dried over Na$_2$SO$_4$, filtered and concentrated to dryness to obtain crude product. This material was subjected to chromatography using heptane: EtOAc as mobile phase to provide 1.1 g of pure product. Yield 65%. $^1$H NMR (300 MHz, CDCl$_3$) δ 1.2-1.3 (d, 12H), 2.8 (septet, 1H), 3.2 (septet, 1H), 5.7 (s, 2H), 7.1-7.3 (m, 3H).

Part 5: Representative Procedure for the Synthesis of an Alkyl-Substituted Benzyl Alcohol from a Dibromobenzyl Alcohol.

(3,5-Diethylphenyl)methanol

To a cooled (dry ice) mixture of 3,5-dibromobenzyl alcohol (1 g, 3.8 mmol) and PdCl$_2$(dppf)[0.07 eq] in dry THF (10 mL) was added 1.1 M Et$_2$Zn (15 mL, 16 mmol, 4.4 eq). The resulting mixture was allowed to warm to RT, stirred at 45° C. (programmed block temperature, overnight). To bring the reaction to completion (disappearance of both starting material and monoalkylated product) additional 1.1 M Et$_2$Zn (10 mL, 11 mmol, 2.9 eq) was added with continued stirring at 45° C. (again overnight). After cooling, the reaction mixture was then added to a stirred mixture of dilute HCl and heptane/EtOAc (2:1; ~200 mL), and the organic layer was dried (Na$_2$SO$_4$), filtered, and evaporated. Chromatography (10% EtOAc/heptane) gave 0.33 g (yield of 53%) of title product. $^1$H NMR (300 MHz, CDCl$_3$) δ 1.22 (t, 6H), 1.65 (br s, 1H), 2.61 (q, 4H), 4.66 (s, 2H), 6.95-7.05 (m, 3H).

The following compounds can be prepared by making the appropriate substitutions to the above procedure.

(2,5-Diethylphenyl)methanol $^1$H NMR (300 MHz, CDCl$_3$) δ 1.22 (t, 6H), 1.50 (br s, 1H), 2.61 (q, 2H), 2.65 (q, 2H), 4.70 (br s, 1H), 7.0-7.2 (m, 3H).

(3,4-Diethylphenyl)methanol $^1$H NMR (300 MHz, DMSO-d$_6$) δ1.14 (t, 3H), 1.20 (t, 3H), 2.62-2.70 (m, 4H), 4.46 (d, 2H), 5.03 (t, 1H), 7.05-7.13 (m, 3H).

Part 6: Representative Procedure for the Synthesis of an Alkyl-Substituted Benzyl Alcohol from an Alkyl-Substituted Benzyl Ester.

(2,4-Diethylphenyl)methanol

To a suspension of lithium aluminum hydride (0.47 g, 11.8 mmol) in anhydrous THF (20 mL) at room temperature under nitrogen was added a solution of methyl 2,4-diethylbenzoate (1.5 g, 7.8 mmol) in THF (15 mL) with stirring over a period of −5 min. The resulting mixture was stirred at room temperature for 60 min and was then quenched by slow addition of ethyl acetate (until bubbling stopped). The mixture was partitioned between ethyl acetate and 1N HCl (aq). The aqueous layer was separated and extracted with ethyl acetate. Organic layers were combined, dried (MgSO$_4$), and evaporated to dryness to give 1.3 g of the desired alcohol as a clear oil (yield of 100%). $^1$H NMR (300 MHz, CDCl$_3$) δ1.13 (t, 3H), 1.17 (t, 3H), 2.58 (q, 2H), 2.61 (q, 2H), 4.43 (d, 2H), 5.02 (t, 1H), 7.05-7.11 (m, 3H).

Part 7: Representative Procedure for the Synthesis of an Alkyl-Substituted Benzylhalide from an Alkyl-Substituted Benzyl Alcohol.

2-(Chloromethyl)-1,3-diethylbenzene

To a mixture of (2,6-diethylphenyl)methanol (1.83 g, 11.1 mmol), toluene (20 mL) and DMF (6 drops) was added $SOCl_2$ (2.1 g, 1.6 eq). The resulting solution was stirred at RT (1 h). After evaporating to dryness, the residue was taken up in heptane (~50 mL) and washed with water (~5 mL), dried ($Na_2SO_4$), filtered and evaporated to give 1.97 g (yield of 97%) of title product. $^1$H NMR (300 MHz, $CDCl_3$) δ 1.28 (t, 6H), 2.79 (q, 2H), 4.70 (s, 2H), 7.09 (d, 2H), 7.20 (m, 1H).

The following compounds can be prepared by making the appropriate substitutions to the above procedure.

1-(Chloromethyl)-2,3-dimethylbenzene $^1$H NMR (300 MHz, $CDCl_3$) δ 2.29 (s, 3H), 2.31 (s, 3H), 4.60 (s, 2H), 7.0-7.2 (m, 3H).

1-(Iodomethyl)-2,4-dimethyl benzene $^1$H NMR (300 MHz, $CDCl_3$) δ 2.23 (s, 6H), 4.35 (s, 2H), 6.9-7.05 (m, 2H), 7.1 (d, 1H).

1-(Chloromethyl)-3,4-dimethyl benzene $^1$H NMR (300 MHz, $CDCl_3$) δ 2.20 (s, 6H), 4.67 (s, 2H), 7.1-7.2 (m, 3H).

2-(Chloromethyl)-1,3-dimethylbenzene $^1$H NMR (300 MHz, $CDCl_3$) δ 2.42 (s, 6H), 4.64 (s, 2H), 7.02 (d, 2H), 7.12 (dd, 1H).

2-(Iodomethyl)-1,4-dimethyl benzene $^1$H NMR (300 MHz, $CDCl_3$) δ 2.22 (s, 3H), 2.26 (s, 3H), 4.15 (s, 2H), 6.9-7 (m, 2H), 7.16 (d, 1H).

1-(Chloromethyl)-2-ethylbenzene $^1$H NMR (300 MHz, $CDCl_3$) δ 1.2-1.3 (t, 3H), 2.75 (q, 2 H), 4.55 (s, 2H), 7.1-7.35 (m, 4H).

1-(Chloromethyl)-2,4-diethylbenzene $^1$H NMR (300 MHz, $CDCl_3$) δ 1.27 (m, 6H), 2.69 (q, 2H), 2.78 (q, 2H), 4.66 (s, 2H), 6.98-7.10 (m, 2H), 7.26 (m, 1H, contains chloroform signal).

1-(Chloromethyl)-3,4-diethylbenzene $^1$H NMR (300 MHz, DMSO-$d_6$) δ 1.21 (t, 3H), 1.25 (t, 3H), 2.60 (q, 2H), 2.64 (q, 2H), 4.71 (s, 2H), 7.15-7.40 (m, 3H).

1-(Chloromethyl)-3,5-diethylbenzene $^1$H NMR (300 MHz, $CDCl_3$) δ 1.23 (t, 6H), 2.63 (q, 4 H), 4.54 (s, 2H), 7.01 (d, 2H), 7.05 (d, 1H).

2-(Chloromethyl)-1,4-diethylbenzene $^1$H NMR (300 MHz, $CDCl_3$) δ 1.22 (t, 3H), 1.26 (t, 3 H), 2.61 (q, 2H), 2.84 (q, 2H), 4.60 (s, 2H), 7.0-7.2 (m, 3H).

2-(Bromomethyl)-1,4-diisopropylbenzene $^1$H NMR (300 MHz, $CDCl_3$) δ 1.1-1.2 (d, 6H), 1.2-1.3 (d, 6H), 2.8 (septet, 1H), 3.25 (septet, 1H), 4.55 (s, 2H), 7.1-7.3 (m, 3H).

1-(Chloromethyl)-4-ethylbenzene and 1-(Chloromethyl)-4-isopropylbenzene.

Example 7

Representative Procedures for Palladium-Coupling Reaction to Install a Substituent at the C5-Position of the Benzodiazepinone

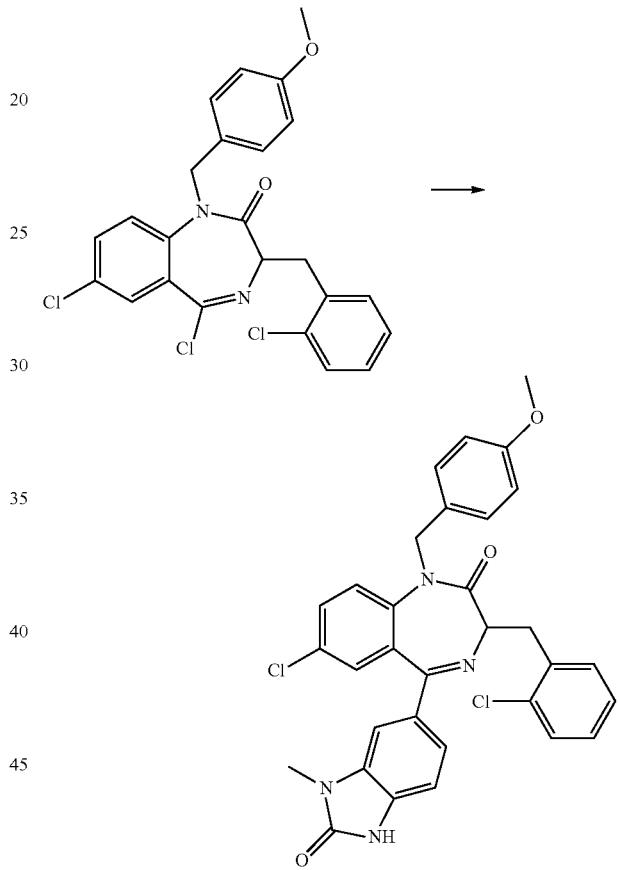

7-Chloro-3-(2-chlorobenzyl)-1-(4-methoxybenzyl)-5-(3-methyl-2-oxo-2,3-dihydro-1H-benzo[d]imidazol-5-yl)-1H-benzo[e][1,4]diazepin-2(3H)-one. 5,7-Dichloro-3-(2-chlorobenzyl)-1-(4-methoxybenzyl)-1H-benzo[e][1,4]diazepin-2(3H)-one (0.416 g, 0.878 mmol) and 1-methyl-6-(4,4,5,5-tetramethyl-1,3,2-dioxaborolan-2-yl)-1H-benzo[d]imidazol-2(3H)-one (0.241 g, 0.878 mmol) were dissolved in 1,4-dioxane (5 mL) and LiCl (0.112 g, 2.63 mmol), and then CsOH (0.442 g, 2.63 mmol) was added followed by water (0.5 mL). The mixture was purged with nitrogen, then [tetrakis(triphenylphosphine)]palladium(0) (0.1 g, 0.088 mmol) was added and the flask was lowered into an 80° C. oil bath and heated at 100° C. for 5.5 h. After cooling to room temperature, the mixture was diluted with ethyl acetate and washed twice with water then once with brine. The organic layer was dried over $MgSO_4$, then filtered and concentrated onto silica gel. Chromatography eluting with 50-100% ethyl acetate in hexanes gave 7-chloro-3-(2-chlorobenzyl)-1-(4-methoxybenzyl)-5-(3-methyl-2-oxo-2,3-dihydro-1H-benzo[d]imidazol-5-yl)-1H-benzo[e][1,4]diazepin-2(3H)-one (0.4 g, 0.68 mmol) as a yellow oil.

Example 8

Representative Procedures for Removal of a p-Methoxybenzyl Group

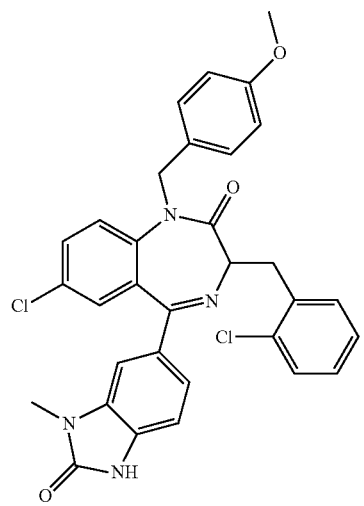

7-Chloro-3-(2-chlorobenzyl)-5-(3-methyl-2-oxo-2,3-dihydro-1H-benzo[d]imidazol-5-yl)-1H-benzo[e][1,4]diazepin-2(3H)-one 7-Chloro-3-(2-chlorobenzyl)-1-(4-methoxybenzyl)-5-(3-methyl-2-oxo-2,3-dihydro-1H-benzo[d]imidazol-5-yl)-1H-benzo[e][1,4]diazepin-2(3H)-one (0.4 g, 0.68 mmol) was dissolved in 10% anisole in 1,1-dichloroethene (DCE, 3 mL) under nitrogen and AlCl$_3$ (0.455 g, 3.42 mmol) was added in one portion. The resulting orange solution was heated to 85° C. for 1.5 h. The solution was allowed to cool. Ethyl acetate was added followed by ice water. This mixture was stirred for 30 min (turned from yellow to colorless) then partitioned and the organic layer was washed with water then brine. The organic layer was dried over MgSO$_4$, then filtered to give a clear, very pale yellow solution. Silica gel was added and the solvent was removed under reduced pressure. Chromatography on silica gel eluting with 5-50-100% ethyl acetate in hexanes gave 7-chloro-3-(2-chlorobenzyl)-5-(3-methyl-2-oxo-2,3-dihydro-1H-benzo[d]imidazol-5-yl)-1H-benzo[e][1,4]diazepin-2(3H)-one as a white solid (59% yield).

Example 9

Representative Procedure for Preparation of (S)-7-Chloro-3-(2-chlorobenzyl)-5-(3-(3-hydroxypropyl)-2-oxo-2,3-dihydro-1H-benzo[d]imidazol-5-yl)-1H-benzo[e][1,4]diazepin-2(3H)-one (IV-4)

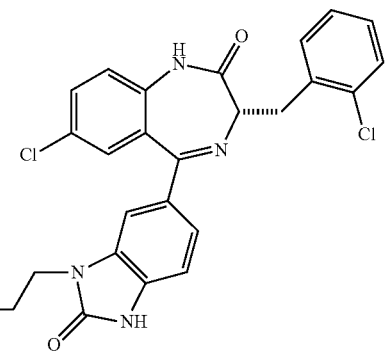

The title compound was prepared according to the procedures described below.

Step 1: Preparation of 3-((5-Bromo-2-nitrophenyl)amino)propan-1-ol

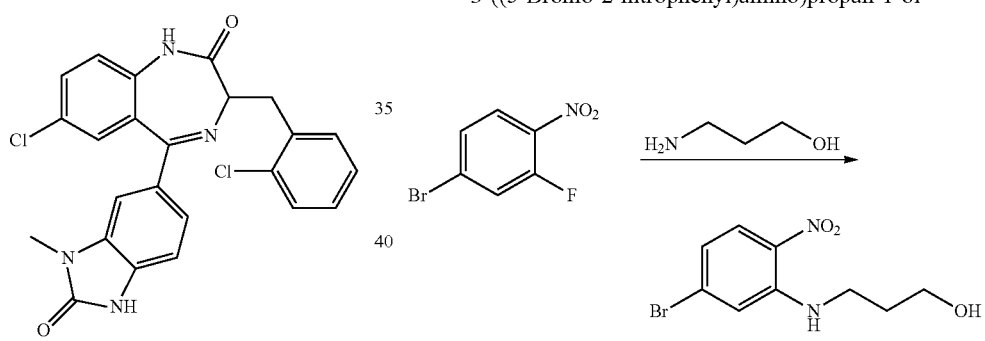

4-Bromo-2-fluoro-1-nitrobenzene (5.38 g, 24.45 mmol) was dissolved in dry DMF (50 mL) under nitrogen and treated with 3-aminopropan-1-ol (5.51 g, 73.4 mmol) at RT. The mixture was stirred at room temperature for 3 h. TLC indicated no starting material remaining. The mixture was diluted with ethyl acetate and washed with water several times, then with brine once. It was dried (MgSO$_4$), then filtered and evaporated to give a yellow oil which was used without further purification.

Step 2: Preparation of 5-Bromo-N-(3-((tert-butyldimethylsilyl)oxy)propyl)-2-nitroaniline

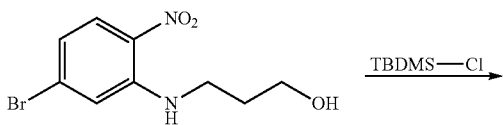

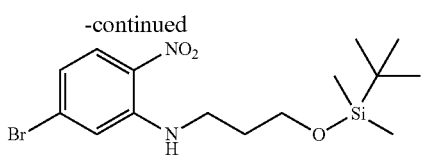

3-((5-bromo-2-nitrophenyl)amino)propan-1-ol (6.73 g, 24.45 mmol) was dissolved in dry dichloromethane (50 mL), and diisopropylethyl amine (6.41 mL, 36.7 mmol) and tert-butyldimethylsilyl chloride (4.42 g, 29.3 mmol) were added. This mixture was stirred at room temperature for 3 h. The organic layer was washed with water, then saturated aqueous ammonium chloride, and then brine. The organic layer was dried over anhydrous magnesium sulfate, filtered and concentrated to give crude 5-bromo-N-(3-((tert-butyldimethylsilyl)oxy)propyl)-2-nitroaniline as an orange oil which was used without further purification.

Step 3: Preparation of 5-Bromo-N-1-(3-((tert-butyldimethylsilyl)oxy)propyl)benzene-1,2-diamine

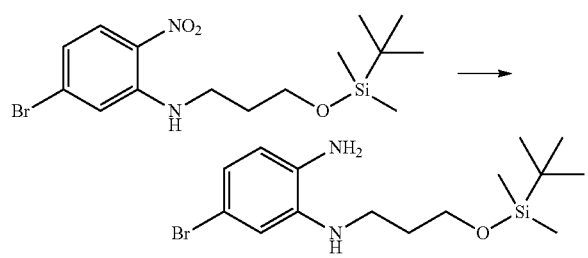

5-Bromo-N-(3-((tert-butyldimethylsilyl)oxy)propyl)-2-nitroaniline from above was added to 2:1 2-propanaol:water (75 mL) (precipitate formed). Iron powder was added (1.147 g, 20.6 mmol) and the mixture was heated to 80° C. for 1 h. It turned black. After allowing to cool, the mixture was filtered through celite, rinsing with ethyl acetate. The filtrate was washed with water, washed with then brine, dried (MgSO$_4$), filtered, and concentrated to give crude 5-bromo-N1-(3-((tert-butyldimethylsilyl)oxy)propyl)benzene-1,2-diamine.

Step 4: Preparation of 6-Bromo-1-(3-((tert-butyldimethylsilyl)oxy)propyl)-1H-benzo[d]imidazol-2(3H)-one

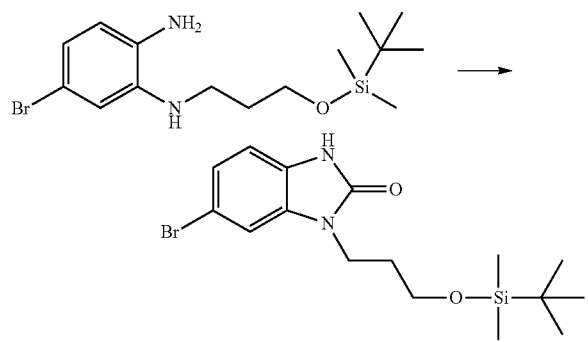

5-Bromo-N1-(3-((tert-butyldimethylsilyl)oxy)propyl)benzene-1,2-diamine (1.8 g, 5.14 mmol) was dissolved in dry THF (50 mL) and 1,1'-carbonyl-diimidazole (0.92 g, 5.65 mmol) was added. The dark brown solution was stirred at room temperature under nitrogen overnight. The mixture was diluted with ethyl acetate and washed with water then brine and dried over anhydrous magnesium sulfate. After filtration and concentration the crude product was chromatographed on silica gel eluting with 5-50% ethyl acetate in hexanes to give 6-bromo-1-(3-((tert-butyldimethylsilyl)oxy)propyl)-1H-benzo[d]imidazol-2(3H)-one as a purple oily foam (1.14 g, 2.96 mmol).

Step 5: Preparation of 1-(3-((Tert-butyldimethylsilyl)oxy)propyl)-6-(4,4,5,5-tetramethyl-1,3,2-dioxaborolan-2-yl)-1H-benzo[d]imidazol-2(3H)-one

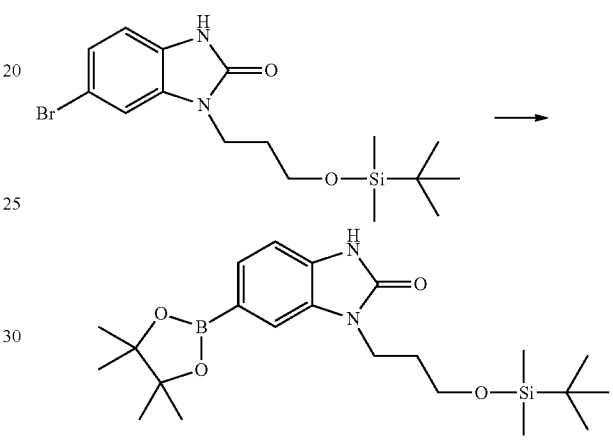

6-Bromo-1-(3-((tert-butyldimethylsilyl)oxy)propyl)-1H-benzo[d]imidazol-2(3H)-one (1.14 g, 2.96 mmol) and bis(pinacolato)diboron (0.75 g, 2.96 mmol) were combined with potassium acetate (0.34 g, 3.6 mmol) in 1,4-dioxane (15 mL) and purged with nitrogen. Pd(dppf)Cl$_2$—CH$_2$Cl$_2$ (120 mg, 0.15 mmol) was added and the mixture was heated to 80° C. for 3 h. The mixture was allowed to cool and diluted with ethyl acetate. The organic layer was washed with water, then brine, and then dried using MgSO$_4$. Chromatography eluting 50% ethyl acetate in hexanes gave 1-(3-((tert-butyldimethylsilyl)oxy)propyl)-6-(4,4,5,5-tetramethyl-1,3,2-dioxaborolan-2-yl)-1H-benzo[d]imidazol-2(3H)-one.

Step 6: Preparation of (S)-5-(3-(3-((Tert-butyldimethylsilyl)oxy)propyl)-2-oxo-2,3-dihydro-1H-benzo[d]imidazol-5-yl)-7-chloro-3-(2-chlorobenzyl)-1-(4-methoxybenzyl)-1H-benzo[e][1,4]diazepin-2(3H)-one

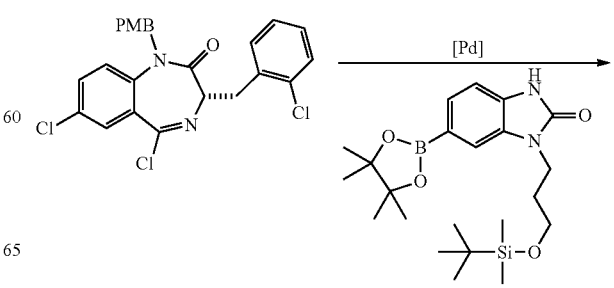

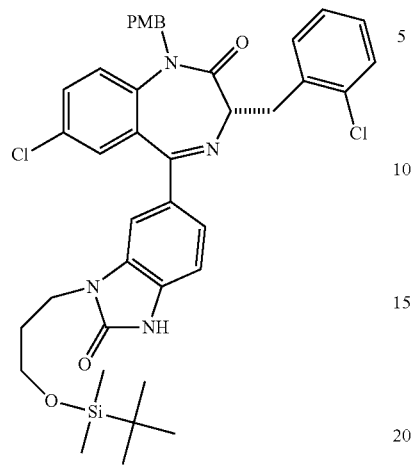

1-(3-((Tert-Butyldimethylsilyl)oxy)propyl)-6-(4,4,5,5-tetramethyl-1,3,2-dioxaborolan-2-yl)-1H-benzo[d]imidazol-2(3H)-one (0.46 g, 1.06 mmol) and (S)-5,7-dichloro-3-(2-chlorobenzyl)-1-(4-methoxybenzyl)-1H-benzo[e][1,4]diazepin-2(3H)-one (0.5 g, 1.06 mmol) were combined in toluene (4 mL) and saturated aqueous sodium bicarbonate (2 mL) and purged with nitrogen. Tetrakis(triphenylphosphine)palladium (122 mg, 0.106 mmol) was added and the mixture was heated at 90° C. for 7.5 h. After cooling, the mixture was diluted with ethyl acetate and washed twice with water then once with brine then dried (MgSO₄). Chromatography, eluting with 10-50% ethyl acetate in hexanes gave the title compound as an orange brown solid (100 mg, 0.134 mmol).

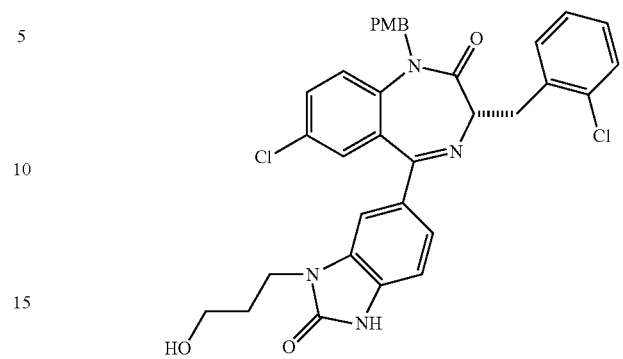

(S)-5-(3-(3-((tert-Butyldimethylsilyl)oxy)propyl)-2-oxo-2,3-dihydro-1H-benzo[d]imidazol-5-yl)-7-chloro-3-(2-chlorobenzyl)-1-(4-methoxybenzyl)-1H-benzo[e][1,4]diazepin-2(3H)-one (100 mg, 0.134 mmol) was dissolved in DCM (~10 mL) and treated with 0.5 mL trifluoroacetic acid. After 1.5 hr, the reaction was ~30% complete by TLC. Another 0.5 mL trifluoroacetic acid was added. After another 1.5 hr, another 0.5 mL trifluoroacetic acid was added. This mixture was allowed to stir at room temperature overnight. It was still mostly starting material by TLC. The solvent was evaporated and azeotroped 3× from DCM. 4 M HCl in 1,4-dioxane (3 mL) was added. This mixture was stirred at RT under nitrogen for 1 hr. TLC (quenched in Et₃N-DCM) showed all starting material had converted. The solvent was evaporated to give the title compound as a yellow oil, which was used in the next step without further purification.

Step 7: Preparation of (S)-7-Chloro-3-(2-chlorobenzyl)-5-(3-(3-hydroxypropyl)-2-oxo-2,3-dihydro-1H-benzo[d]imidazol-5-yl)-1-(4-methoxybenzyl)-1H-benzo[e][1,4]diazepin-2(3H)-one Step 8: Preparation of (S)-7-Chloro-3-(2-chlorobenzyl)-5-(3-(3-hydroxypropyl)-2-oxo-2,3-dihydro-1H-benzo[d]imidazol-5-yl)-1H-benzo[e][1,4]diazepin-2(3H)-one

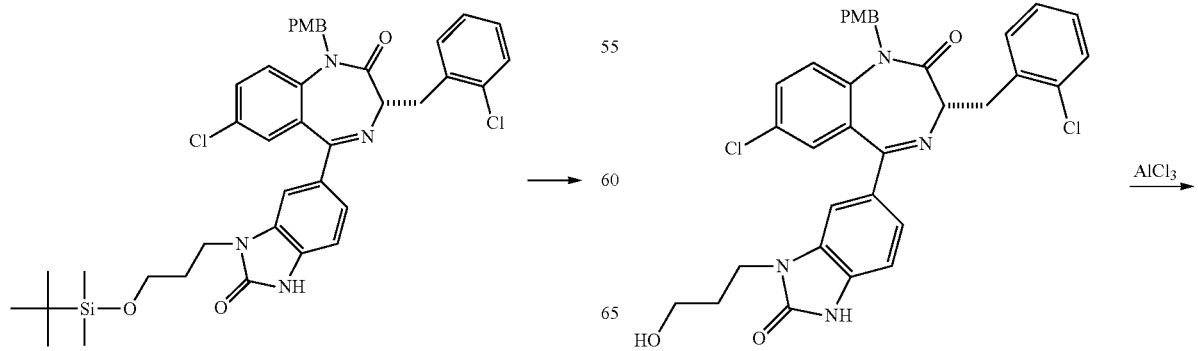

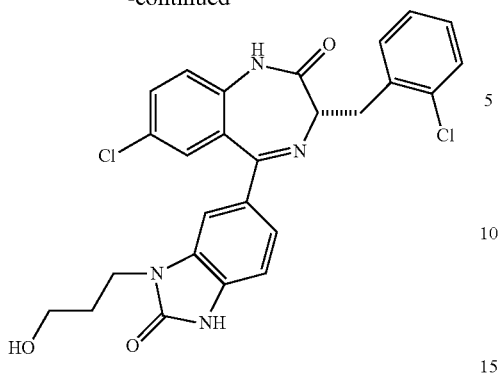

(S)-7-Chloro-3-(2-chlorobenzyl)-5-(3-(3-hydroxypropyl)-2-oxo-2,3-dihydro-1H-benzo[d]imidazol-5-yl)-1-(4-methoxybenzyl)-1H-benzo[e][1,4]diazepin-2(3H)-one was dissolved in dichloroethane (2 mL) and anisole (200 µL) was added followed by AlCl$_3$ (165 mg). This mixture was heated to 85-90° C. for one hour. After cooling, the mixture was diluted with ethyl acetate and quenched with ice. 1M Citric acid was added and the layers separated. The organic layer was washed with brine, then dried (MgSO$_4$). After filtration, the solvent was evaporated onto silica gel. Chromatography eluting with 5% ethyl acetate in hexanes for 5 min then a gradient over 30 minutes up to 100% ethyl acetate gave the crude product as a yellow foam (70 mg). The product was re-columned twice with DCM—10% MeOH in DCM to provide (S)-7-chloro-3-(2-chlorobenzyl)-5-(3-(3-hydroxypropyl)-2-oxo-2,3-dihydro-1H-benzo[d]imidazol-5-yl)-1H-benzo[e][1,4]diazepin-2(3H)-one (20 mg) as a white solid that was 97% pure by HPLC: MP=210° C.; Optical rotation: C=1.0 (CHCl$_3$), $[\alpha]_D$=−26°; MS (m/z): 509.6; $^1$H NMR (d$^6$-DMSO) δ 11.5 (s, 1H), 10.7 (s, 1H), 7.6 (d, 1H) 7.5 (d, 1H), 7.4 (d, 1H), 7.3-7.2 (m, 4H), 7.1 (s, 1H), 6.95 (d, 1H), 6.85 (d, 1H), 4.3 (m, 2H), 3.8 (m, 2H), 3.7 (m, 1H), 3.5-3.3 (m, 2H), 2.1-2.0 (m, 2H).

Based on the foregoing procedures, the following compounds were prepared. For example, (R)-7-chloro-3-(2-chlorobenzyl)-5-(3-(3-hydroxypropyl)-2-oxo-2,3-dihydro-1H-benzo[d]imidazol-5-yl)-1H-benzo[e][1,4]diazepin-2(3H)-one (IV-3) was prepared by using compound (R)-5,7-dichloro-3-(2-chlorobenzyl)-1-(4-methoxybenzyl)-1H-benzo[e][1,4]diazepin-2(3H)-one (0.5 g, 1.06 mmol) in place of compound (S)-5,7-dichloro-3-(2-chlorobenzyl)-1-(4-methoxybenzyl)-1H-benzo[e][1,4]diazepin-2(3H)-one (0.5 g, 1.06 mmol) in Step 6: Optical rotation: C=1.0 (CHCl$_3$), $[\alpha]_D$=+26°; MS (m/z): 509; $^1$H NMR (d$^6$-DMSO) δ 11.5 (s, 1H), 10.7 (s, 1H), 7.6 (d, 1H) 7.5 (d, 1H), 7.4 (d, 1H), 7.3-7.2 (m, 4H), 7.15 (s, 1H), 6.9 (d, 1H), 6.8 (d, 1H), 4.5 (m, 2H), 3.8 (m, 2H), 3.7 (m, 1H), 3.5-3.3 (m, 2H), 1.7 (m, 2H).

7-Chloro-3-(2-chlorobenzyl)-5-(3-(3-hydroxypropyl)-2-oxo-2,3-dihydro-1H-benzo[d]imidazol-5-yl)-1-methyl-1H-benzo[e][1,4]diazepin-2(3H)-one (I-7)

was prepared by using compound (E)-5,7-dichloro-3-(2-chlorobenzyl)-1-methyl-1H-benzo[e][1,4]diazepin-2(3H)-one in place of compound (S)-5,7-dichloro-3-(2-chlorobenzyl)-1-(4-methoxybenzyl)-1H-benzo[e][1,4]diazepin-2(3H)-one (0.5 g, 1.06 mmol) in Step 6: HRMS calc.=523.1304 g/mol, HRMS obs.=523.1302 g/mol; $^1$H NMR (d$^6$-DMSO) δ 11.11 (s, 1H), 7.71 (m, 1H), 7.69 (m, 1H), 7.54 (m, 1H), 7.39 (m, 1H), 7.32-7.21 (m, 4H), 6.95 (m, 2H), 4.58 (t, 1H), 3.82 (m, 3H), 3.56 (m, 1H), 3.45 (m, 3H), 1.78 (m, 2H).

Example 10

Representative Procedures for Preparing 7-Chloro-3-(2-chlorobenzyl)-1-(2-hydroxyethyl)-5-(3-methyl-2-oxo-2,3-dihydro-1H-benzo[d]imidazol-5-yl)-1H-benzo[e][1,4]diazepin-2(3H)-one (I-8)

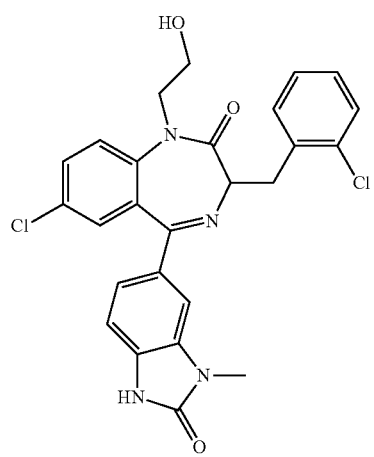 [SMILES: Cn1c(=O)[nH]c2ccc(C3=NC(Cc4ccccc4Cl)C(=O)N(CCO)c4ccc(Cl)cc43)cc21]

The title compound was prepared according to the following procedures.

Step 1: Preparation of 2-(7-Chloro-3-(2-chlorobenzyl)-2,5-dioxo-2,3,4,5-tetrahydro-1H-benzo[e][1,4]diazepin-1-yl)ethyl acetate

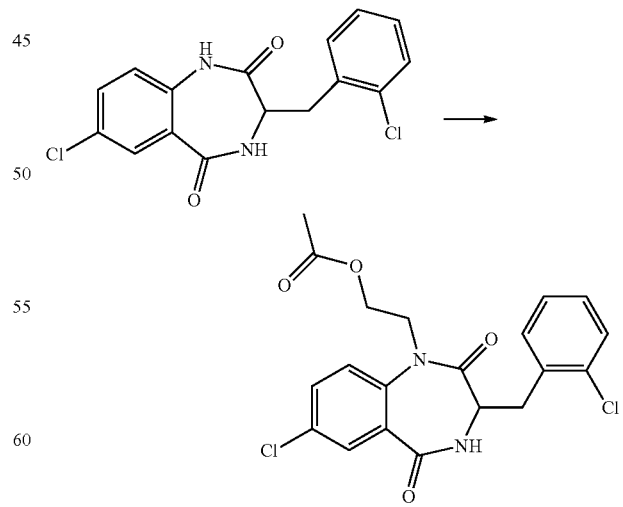

To 7-chloro-3-(2-chlorobenzyl)-3,4-dihydro-1H-benzo[e][1,4]diazepine-2,5-dione (0.5 g, 1.5 mmol) in N,N-dimethylformamide (10 mL), was added powdered potassium carbonate (0.31 g, 2.2 mmol) followed by 2-bromoethylacetate (0.17 mL, 1.6 mmol). The mixture was stirred at ambient temperature overnight. After 20 hours, more 2-bromoethylacetate (0.05 mL, 0.5 mmol) was added and stirring was continued at ambient temperature overnight. The reaction mixture was diluted with ethyl acetate (100 mL), washed with water (3×50 mL), washed with brine (50 mL), dried with anhydrous sodium sulfate, decanted, and concentrated to yield crude 2-(7-chloro-3-(2-chlorobenzyl)-2,5-dioxo-2,3,4,5-tetrahydro-1H-benzo[e][1,4]diazepin-1-yl)ethyl acetate, which was used directly in the next step without further purification. MS (m/z): 421.1 (M+H)+.

Step 2: Preparation of 1-(2-((Tert-butyldimethylsilyl)oxy)ethyl)-7-chloro-3-(2-chlorobenzyl)-3,4-dihydro-1H-benzo[e][1,4]diazepine-2,5-dione

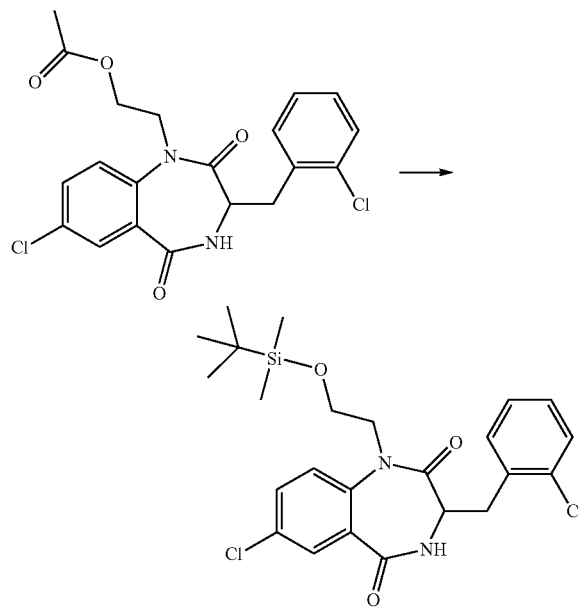

To 2-(7-chloro-3-(2-chlorobenzyl)-2,5-dioxo-2,3,4,5-tetrahydro-1H-benzo[e][1,4]diazepin-1-yl)ethyl acetate (0.62 g, 1.47 mmol) suspended in tetrahydrofuran (10 mL) was added 2M aqueous sodium hydroxide (2.2 mL, 4.4 mmol). Methanol (2 mL) was added, which caused the solution to become homogeneous. The solution was stirred at ambient temperature for 2 hours, then acidified with 1M hydrochloric acid, partitioned between ethyl acetate and brine, separated, dried with sodium sulfate, filtered and concentrated in vacuo. The resulting solid was dissolved in N,N-dimethylformamide (10 mL), and imidazole (0.14 g, 2 mmol) was added followed by tert-butyldimethylsilyl chloride (0.24 g, 1.6 mmol). This mixture was stirred at ambient temperature overnight, then diluted with ethyl acetate, washed with 10% citric acid, water, and brine, dried with sodium sulfate, filtered and concentrated in the presence of silica gel. The product was purified by column chromatography eluting with a gradient of 0-50% ethyl acetate in hexanes to yield 1-(2-((tert-butyldimethylsilyl)oxy)ethyl)-7-chloro-3-(2-chlorobenzyl)-3,4-dihydro-1H-benzo[e][1,4]diazepine-2,5-dione.

Step 3: Preparation of 5,7-Dichloro-3-(2-chlorobenzyl)-1-(2-chloroethyl)-1H-benzo[e][1,4]diazepin-2(3H)-one

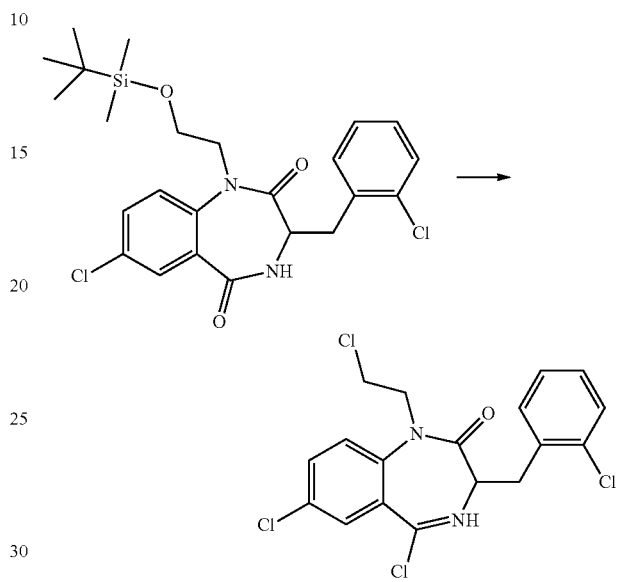

To 1-(2-((tert-butyldimethylsilyl)oxy)ethyl)-7-chloro-3-(2-chlorobenzyl)-3,4-dihydro-1H-benzo[e][1,4]diazepine-2,5-dione (0.33 g, 0.67 mmol) in anhydrous toluene (10 mL) under a nitrogen atmosphere was added N,N-dimethylaniline (0.25 mL, 2 mmol) and phosphorus oxychloride (0.13 mL, 1.3 mmol). This mixture was then heated to 90° C. overnight. The solution was cooled, diluted with ethyl acetate, washed with water, 1M hydrochloric acid, then brine, and dried with sodium sulfate. Activated charcoal was added and the mixture was slurried, then filtered through a silica gel plug eluting with 50% ethyl acetate in hexanes to yield 5,7-dichloro-3-(2-chlorobenzyl)-1-(2-chloroethyl)-1H-benzo[e][1,4]diazepin-2(3H)-one as an oil which was used directly in the next step. MS (m/z): 417.0 (M+H)+.

Step 4: Preparation of 7-Chloro-3-(2-chlorobenzyl)-1-(2-hydroxyethyl)-5-(3-methyl-2-oxo-2,3-dihydro-1H-benzo[d]imidazol-5-yl)-1H-benzo[e][1,4]diazepin-2(3H)-one

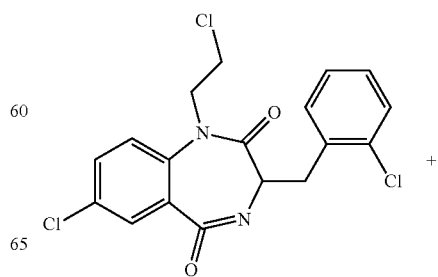
+

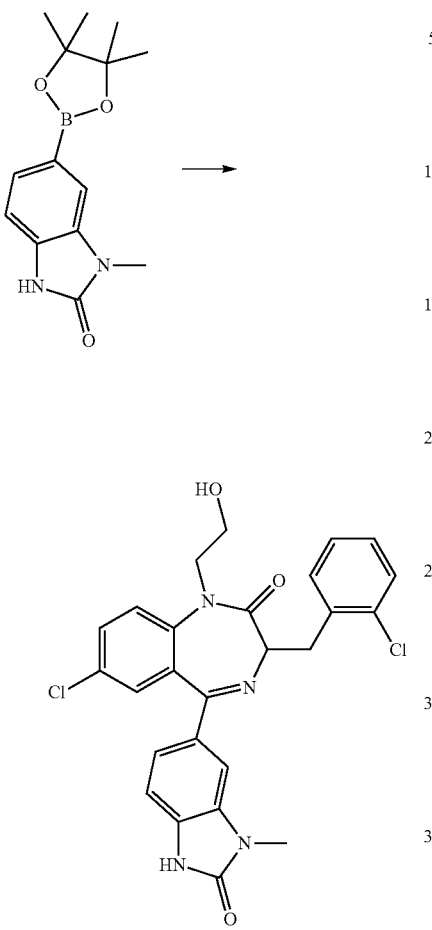

5,7-Dichloro-3-(2-chlorobenzyl)-1-(2-chloroethyl)-1H-benzo[e][1,4]diazepin-2(3H)-one (0.31 g, 0.75 mmol) and 1-methyl-6-(4,4,5,5-tetramethyl-1,3,2-dioxaborolan-2-yl)-1H-benzo[d]imidazol-2(3H)-one (0.2 g, 0.75 mmol) were dissolved in anhydrous 1,4-dioxane (12 mL) while bubbling nitrogen into the solution. Lithium chloride (95 mg, 2.2 mmol) and [Tetrakis(triphenylphosphine)]palladium(0) (0.09 g, 0.074 mmol) were added followed by cesium hydroxide monohydrate (0.38 g, 2.2 mmol) and water (1 mL). The reaction mixture was stirred at 100° C. under a nitrogen atmosphere for 20 hours. The mixture was cooled, diluted with ethyl acetate, washed with water, then brine, dried with sodium sulfate, decanted and concentrated in vacuo. The product was purified by column chromatography eluting with a gradient of 80-100% ethyl acetate in hexanes, followed by 0-10% methanol in ethyl acetate. It was further purified by column chromatography eluting with a gradient of 0-12% methanol in dichloromethane to yield 7-chloro-3-(2-chlorobenzyl)-1-(2-hydroxyethyl)-5-(3-methyl-2-oxo-2,3-dihydro-1H-benzo[d]imidazol-5-yl)-1H-benzo[e][1,4]diazepin-2(3H)-one. $^1$HNMR (DMSO-$d_6$, 400 MHz) δ 11.09 (s, 1H), 7.81 (d, 1H), 7.68 (dd, 1H), 7.49 (d, 1H), 7.38 (d, 1H), 7.31-7.19 (m, 4H), 6.98 (m, 2H), 4.72 (t, 1H), 4.08 (m, 1H), 3.8 (m, 2H), 3.6-3.3 (m, 4H), 3.26 (s, 3M. HRMS [M+H]$^+$ predicted: 509.1147. found: 509.1133.

Example 11

Representative Procedures for Preparing 7-Chloro-3-(4-chlorobenzyl)-5-(3-methyl-2-oxo-2,3-dihydro-1H-benzo[d]imidazol-5-yl)-1H-benzo[e][1,4]diazepin-2(3H)-one (1-13)

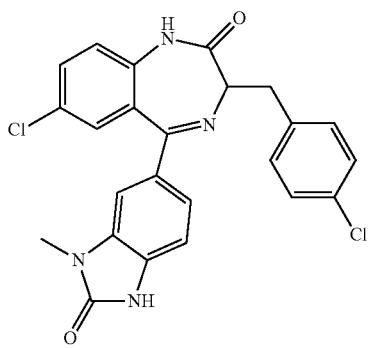 [SMILES: Cn1c(=O)[nH]c2ccc(C3=NC(Cc4ccc(Cl)cc4)C(=O)Nc4ccc(Cl)cc43)cc21]

The title compound was prepared according to the following procedures.

Step 1: Preparation of Palladium Coupling Compound N-Methyl-2-nitro-5-(4,4,5,5-tetramethyl-1,3,2-dioxaborolan-2-yl)aniline The palladium coupling compound N-methyl-2-nitro-5-(4,4,5,5-tetramethyl-1,3,2-dioxaborolan-2-yl)aniline was prepared according to the following procedures.

Part A

Preparation of 5-Bromo-N-methyl-2-nitroaniline

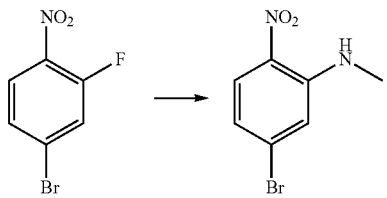

4-Bromo-2-fluoronitrobenzene (Aldrich, 1 eqvt), methylamine (2 eqvt), and hunig's base (3 eqvt) in DMF (1 Molar in substrate) were placed in a sealed vial and heated to 85° C. overnight. The crude mixture was diluted with water, and the product collected by filtration. Purification by chromatography (gradient: 92:8 hexanes:ethyl acetate to 68:32 hexanes: ethyl acetate) provided the title compound. $^1$HNMR (DMSO-$d_6$, 400 MHz) δ 8.22 (bd, J=4.4 Hz, 1H), 7.95 (d, J=8.8 Hz, 1H), 7.14 (d, J=2 Hz, 1H), 6.80 (dd, J=9.2, 2.4 Hz, 1H), 2.92 (d, J=4.8 Hz).

Part B

Preparation of N-Methyl-2-nitro-5-(4,4,5,5-tetramethyl-1,3,2-dioxaborolan-2-yl)aniline

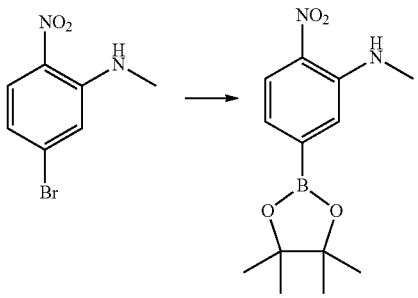

5-Bromo-N-methyl-2-nitroaniline (1 eqvt), bis(pinacolatodiboron) (1.2 eqvt), and potassium acetate (2 eqvt) were combined in dioxane (0.15 M) and degassed 3× replacing the air with nitrogen gas. Pd(dppf) (0.1 eqvt) was added and degassing was done once more. The reaction mixture was heated to 80° C. for three hours. The mixture was then cooled to room temperature and partitioned between water and ethyl acetate. The organic fraction was washed with brine, then concentrated onto silica gel and purified by chromatography to provide the title compound. MS (m/z): 317.2 (M+K)$^+$. $^1$HNMR (DMSO-d$_6$, 400 MHz) δ 8.11 (bd, J=4.8 Hz, 1H), 8.01 (d, J=8.8 Hz, 1H), 7.16 (d, J=0.8 Hz, 1H), 6.87 (dd, J=8.4, 0.8 Hz, 1H), 2.93 (d, J=4.8, 3H), 1.28 (s, 12H).

Step 2: Palladium Coupling Reaction to Provide 7-Chloro-3-(4-chlorobenzyl)-1-(4-methoxybenzyl)-5-(3-(methylamino)-4-nitrophenyl)-1H-benzo[e][1,4]diazepin-2(3H)-one

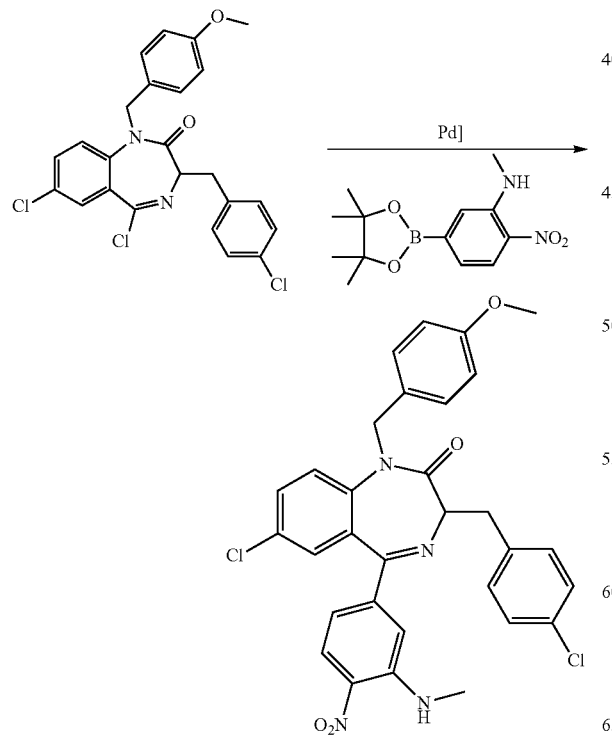

Dichlorobenzodiazepine compound 5,7-dichloro-3-(2-chlorobenzyl)-1-methyl-1H-benzo[e][1,4]diazepin-2(3H)-one was reacted with N-methyl-2-nitro-5-(4,4,5,5-tetramethyl-1,3,2-dioxaborolan-2-yl)aniline under Suzuki coupling conditions based on those described in Example 7 to provide the title compound characterized by MS (m/z): 589.3 (M+1)$^+$ and $^1$HNMR (DMSO-d$_6$, 400 MHz) δ 8.16 (bd, J=5.2 Hz, 1H), 8.04 (d, J=8.8 Hz, 1H), 7.75 (d, J=8.8 Hz, 1H), 7.64 (dd, J=8.8, 2.4 Hz, 1H), 7.35 (d, J=8.4 Hz, 2H), 7.29 (d, J=8.4 Hz, 2H), 7.14 (d, J=2.4 Hz, 1H), 6.81 (d, J=8.4 Hz, 2H), 6.64 (d, J=8.8 Hz, 2H), 6.60 (s, 1H), 6.32 (d, J=8.8 Hz, 1H), 5.48 (d, J=15.2 Hz, 1H), 4.75 (d, J=15.6 Hz, 1H), 3.90 (m, 1H), 3.60 (s, 3H), 3.42-3.35 (m, 2H), 2.75 (d, J=4.8 Hz, 3H).

Step 3: Reduction of Nitro-Aniline Substituted Benzodiazepine to Form Diamine Compound 5-(4-Amino-3-(methylamino)phenyl)-7-chloro-3-(4-chlorobenzyl)-1-(4-methoxybenzyl)-1H-benzo[e][1,4]diazepin-2(3H)-one

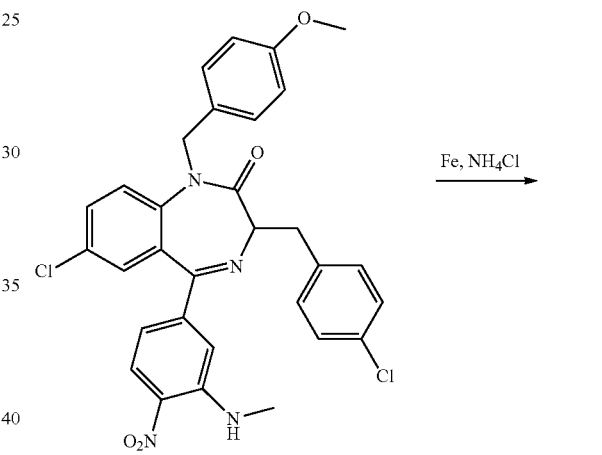

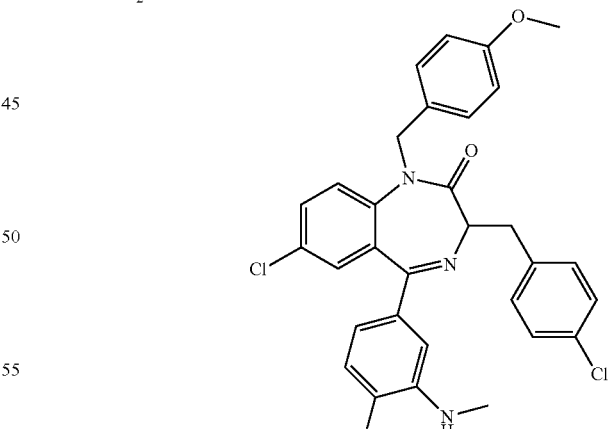

Nitro-aniline compound 7-chloro-3-(4-chlorobenzyl)-1-(4-methoxybenzyl)-5-(3-(methylamino)-4-nitrophenyl)-1H-benzo[e][1,4]diazepin-2(3H)-one was reduced using a mixture of Fe and ammonium chloride to provide the title compound having a MS (m/z) of 559.3 (M+1)$^+$.

Step 4: Reaction of Amino-aniline Substituted Benzodiazepine with Triphosgene to Form Benzimidazolone Compound 7-Chloro-3-(4-chlorobenzyl)-1-(4-methoxybenzyl)-5-(3-methyl-2-oxo-2,3-dihydro-1H-benzo[d]imidazol-5-yl)-1H-benzo[e][1,4]diazepin-2(3H)-one Step 5: Removal of PMB Protecting Group to Provide Compound 7-Chloro-3-(4-chlorobenzyl)-5-(3-methyl-2-oxo-2,3-dihydro-1H-benzo[d]imidazol-5-yl)-1H-benzo[e][1,4]diazepin-2(3H)-one (1-13)

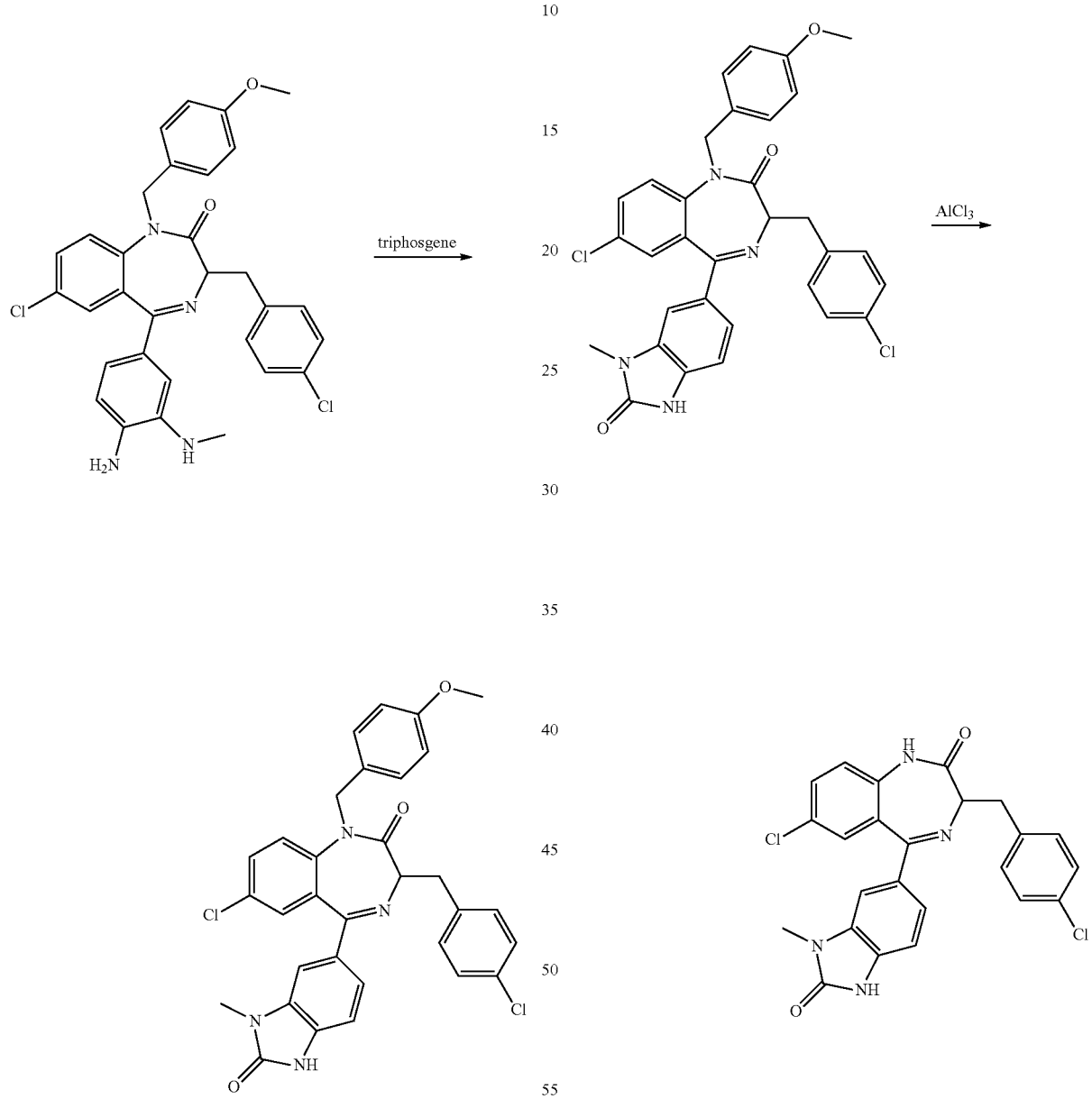

Amino-aniline compound 5-(4-Amino-3-(methylamino)phenyl)-7-chloro-3-(4-chlorobenzyl)-1-(4-methoxybenzyl)-1H-benzo[e][1,4]diazepin-2(3H)-one was treated with triphosgene to provide the title compound having a MS (m/z) of 585.3 (M+1)$^+$.

PMB-protected benzodiazepine was treated with AlCl$_3$ according to the general procedures described in Example 8 to provide the title compound characterized by MS (m/z): 465.2 (M+1)$^+$ and $^1$HNMR (DMSO-d$_6$, 400 MHz) δ 11.08 (bs, 1H), 10.62 (bs, 1H), 7.60 (dd, J=8.8, 2.4 Hz, 1H), 7.36 (d, J=8.8 Hz, 2H), 7.31 (d, J=8.4 Hz, 2H), 7.23 (s, 1H), 7.20 (t, J=2.4 Hz, 1H), 7.10 (d, J=1.6 Hz, 1H), 6.96 (d, J=8.4 Hz, 1H), 6.90 (dd, J=8.0, 1.6 Hz, 1H), 3.66 (t, J=8H, 1H), 3.35-3.31 (m, 2H), 3.25 (s, 3H).

Example 12

Exemplary Procedures for Synthesis of a Benzodiazepinone Containing a C7-Fluoro Group, such as Compound 3-(2-Chlorobenzyl)-7-fluoro-5-(2-oxo-2,3-dihydro-1H-benzo[d]imidazol-5-yl)-1H-benzo[e][1,4]diazepin-2(3H)-one (II-1)

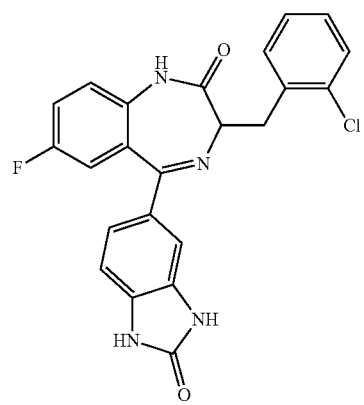 [SMILES: O=C1Nc2ccc(F)cc2C(c2ccc3[nH]c(=O)[nH]c3c2)=NC1Cc1ccccc1Cl]

The title compound was prepared according to the procedures described below.

Step 1: Preparation of 6-Fluoro-1H-benzo[d][1,3]oxazine-2,4-dione

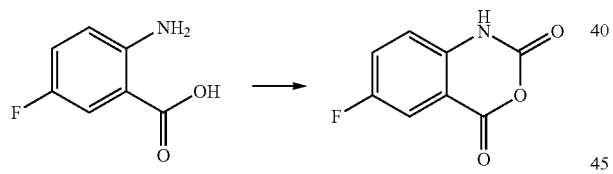

To a solution of 5-fluoroanthranilic acid (10.0 g, 65.5 mmol) in THF (143 mL) was added solid triphosgene (6.70 g, 22.6 mmol, 0.35 equiv). The reaction mixture was stirred at rt overnight and the resulting suspension was filtered and dried to afford 9.23 g (79%) of 5-fluoroisatoic anhydride: $^1$H NMR (400 MHz, DMSO-$d_6$) δ 7.14 (M, 1H), 7.60 (M, 2H), 11.72 (s, 1H).

In a separate preparation, 2-amino-5-fluorobenzoic acid (15 g, 97 mmol) was dissolved in tetrahydrofuran (250 mL) and triphosgene (10.04 g, 33.8 mmol) was added portionwise. A thick white precipitate formed with a small exotherm. The slurry gradually became easier to stir and was left stirring at room temperature for 16 h. The mixture was filtered to provide a white solid which was rinsed with diethyl ether then dried at 50° C. in a vacuum over to give 6-fluoro-1H-benzo[d][1,3]oxazine-2,4-dione (14.1 g, 78 mmol). The 6-fluoro-1H-benzo[d][1,3]oxazine-2,4-dione may be converted to a 7-fluoro-1-(4-methoxybenzyl)-3,4-dihydro-1H-benzo[e][1,4]diazepine-2,5-dione using the procedures described in Example 1.

Step 2: Preparation of 3-(2-Chlorobenzyl)-7-fluoro-3,4-dihydro-1H-benzo[e][1,4]diazepine-2,5-dione

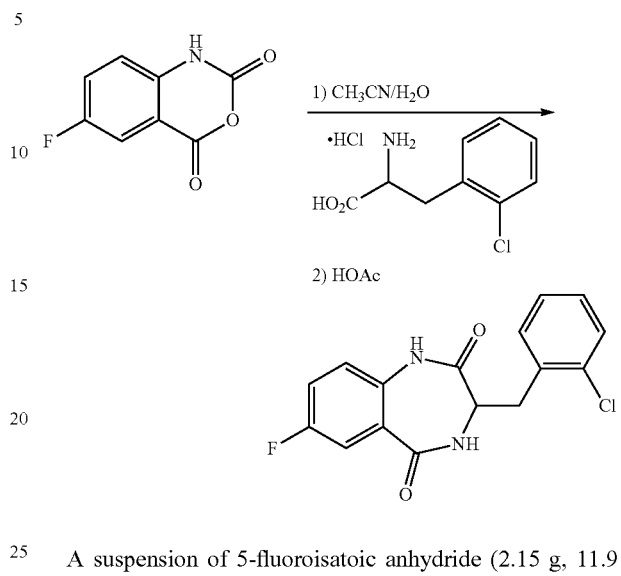

A suspension of 5-fluoroisatoic anhydride (2.15 g, 11.9 mmol), amino acid hydrochloride (2.80 g, 11.9 mmol, 1.0 equiv) and triethylamine (3.34 mL, 23.7 mmol, 2.0 equiv) in CH$_3$CN/H$_2$O (1/1, 23.8 mL) was stirred at rt overnight. The reaction mixture was concentrated, redissolved in HOAc (11.9 mL) and heated in 120° C. oil bath overnight. The reaction mixture was poured into water (200 mL) and the solid collected by filtration. A slurry was formed by the addition of CH$_3$CN (15 mL) and the resulting solid was collected by filtration and dried to afford 2.39 g (63%) of the product. $^1$H NMR (500 MHz, DMSO-$d_6$) δ 2.99 (dd, J=14.9, 7.8 Hz, 1H), 3.29 (d, J=14.7 Hz, 1H), 4.00 (dt, J=8.8, 5.7 Hz, 1H), 7.15 (m, 1H), 7.28 (m, 2H), 7.42 (m, 4H), 8.75 (d, J=6.1, 1H), 10.52 (s, 1H).

Step 3: Preparation of 3-(2-Chlorobenzyl)-7-fluoro-1-(4-methoxybenzyl)-3,4-dihydro-1H-benzo[e][1,4]diazepine-2,5-dione

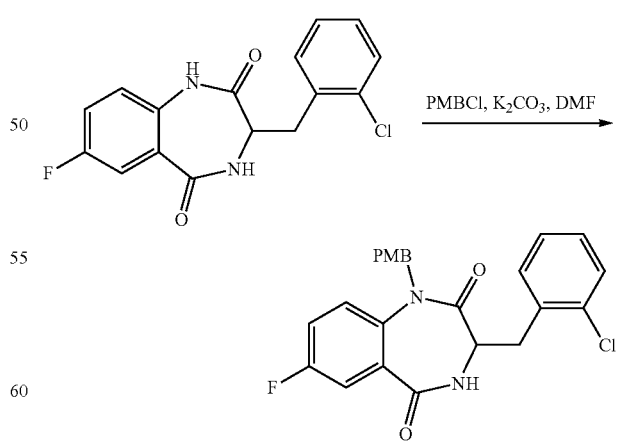

Para-methoxybenzylchloride (PMBCl) (1.07 mL, 7.87 mmol, 1.05 equiv) was added to a suspension of benzodiazepine-dione (2.39 g, 7.50 mmol) and potassium carbonate (1.19 g, 8.62 mmol, 1.15 equiv) in DMF (15.0 mL). The reaction mixture was stirred at rt overnight. The reaction was quenched with water (100 mL) and extracted with EtOAc (2×50 mL). The organic extract was washed with brine (25 mL), dried (Na$_2$SO$_4$), filtered and concentrated. A solid developed upon dissolution in EtOH. The solid was collected by filtration, rinsed with EtOH and dried to afford 2.35 g (71%) of the title compound. $^1$H NMR (500 MHz, CDCl$_3$) δ 3.30 (dd, J=14.6, 8.7 Hz, 1H), 3.51 (dd, J=14.7, 5.9 Hz, 1H), 3.76 (s, 3H), 4.20 (dt, J=8.6, 5.9 Hz, 1H), 4.92 (d, J=15.2 Hz, 1H), 5.18 (d, J=15.2 Hz, 1H), 6.54 (m, 1H), 6.80 (d, J=8.8 Hz, 2H), 7.04 (d, J=8.8 Hz, 2H), 7.25 (m, 3H), 7.36 (m, 2H), 7.47 (m, 1H).

Step 4: Preparation of Di-tert-butyl 5-(3-(2-chlorobenzyl)-7-fluoro-1-(4-methoxybenzyl)-2-oxo-2,3-dihydro-1H-benzo[e][1,4]diazepin-5-yl)-2-oxo-1H-benzo[d]imidazole-1,3(2H)-dicarboxylate

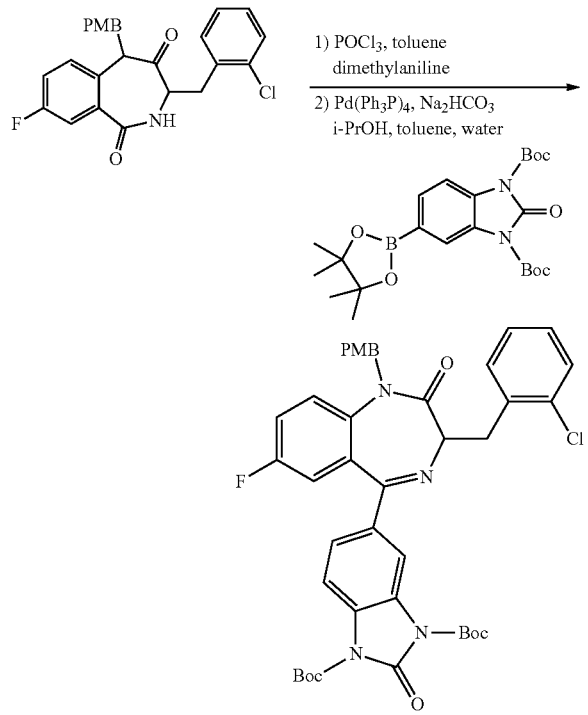

A solution of benzodiazepine-dione (0.500 g, 1.14 mmol), POCl$_3$ (0.133 mL, 1.42 mmol, 1.25 equiv) and dimethylaniline (0.289 mL, 2.28 mmol, 2.0 equiv) was heated to 90° C. overnight. The reaction mixture was cooled, diluted with water (50 mL) and toluene (50 mL). The phases were separated and the aqueous phase was extracted with toluene (50 mL). The organic extracts were washed with brine (50 mL), combined, treated with Na$_2$SO$_4$ (10 g) and DARCO-G60 (1 g) for 10 min. The dark suspension was filtered through celite and the filter cake was rinsed with toluene (50 mL). The filtrate was concentrated to afford cloroimidate intermediate. $^1$H NMR (500 MHz, CDCl$_3$) δ 3.54 (dd, J=13.9, 6.9 Hz, 1H), 3.77 (s, 3H), 3.80 (dd, J=13.9, 6.9 Hz, 1H), 3.93 (t, J=6.9 Hz, 1H), 4.80 (d, J=15.2 Hz, 1H), 5.30 (d, J=15.2 Hz, 1H), 6.77 (d, J=8.5 Hz, 2H), 6.94 (d, J=8.5 Hz, 2H), 7.23 (m, 5H), 7.38 (m, 1 H), 7.55 (m, 1H).

A solution of the chloroimidate intermediate and the boronic acid pinacol ester (0.550 g, 1.19 mmol, 1.05 equiv) in toluene (2.5 mL) was diluted with i-PrOH (2.5 mL) and saturated aqueous sodium bicarbonate solution (0.63 mL) under N$_2$ purge. Palladium catalyst (66 mg, 0.057 mmol, 0.05 equiv) was added and the mixture was heated at 60° C. for 6 h. The reaction mixture was diluted with water (10 mL) and toluene (20 mL). The phases were separated and the aqueous phase was extracted with toluene (20 mL). The combined extracts were concentrated and the residue was purified by silica gel chromatography (20 g SiO$_2$, 0-50% EtOAc/hex) to afford 735 mg of the title compound as a mixture on mono- and bis-Boc protected material, which was used without further purification.

Step 5: Preparation of 3-(2-Chlorobenzyl)-7-fluoro-5-(2-oxo-2,3-dihydro-1H-benzo[d]imidazol-5-yl)-1H-benzo[e][1,4]diazepin-2(3H)-one (II-1)

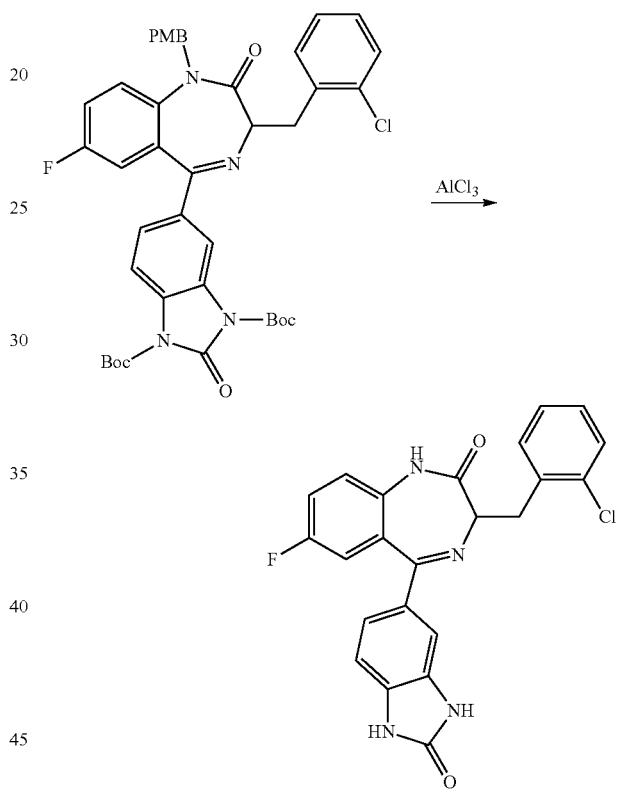

AlCl$_3$ (779 mg, 5.84 mmol, 6.0 equiv) was added to a solution of PMB-protected benzodiazepine (735 mg, 0.973 mmol) in anisole (9.7 mL). The resulting orange suspension was stirred at 40° C. for 14 h. The reaction mixture was cooled to rt and poured into ice water/EtOAc and stirred vigorously for 10 min. The organic phase was separated, washed with brine, dried (Na$_2$SO$_4$), filtered and concentrated. The residue was purified by silica gel chromatography (20 g SiO$_2$, 0-9% MeOH/CH$_2$Cl$_2$). The product was then slurried in CH$_3$CN, filtered and dried to afford 125 mg (30%) of the title compound. $^1$H NMR (500 MHz, DMSO-d$_6$) δ 3.48 (d, J=6.6 Hz, 2H), 3.76 (t, J=6.8 Hz, 1H), 6.93 (m, 2H), 7.05 (s, 1H), 7.11 (m, 1 H), 7.27 (m, 3H), 7.38 (m, 1H), 7.47 (M, 2H), 10.63, (s, 1H), 10.69 (s 1H), 10.84 (s, 1H); HPLC purity=98.3%, T$_R$=6.44 min (Waters C-18 column, 4.6×150 mm, 3.5 micron, 1.0 mL/min, 2 min 25% MeCN in H$_2$O (0.1% TFA), 10 min gradient of 25%-95% MeCN in H$_2$O (0.1% TFA), then 95% MeCN in H$_2$O (0.1% TFA) for 5 min); HRMS (ES$^+$) calc'd for C$_{23}$H$_{16}$ClFN$_4$O$_2$+H$_1$ 435.1024. found 435.1032.

Example 13

Representative General Procedures for Alkylation of Nitrogen atom on a Benzimidazolone Substituent to Provide Compound 7-Chloro-5-(3-ethyl-2-oxo-2,3-dihydro-1H-benzo[d]imidazol-5-yl)-1-methyl-3-(naphthalen-2-ylmethyl)-1H-benzo[e][1,4]diazepin-2(3H)-one (I-1)

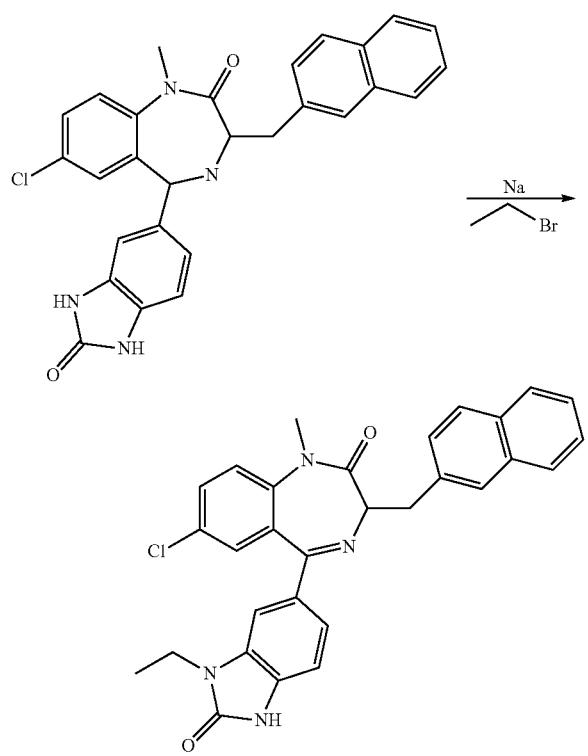

7-Chloro-1-methyl-3-(naphthalen-2-ylmethyl)-5-(2-oxo-2,3-dihydro-1H-benzo[d]imidazol-5-yl)-1H-benzo[e][1,4]diazepin-2(3H)-one (0.13 g, 0.27 mmol) was dissolved in anhydrous DMF (4 mL) and cooled to 0° C. under nitrogen. Sodium hydride (60% in oil, 10 mg, 0.27 mmol) was added and the mixture was stirred for 5 minutes. Ethyl bromide (20 μL, 0.27 mmol) was added. The mixture was allowed to warm to room temperature. After 15 minutes additional sodium hydride was added (10 mg). After another 1 hr, more sodium hydride (10 mg) and ethyl bromide (20 uL) were added. Stirring was continued for an additional 5 hours. Then, water was added, followed by the addition of ethyl acetate to form a mixture that partitioned. The aqueous layer from the mixture was extracted twice with ethyl acetate, and the combined extracts were washed with brine and then dried over anhydrous magnesium sulfate. The drying agent was removed and the solvents evaporated. Chromatography on silica gel gave four components, which were assigned by NMR spectroscopy and mass spectroscopy.

One component was identified as 7-chloro-5-(3-ethyl-2-oxo-2,3-dihydro-1H-benzo[d]imidazol-5-yl)-1-methyl-3-(naphthalen-2-ylmethyl)-1H-benzo[e][1,4]diazepin-2(3H)-one (I-1). $^1$H NMR (400 MHz, CDCl$_3$) δ 1.3 (t, 3H), 1.6 (s, 3H), 3.4 (s, 3H), 3.6-3.82 (m, 3H), 3.9 (q, 2H), 7.0-7.1 (m, 3H), 7.2-7.4 (m, 2H), 7.4-7.6 (m, 4H), 7.6-7.75 (m, 1H), 7.75-7.9 (m, 4H), 9.2 (s, 1H). ESI m/z 509 (M+1)$^+$.

Another component was identified as 7-chloro-5-(1-ethyl-2-oxo-2,3-dihydro-1H-benzo[d]imidazol-5-yl)-1-methyl-3-(naphthalen-2-ylmethyl)-1H-benzo[e][1,4]diazepin-2(3H)-one. $^1$H NMR (400 MHz, CDCl$_3$) δ 1.3 (t, 3H), 1.6 (s, 3H), 3.4 (s, 3H), 3.6-3.82 (m, 3H), 3.9 (q, 2H), 6.98 (m, 1H), 7.2-7.4 (m, 4H), 7.4-7.6 (m, 4H), 7.75-7.9 (m, 4H), 8.6 (s, 1H); ESI m/z 509 (M+1)$^+$.

Example 14

Representative Procedures for Synthesis of 6-Chloro-8-methoxy-1H-benzo[d][1,3]oxazine-2,4-dione

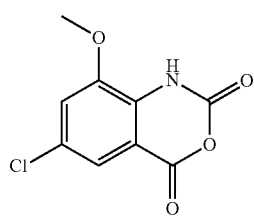

The title compound was prepared according to the following procedures.

Step 1: Preparation of 8-Methoxy-1H-benzo[d][1,3]oxazine-2,4-dione

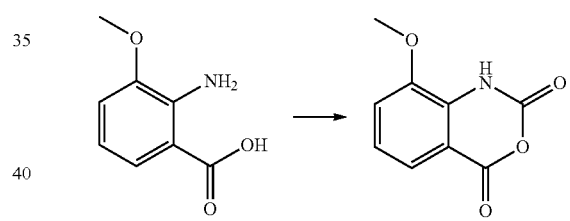

To 2-amino-3-methoxybenzoic acid (5 g, 30 mmol) in anhydrous tetrahydrofuran (50 mL) was added triphosgene (3.55 g, 12 mmol). This mixture was heated to reflux under a nitrogen atmosphere for 3 hours. It was cooled to ambient temperature, and diethyl ether (50 mL) was added. The mixture was filtered to yield 8-methoxy-1H-benzo[d][1,3]oxazine-2,4-dione (5.25 g, 91%) as a solid.

Step 2: Preparation of Methyl 2-amino-3-methoxybenzoate

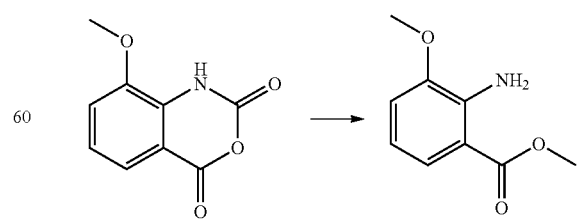

To 8-methoxy-1H-benzo[d][1,3]oxazine-2,4-dione (0.8 g, 4.1 mmol) in anhydrous methanol (25 mL), was added sodium hydroxide (0.24 g, 4.1 mmol) and the mixture was heated to reflux for 2 hours. The solution was cooled, diluted with ethyl acetate, washed with water, saturated sodium bicarbonate, then brine, and dried with sodium sulfate. It was filtered and concentrated to yield methyl 2-amino-3-methoxybenzoate (750 mg, 100%).

Step 3: Preparation of Methyl 2-amino-5-chloro-3-methoxybenzoate

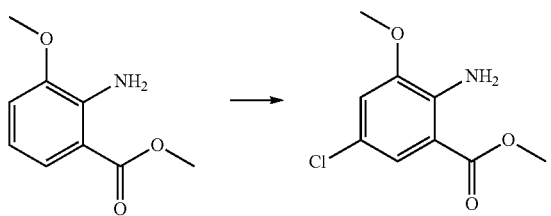

To methyl 2-amino-3-methoxybenzoate (750 mg, 4.1 mmol) in anhydrous N,N-dimethylformamide (15 mL) was added N-chlorosuccinimide (580 mg, 4.35 mmol) and this mixture was stirred at ambient temperature for 2 hours. The temperature was increased to 60° C. for 4 hours. The deep red solution was cooled, diluted with ethyl acetate, washed with saturated sodium bicarbonate, water, then brine, dried with sodium sulfate, decanted and concentrated to yield crude methyl 2-amino-5-chloro-3-methoxybenzoate (0.85 g, 95%). MS (m/z): 216.1 (M+H)$^+$.

Step 4: Preparation of 2-Amino-5-chloro-3-methoxybenzoic acid

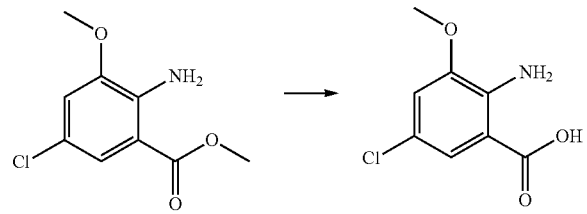

Methyl 2-amino-5-chloro-3-methoxybenzoate (770 mg, 3.57 mmol) was suspended in tetrahydrofuran (20 mL), 2M sodium hydroxide (5 mL) was added and the mixture was stirred at ambient temperature for 20 hours. The solution was concentrated in vacuo, then partitioned between ethyl acetate and 1M hydrochloric acid. The organic layer was washed with water, then brine, dried with sodium sulfate, decanted and concentrated in vacuo to yield 2-amino-5-chloro-3-methoxybenzoic acid.

Step 5: Preparation of 6-Chloro-8-methoxy-1H-benzo[d][1,3]oxazine-2,4-dione

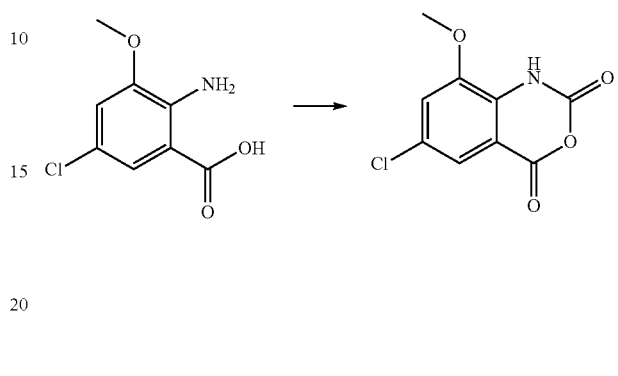

To 2-amino-5-chloro-3-methoxybenzoic acid (0.72 g, 3.57 mmol) in anhydrous tetrahydrofuran (15 mL) was added triphosgene (0.53 g, 1.8 mmol). The mixture was heated to refluxed under a nitrogen atmosphere for 2.5 hours. The resulting solution was cooled to ambient temperature, diethyl ether (10 mL) was added, which caused a solid to precipitate. The solid was collected by filtration and washed with more diethyl ether to yield 6-chloro-8-methoxy-1H-benzo[d][1,3] oxazine-2,4-dione. MS (m/z): 226.3, 228.3 (M+H)$^+$.

The following compound was prepared based on the above procedures and substituting compound 2-amino-3-fluorobenzoic acid for compound 2-amino-3-methoxybenzoic acid in Step 1: 6-Chloro-8-fluoro-1H-benzo[d][1,3]oxazine-2,4-dione.

Example 15

Representative General Procedure for Conversion of a Methyl Ether to a Phenol

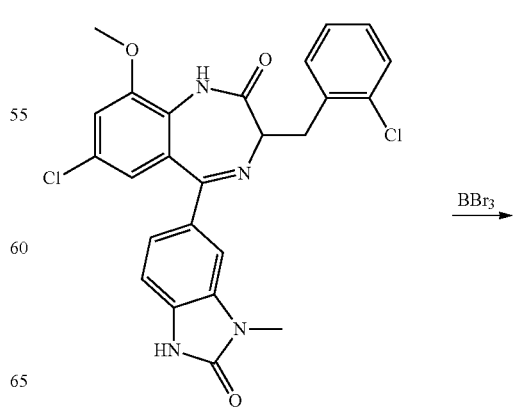

-continued

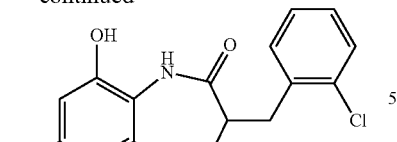

To 7-chloro-3-(2-chlorobenzyl)-9-methoxy-5-(3-methyl-2-oxo-2,3-dihydro-1H-benzo[d]imidazol-5-yl)-1H-benzo[e][1,4]diazepin-2(3H)-one (25 mg, 0.05 mmol) under a nitrogen atmosphere was added 1M boron tribromide solution in dichloromethane (3 mL). This mixture was stirred at ambient temperature for 1 hour, then quenched with water (30 mL). Ethyl acetate (30 mL) was added and the mixture was slurried overnight. The layers were separated and the organic layer was dried with sodium sulfate, filtered and concentrated in vacuo. The product was purified by column chromatography eluting with a gradient of 0-20% methanol in dichloromethane to yield 7-chloro-3-(2-chlorobenzyl)-9-hydroxy-5-(3-methyl-2-oxo-2,3-dihydro-1H-benzo[d]imidazol-5-yl)-1H-benzo[e][1,4]diazepin-2(3H)-one. HRMS [M+H]$^+$ predicted: 481.0834. found: 481.0828.

Example 16

Representative Procedures for the Synthesis of 7-Chloro-3-(2-chloro-4-fluorobenzyl)-5-(4-hydroxy-3-methylphenyl)-1H-benzo[e][1,4]diazepin-2(3H)-one (III-4)

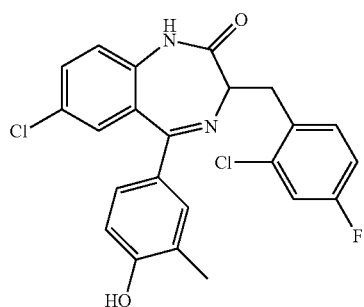 [SMILES: Cc1cc(C2=NC(Cc3ccc(F)cc3Cl)C(=O)Nc3ccc(Cl)cc32)ccc1O]

The title compound was prepared according to the following procedures.

Step 1: Representative Procedures for Alkylation at the C3-Position of the Benzodiazepine

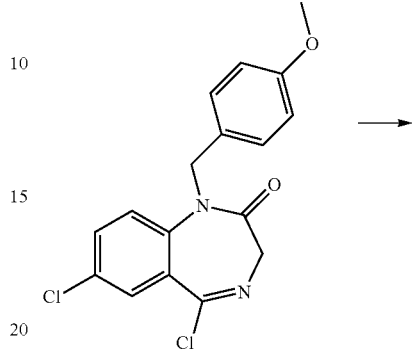

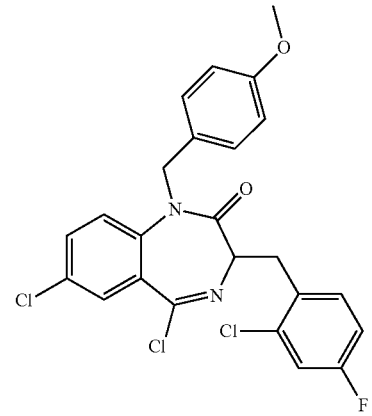

5,7-Dichloro-1-(4-methoxybenzyl)-1H-benzo[e][1,4]diazepin-2(3H)-one (0.85 g, 3.82 mmol) was dissolved in anhydrous tetrahydrofuran (15 mL) and cooled to −78° C. under nitrogen. Potassium tert-butoxide (0.48 g, 3.82 mmol) was dissolved in anhydrous tetrahydrofuran (4 mL) and added to the benzodiazepine via syringe. After 2 minutes, a solution of the 2-chloro-4-fluorobenzyl bromide (1.27 g, 3.64 mmol) in anhydrous tetrahydrofuran (3 mL) was added. The reaction mixture was stirred at −78° C. for 2 then allowed to warm to room temperature over 1 h. The reaction was quenched with water and the layers partitioned. The organic layer was evaporated onto silica gel and chromatographed eluting with 10-35% ethyl acetate in hexanes to obtain 5,7-dichloro-3-(2-chloro-4-fluorobenzyl)-1-(4-methoxybenzyl)-1H-benzo[e][1,4]diazepin-2(3H)-one (0.6 g, 1.22 mmol).

Step 2: Representative Procedures for Installing a Protected Phenol at the C5-Position of a Benzodiazepine Step 3: Representative Procedures for O-Demethylation of a Protected Phenol at the C5-Position of the Benzodiazepine

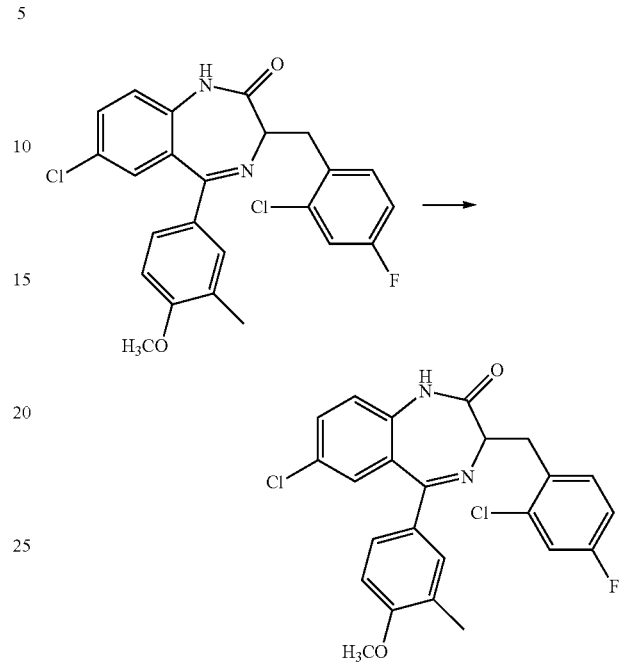

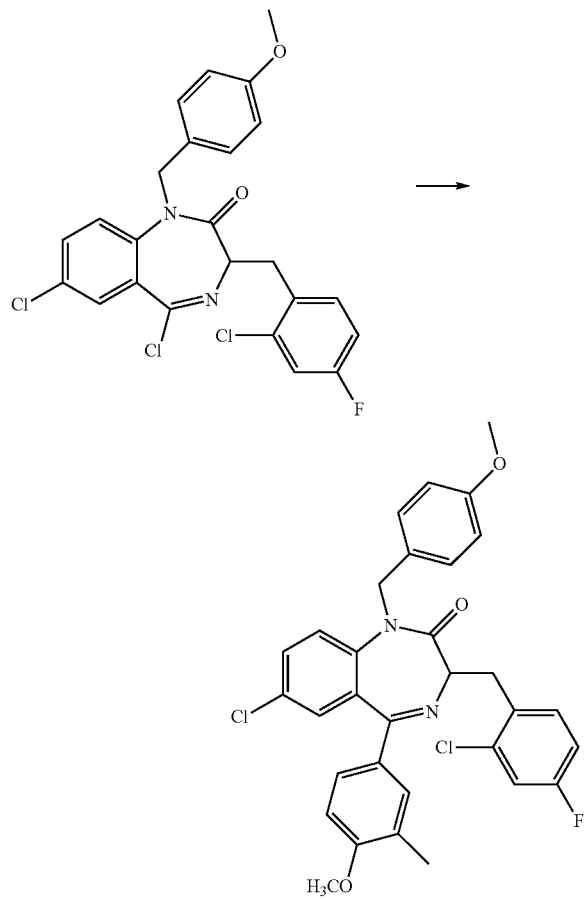

5,7-Dichloro-3-(2-chloro-4-fluorobenzyl)-1-(4-methoxybenzyl)-1H-benzo[e][1,4]diazepin-2(3H)-one (0.3 g, 0.61 mmol) was combined with lithium chloride (0.078 g, 1.83 mmol), cesium hydroxide hydrate (0.31 g, 1.83 mmol) and 2-(4-methoxy-3-methylphenyl)-4,4,5,5-tetramethyl-1,3,2-dioxaborolane (0.151 g, 0.61 mmol) in 1,4-dioxane (3 mL) and water (0.3 mL) and the mixture was purged with nitrogen. [Tetrakis(triphenylphosphine)]palladium(0) (0.07 g, 0.061 mmol) was added and the mixture was heated in a CEM Discover microwave reactor at 160° C. for 20 minutes. The mixture was allowed to cool and diluted with ethyl acetate then washed with water then brine. The organic layer was concentrated onto silica gel and chromatographed on a silica gel column eluting with 10-35% ethyl acetate in hexanes to give 7-chloro-3-(2-chloro-4-fluorobenzyl)-5-(4-methoxy-3-methylphenyl)-1-(4-methoxybenzyl)-1H-benzo[e][1,4]diazepin-2(3H)-one.

7-Chloro-3-(2-chloro-4-fluorobenzyl)-5-(4-methoxy-3-methylphenyl)-1H-benzo[e][1,4]diazepin-2(3H)-one (0.158 g, 0.345 mmol) was dissolved in dichloromethane (DCM, 2 mL) and BBr$_3$ in DCM (1 M, 1.73 mL, 1.73 mmol) was added dropwise. The mixture was stirred at room temperature for 4 h. then quenched with methanol and diluted with ethyl acetate. The organic solution was washed with saturated sodium bicarbonate (aq) then brine. It was concentrated onto silica gel then chromatographed on silica gel eluting with 35-40-45% ethyl acetate in hexanes to give 7-chloro-3-(2-chloro-4-fluorobenzyl)-5-(4-hydroxy-3-methylphenyl)-1H-benzo[e][1,4]diazepin-2(3H)-one as a yellow oil which precipitated as a pale yellow solid from chloroform (158 mg, 0.345 mmol).

Based on the foregoing procedures, the following compounds were also prepared:

7-Chloro-3-(2-chloro-5-fluorobenzyl)-5-(4-methoxy-3-methylphenyl)-1H-benzo[e][1,4]diazepin-2(3H)-one MS (m/z): 457.1 (M+1)$^+$;

7-Chloro-3-(2-chloro-5-fluorobenzyl)-5-(4-methoxy-3-methylphenyl)-1-(4-methoxybenzyl)-1H-benzo[e][1,4]diazepin-2(3H)-one MS (m/z): 577.3 (M+1)$^+$;

5,7-Dichloro-3-(2-chloro-5-fluorobenzyl)-1-(4-methoxybenzyl)-1H-benzo[e][1,4]diazepin-2(3H)-one MS (m/z): 529.2 (M+K)$^+$;

7-Chloro-3-(2-chloro-5-fluorobenzyl)-5-(4-hydroxy-3-methylphenyl)-1H-benzo[e][1,4]diazepin-2(3H)-one (III-2)

MS (m/z): 443.1 (M+1)$^+$. $^1$HNMR (DMSO-d$_6$, 400 MHz) δ 10.72 (s, 1H), 9.88 (s, 1H), 7.60 (dd, J=8.8, 1.6 Hz, 1H), 7.42 (dd, J=8.8, 5.2 Hz, 1H), 7.34 (dd, J=10, 3.2 Hz, 1H), 7.23-7.15 (m, 3H), 7.10 (dt, J=8.4, 2.8 Hz, 1H), 6.94 (dd, J=8.4, 2 Hz, 1H), 6.74 (d, J=8.4 Hz, 1H), 3.71 (dd, J=8.4, 4.8 Hz, 1H), 3.53-3.39 (m, 2H), 2.08 (s, 3H);

7-Chloro-3-(4-chlorobenzyl)-5-(4-methoxy-3-methylphenyl)-1-(4-methoxybenzyl)-1H-benzo[e][1,4]diazepin-2(3H)-one MS (m/z): 559.3 (M+1)$^+$;

7-Chloro-3-(4-chlorobenzyl)-5-(4-methoxy-3-methylphenyl)-1H-benzo[e][1,4]diazepin-2(3H)-one MS (m/z): 439.0 (M+1)$^+$;

7-Chloro-3-(4-chlorobenzyl)-5-(4-hydroxy-3-methylphenyl)-1H-benzo[e][1,4]diazepin-2(3H)-one (III-3)

MS (m/z): 425.2 (M+1)$^+$. $^1$HNMR (DMSO-d$_6$, 400 MHz) δ 10.71 (s, 1H), 9.94 (s, 1H), 7.66 (dd, J=8.8 Hz, 1H), 7.42 (d, J=8.4 Hz, 2H), 7.38 (d, J=8.4 Hz, 2H), 7.29-7.22 (m, 3H), 7.08 (dd, J=8, 2 Hz, 1H), 6.85 (d, J=8 Hz, 1H), 3.69 (t, J=8 Hz, 1H), 3.39-3.29 (m, 2H), 2.18 (s, 3H);

7-Chloro-3-(2-chloro-4-fluorobenzyl)-5-(4-hydroxy-3-methylphenyl)-1H-benzo[e][1,4]diazepin-2(3H)-one (III-4)

$^1$HNMR (400 MHz, D$_6$-DMSO) δ 2.09 (s, 3H), 3.30-3.47 (m, 2H), 3.68 (dd, 1H), 6.75 (d, 1H), 6.97 (dd, 1H), 7.12-7.23 (m, 4H), 7.35 (dd, 1H), 7.51 (dd, 1H), 7.59 (dd, 1H), 9.85 (br s, 1H), 10.68 (s, 1H); ESI m/z 443.1 (M+);

7-Chloro-5-(4-hydroxy-3-methylphenyl)-3-(2-(trifluoromethyl)benzyl)-1H-benzo[e][1,4]diazepin-2(3H)-one (III-5)

$^1$H NMR (400 MHz, CDCl$_3$) δ 2.22 (s, 3H), 3.71-3.75 (m, 2H), 3.79-3.83 (m, 1H), 6.1 (br s, 1H), 6.68 (d, 1H), 7.03 (d, 1H), 7.11 (d, 1H), 7.24-7.27 (m, 2H), 7.32 (t, 1H), 7.42 (d, 1H), 7.51 (t, 1H), 7.60 (d, 1H), 7.78 (d, 1H), 9.23 (br s, 1H); ESI m/z 459.2 (M+1$^+$);

7-Chloro-5-(4-hydroxy-3-methylphenyl)-3-(4-(trifluoromethyl)benzyl)-1H-benzo[e][1,4]diazepin-2(3H)-one (III-6)

$^1$H NMR (400 MHz, D$_6$-DMSO) δ 2.09 (s, 3H), two protons buried under HDO peak, 3.74 (t, 1H), 6.78 (d, 1H), 7.01 (d, 1H), 7.15 (d, 1H), 7.22 (dd, 2H), 7.42 (d, 2H), 7.60 (dd, 1H), 7.82 (d, 2H), 9.90 (br s, 1H), 10.69 (s, 1H); and 2-(5-(7-Chloro-3-(3,4-diethylbenzyl)-2-oxo-2,3-dihydro-1H-benzo[e][1,4]diazepin-5-yl)-2-hydroxyphenyl)acetamide (III-1).

Example 17

Representative Procedure for Preparation of (R)-7-Chloro-3-(2-chlorobenzyl)-5-(4-hydroxy-3-methylphenyl)-1H-benzo[e][1,4]diazepin-2(3H)-one (IV-6)

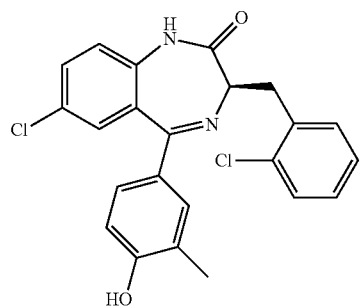 [SMILES: Cc1cc(C2=N[C@H](Cc3ccccc3Cl)C(=O)Nc3ccc(Cl)cc32)ccc1O]

The title compound was prepared according to the procedures shown in the scheme below. Compound 5-chloroisatoic anhydride (A) was reacted with (R)-2-chlorophenylalanine to provide benzodiazepine-dione B based on procedures described in, for instance, Example 2. Reaction of benzodiazepine-dione B with para-methoxybenzyl chloride in the presence of base, according to procedures described in, for instance, Example 3, provided PMB-protected benzodiazepine-dione C. Conversion of benzodiazepine-dione C to imidoyl chloride D was accomplished using phosphorous oxychloride, based on procedures described in, for instance, Example 4. The substituted phenyl group was installed using Suzuki coupling, based on procedures described in, for instance, Example 7, to provide benzodiazepine E. The PMB protecting group was removed by reacting benzodiazepine E with AlCl$_3$, based on procedures described in, for instance, Example 8, to provide benzodiazepine F. Methyl phenyl ether F was converted to phenol G using boron tribromide, based on procedures described in, for instance, Example 16.

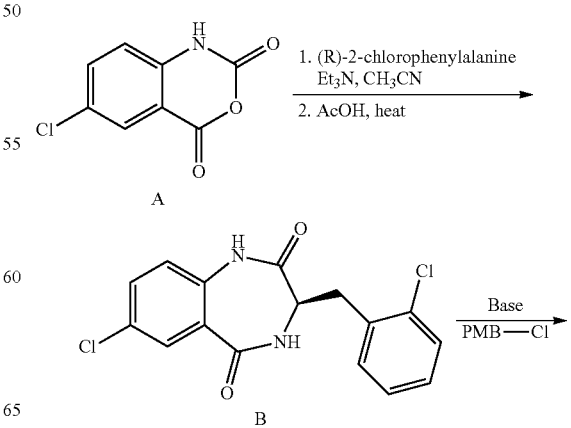

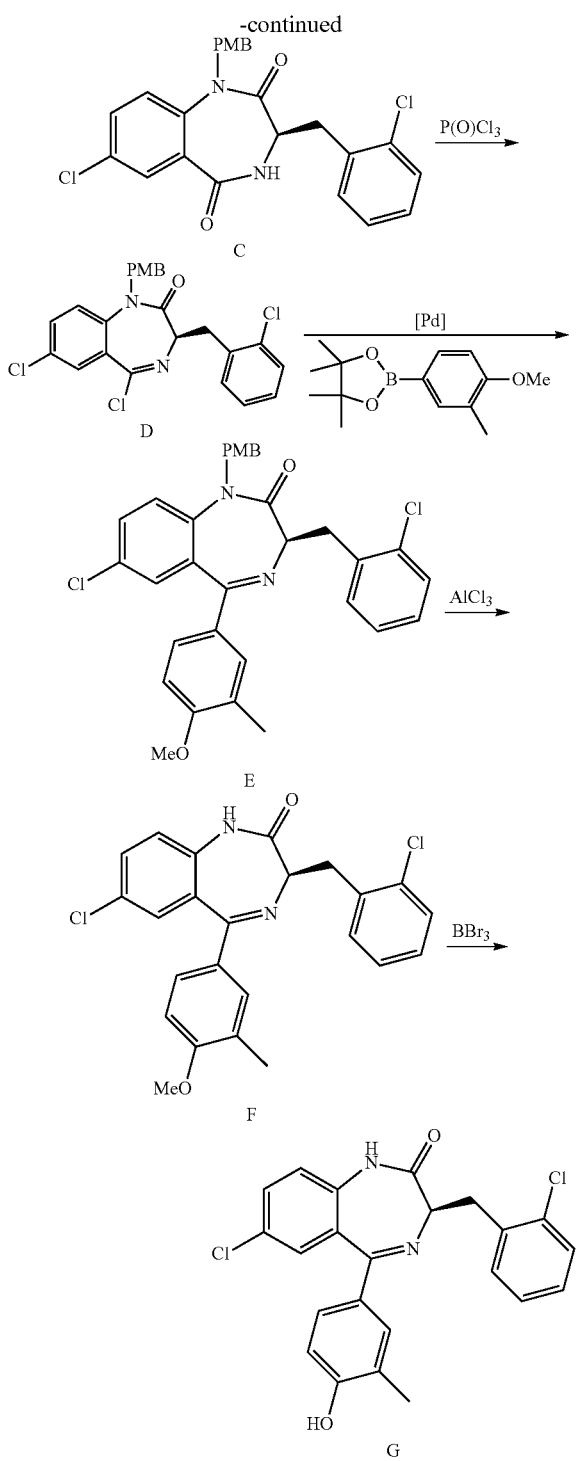

Physical Characterization Data for Compound (R)-7-Chloro-3-(2-chlorobenzyl)-5-(4-hydroxy-3-methylphenyl)-1H-benzo[e][1,4]diazepin-2(3H)-one (IV-6)

MS (m/z): 425.2 (M+1)⁺. ¹HNMR (DMSO-d₆, 400 MHz) δ 10.68 (s, 1H), 9.84 (s, 1H), 7.58 (dd, J=8.8, 2.4 Hz, 1H), 7.46 (dd, J=7.2, 1.6 Hz, 1H), 7.36 (dd, J=8, 1.6 Hz, 1H), 7.27 (dt, J=7.6, 1.6 Hz, 1H), 7.23 (s, 1H), 7.21-7.19 (m, 2H), 7.13 (d, J=1.6 Hz, 1H), 6.97 (dd, J=8.4, 2.4 Hz, 1H), 6.74 (d, J=8.4 Hz, 1H), 3.68 (t, J=6.8 Hz, 1H), 3.44 (d, J=7.2 Hz, 2H), 2.08 (s, 3H).

Physical Characterization Data for Synthetic Intermediate Compounds: (R)-7-Chloro-3-(2-chlorobenzyl)-5-(4-methoxy-3-methylphenyl)-1-(4-methoxybenzyl)-1H-benzo[e][1,4]diazepin-2(3H)-one. MS (m/z): 559.3 (M+1)⁺; and (R)-7-Chloro-3-(2-chlorobenzyl)-5-(4-methoxy-3-methylphenyl)-1H-benzo[e][1,4]diazepin-2(3H)-one. MS (m/z): 439.2 (M+1)⁺.

The following compound was prepared by making appropriate substitutions to the above synthetic procedure:

(S)-7-Chloro-3-(2-chlorobenzyl)-5-(4-hydroxy-3-methylphenyl)-1H-benzo[e][1,4]diazepin-2(3H)-one
(IV-5)

¹H NMR (400 MHz, CDCl₃) δ 2.22 (s, 3H), 3.62 (dd, 2H), 3.73 (m, 1H), 3.85 (m, 1H), 5.31 (br s, 1H), 6.67 (d, 1H), 7.04 (dd, 1H), 7.06 (d, 1H), 7.18 (m, 1H), 7.23-7.27 (m, 3H), 7.31 (dd, 1H), 7.44 (dd, 1H), 7.60 (dd, 1H), 8.78 (s, 1H).

Example 18

Representative Procedure for Preparation of (R)-7-Chloro-3-(2-chlorobenzyl)-5-(3-methyl-2-oxo-2,3-dihydro-1H-benzo[d]imidazol-5-yl)-1H-benzo[e][1,4]diazepin-2(3H)-one (IV-1)

The title compound was prepared according to the procedures shown in the scheme below. Compound 5-chloroisatoic anhydride (A) was reacted with (R)-2-chlorophenylalanine to provide benzodiazepine-dione B based on procedures described in, for instance, Example 2. Reaction of benzodiazepine-dione B with para-methoxybenzyl chloride in the presence of base, according to procedures described in, for instance, Example 3, provided PMB-protected benzodiazepine-dione C. Conversion of benzodiazepine-dione C to imidoyl chloride D was accomplished using phosphorous oxychloride, based on procedures described in, for instance, Example 4. The benzimidazolone substituent was installed using Suzuki coupling, based on procedures described in, for instance, Example 7, to provide benzodiazepine E. Removal of the PMB protecting group was accomplished by reacting benzodiazepine E with AlCl₃, based on procedures described in, for instance, Example 8, to provide benzodiazepine F.

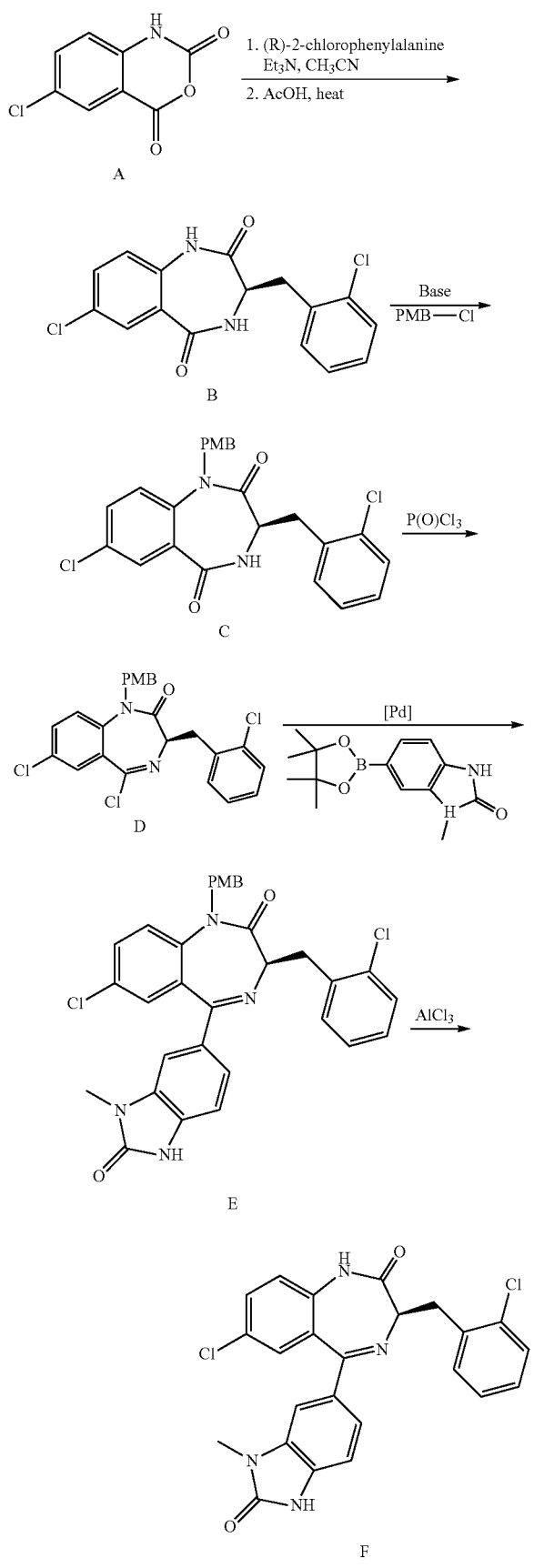

Physical Characterization Data for Compound (R)-7-Chloro-3-(2-chlorobenzyl)-5-(3-methyl-2-oxo-2,3-dihydro-1H-benzo[d]imidazol-5-yl)-1H-benzo[e][1,4]diazepin-2(3H)-one (IV-1)

Optical rotation data: C=1.0 (CHCl$_3$), [α]$_D$=+73°; MS (m/z): 465.1; $^1$H NMR (d$^6$-DMSO) δ 11.08 (s, 1H), 10.75 (s, 1H), 7.63 (m, 1H), 7.53 (m, 1H), 7.40 (m, 1H), 7.33-7.22 (m, 4H), 7.12 (m, 1H), 6.96 (m, 1H), 6.89 (m, 1H) 3.76 (m, 1H), 3.56-3.42 (m, 2H), 3.26 (s, 1H).

The following compounds were prepared based on the above general procedures: For example, compound (S)-7-chloro-3-(2-chlorobenzyl)-5-(3-methyl-2-oxo-2,3-dihydro-1H-benzo[d]imidazol-5-yl)-1H-benzo[e][1,4]diazepin-2 (3H)-one (IV-2) was prepared by using (S)-2-chlorophenylalanine in place of (R)-2-chlorophenylalanineL Optical rotation data: C=1.0 (CHCl$_3$), [α]$_D$=−62°; MS (m/z): 465.1, 467.1; $^1$H NMR (d$^6$-DMSO) δ 11.08 (s, 1H), 10.75 (s, 1H), 7.63 (m, 1H), 7.53 (m, 1H), 7.40 (m, 1H), 7.33-7.23 (m, 4H), 7.13 (m, 1H), 6.96 (m, 1H), 6.89 (m, 1H) 3.76 (m, 1H), 3.56-3.42 (m, 2H), 3.26 (s, 1H);

7-Chloro-3-(2-chlorobenzyl)-5-(3-methyl-2-oxo-2,3-dihydro-1H-benzo[d]imidazol-5-yl)-1H-benzo[e][1,4]diazepin-2(3H)-one (I-2)

HRMS calc.=465.0885 g/mol, HRMS obs.=465.0882 g/mol; $^1$H NMR (d$^6$-DMSO) δ 11.07 (br s, 1H), 10.75 (br s, 1H), 7.64-7.51 (m, 3H), 7.41-7.21 (m, 4H), 7.1-6.9 (m, 3H), 3.75 (m, 1H), 3.47 (m, 2H);

2-(6-(7-Chloro-3-(2-chlorobenzyl)-2-oxo-2,3-dihydro-1H-benzo[e][1,4]diazepin-5-yl)-2-oxo-2,3-dihydro-1H-benzo[d]imidazol-1-yl)acetic acid (I-3)

HRMS calc.=509.0783 g/mol, HRMS obs. 509.0771 g/mol; $^1$H NMR (d$^6$-DMSO) δ 11.22 (s, 1H), 10.76 (s, 1H), 7.63 (dd, 1H), 7.53 (m, 1H), 7.39 (m, 1H) 7.32-7.16 (m, 5H), 7.0 (m, 1H), 6.92 (m, 1H), 4.54 (m, 2H), 3.73 (m, 1H), 3.45 (m, 2H);

2-(6-(7-Chloro-3-(2-chlorobenzyl)-2-oxo-2,3-dihydro-1H-benzo[e][1,4]diazepin-5-yl)-2-oxo-2,3-dihydro-1H-benzo[d]imidazol-1-yl)-N-methylacetamide (I-4)

HRMS calc.=522.1100 g/mol, HRMS obs.=522.1100 g/mol;

7-Chloro-3-(2-chlorobenzyl)-5-(3-(3-hydroxypropyl)-2-oxo-2,3-dihydro-1H-benzo[d]imidazol-5-yl)-1H-benzo[e][1,4]diazepin-2(3H)-one (I-5)

HRMS calc.=509.1147 g/mol, HRMS obs. 509.1139 g/mol; $^1$H NMR (d$^6$-DMSO) δ 11.09 (br s, 1H), 10.76 (br s, 1H), 7.65-7.54 (m, 6H), 6.96 (m, 1H), 6.85 (m, 1H), 4.56 (m, 1H), 3.8 (br m, 3H), 3.45 (br m, 3H), 1.77 (br m, 2H);

7-Chloro-3-(2-chlorobenzyl)-5-(3-(2-hydroxyethyl)-2-oxo-2,3-dihydro-1H-benzo[d]imidazol-5-yl)-1H-benzo[e][1,4]diazepin-2(3H)-one (I-6)

HRMS calc.=495.0991 g/mol, HRMS obs.=495.0986 g/mol;

7-Chloro-3-(2-chlorobenzyl)-9-methoxy-5-(3-methyl-2-oxo-2,3-dihydro-1H-benzo[d]imidazol-5-yl)-1H-benzo[e][1,4]diazepin-2(3H)-one (I-9)

HRMS calc.=495.0991 g/mol, HRMS obs.=495.0994 g/mol; $^1$H NMR (d$^6$-DMSO) δ 11.08 (s, 1H), 9.93 (s, 1H), 7.53 (dd, 1H), 7.40 (d, 1H), 7.38-7.22 (m, 3H), 7.14 (d, 1H), 6.94 (m, 2H), 6.80 (d, 1H), 3.91 (s, 3H), 3.75 (m, 1H), 3.5 (m, 2H), 3.26 (s, 3H);

7-Chloro-3-(2-chlorobenzyl)-9-hydroxy-5-(3-methyl-2-oxo-2,3-dihydro-1H-benzo[d]imidazol-5-yl)-1H-benzo[e][1,4]diazepin-2(3H)-one (I-10)

HRMS calc.=481.0834 g/mol, HRMS obs.=481.0828 g/mol;

7-Chloro-3-(2-chlorobenzyl)-1-methyl-5-(3-methyl-2-oxo-2,3-dihydro-1H-benzo[d]imidazol-5-yl)-1H-benzo[e][1,4]diazepin-2(3H)-one (I-11)

MS (m/z): 479.1; $^1$H NMR (d$^6$-DMSO) δ 9.79 (s, 1H), 7.75-7.40 (m, 4H), 7.40-6.95 (m, 6H), 3.90 (t, 1H), 3.72 (d, 2H), 3.45 (s, 3H), 3.42 (s, 3H); and 7-Chloro-3-(2-chlorobenzyl)-9-fluoro-5-(3-methyl-2-oxo-2,3-dihydro-1H-benzo[d]imidazol-5-yl)-1H-benzo[e][1,4]diazepin-2(3H)-one (I-12)

HRMS calc.=483.0791 g/mol, HRMS obs.=493.0801 g/mol; $^1$H NMR (d$^6$-DMSO) δ 11.06 (s, 1H), 10.63 (s, 1H), 7.72 (m, 1H), 7.47 (m, 1H), 7.36 (m, 1H), 7.28-7.20 (m, 2H), 7.1 (m, 2H), 6.92 (m, 2H) 3.84 (m, 1H), 3.5-3.35 (m, 2H), 3.27 (s, 1H).

Example 19

Representative compounds were tested for cytotoxicity in Ramos cells and inhibitory activity against ATPase. The Ramos cell death assay and ATPase inhibition assay were conducted as described in K. M. Johnson et al. *Chemistry & Biology* 2005, 12, 485-496. Results from the Ramos cell death assay and the ATPase inhibition assay are provided in Table 7.

TABLE 7

| Compound No. | ATPase IC$_{50}$ (μM) | Cell Death (Ramos Cells) (EC$_{50}$ μM) |
|---|---|---|
| I-1 | <7 | >7 |
| I-2 | <7 | <7 |
| I-3 | >7 | >7 |
| I-4 | >7 | >7 |
| I-5 | <7 | <7 |
| I-6 | >7 | <7 |
| I-7 | <7 | >7 |
| I-8 | <7 | >7 |
| I-9 | <7 | <7 |
| I-10 | <7 | >7 |
| I-11 | <7 | >7 |
| I-12 | <7 | >7 |
| I-13 | <7 | <7 |
| I-14 | <7 | <7 |
| II-1 | >7 | <7 |
| III-1 | >7 | <7 |
| III-2 | <7 | <7 |
| III-3 | <7 | <7 |
| III-4 | <7 | <7 |
| III-5 | <7 | <7 |

TABLE 7-continued

| Compound No. | ATPase IC$_{50}$ (μM) | Cell Death (Ramos Cells) (EC$_{50}$ μM) |
|---|---|---|
| III-6 | >7 | >7 |
| IV-1 | <7 | <7 |
| IV-2 | <7 | <7 |
| IV-3 | <7 | <7 |
| IV-4 | <7 | <7 |
| IV-5 | <7 | <7 |
| IV-6 | <7 | <7 |

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A compound represented by Formula I:

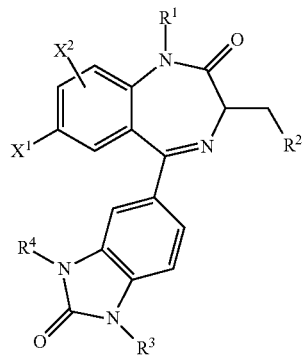

or a pharmaceutically acceptable salt thereof, wherein:
$X^1$ is Cl or F;
$X^2$ is hydrogen, halogen, hydroxyl, methoxy, ethoxy, methyl, or ethyl;
$R^1$ is hydrogen, $C_1$-$C_3$ alkyl, hydroxyethyl, or hydroxypropyl;
$R^2$ is

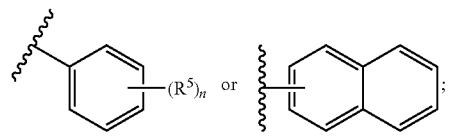

$R^3$ and $R^4$ are independently hydrogen, $C_1$-$C_5$ alkyl, or Z; provided that both $R^3$ and $R^4$ are not hydrogen, and provided that both $R^3$ and $R^4$ are not Z;

$R^5$ represents independently for each occurrence halogen, trifluoromethyl, or $C_1$-$C_5$ alkyl;

$R^6$ represents independently for each occurrence hydrogen or $C_1$-$C_5$ alkyl;

Z is $C_1$-$C_4$alkylene-$CO_2R^6$, $C_1$-$C_4$alkylene-$C(O)N(R^6)_2$, or $C_1$-$C_4$alkyl substituted with —$OR^6$;

n is 1 or 2; and the stereochemical configuration at a stereocenter in a compound represented by Formula I is R, S, or a mixture thereof.

2. The compound of claim 1, wherein $X^1$ is Cl.

3. The compound of claim 1, wherein $X^2$ is hydrogen or halogen.

4. The compound of claim 1, wherein $R^1$ is hydrogen.

5. The compound of claim 1, wherein $R^1$ is $C_1$-$C_3$ alkyl.

6. The compound of claim 1, wherein $R^2$ is

[structure: phenyl with $(R^5)_n$]

7. The compound of claim 6, wherein $R^5$ is halogen.

8. The compound of claim 6, wherein $R^5$ is chloro.

9. The compound of claim 8, wherein n is 1.

10. The compound of claim 1, wherein $R^3$ and $R^4$ are independently hydrogen or $C_1$-$C_5$ alkyl; provided that both $R^3$ and $R^4$ are not hydrogen.

11. The compound of claim 1, wherein the compound is represented by Formula IA:

IA

[structure of Formula IA]

or a pharmaceutically acceptable salt thereof, wherein:

$R^1$ is hydrogen, methyl, or ethyl;

$R^2$ is

[structures: phenyl with $(R^5)_n$ or naphthyl]

$R^3$ and $R^4$ are independently hydrogen, methyl, ethyl, propyl, butyl, or Z; provided that both $R^3$ and $R^4$ are not hydrogen, and provided that both $R^3$ and $R^4$ are not Z;

$R^5$ represents independently for each occurrence Cl or F;

Z is hydroxyethyl, hydroxylpropyl, or hydroxybutyl;

n is 1 or 2; and the stereochemical configuration at a stereocenter in a compound represented by Formula IA is R, S, or a mixture thereof.

12. The compound of claim 11, wherein $R^2$ is

[structure: phenyl with $(R^5)_n$]

13. The compound of claim 11, wherein $R^3$ and $R^4$ are independently hydrogen, methyl, ethyl, or propyl; provided that both $R^3$ and $R^4$ are not hydrogen.

14. The compound of claim 11, wherein $R^5$ is Cl, and n is 1.

15. A pharmaceutical composition comprising a compound of claim 1, or a pharmaceutically acceptable salt thereof, and a pharmaceutically acceptable carrier.

16. The compound of claim 1, wherein the compound is selected from the group consisting of:

[chemical structures]

103
-continued
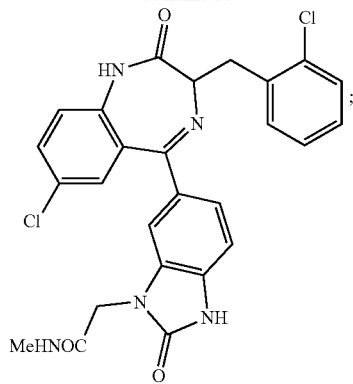
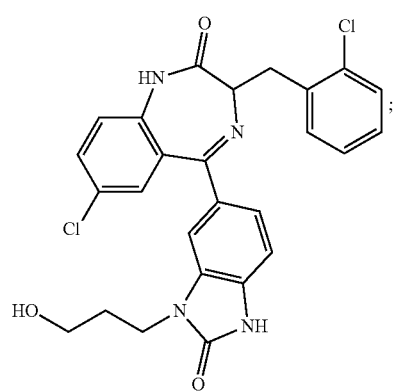
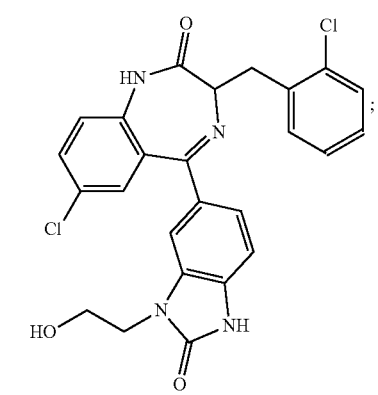
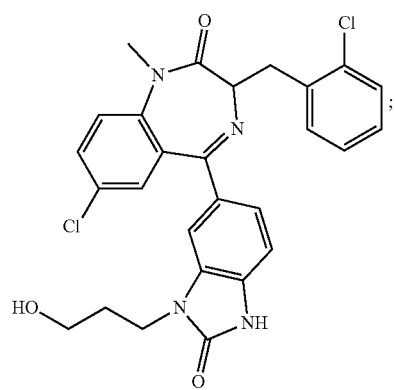
104
-continued
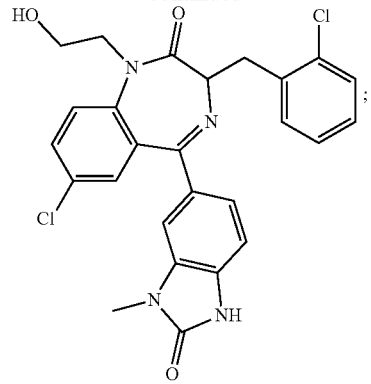
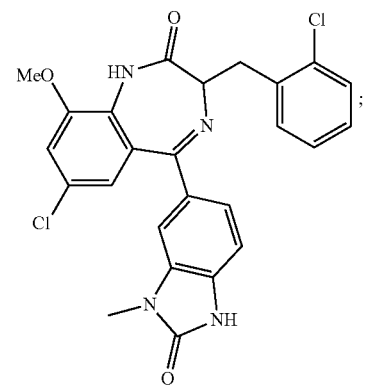
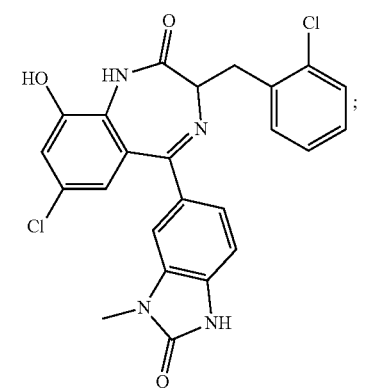
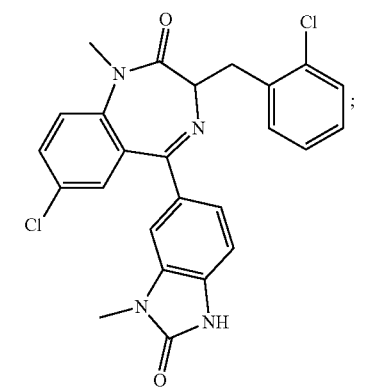

105                                       106
-continued                                -continued
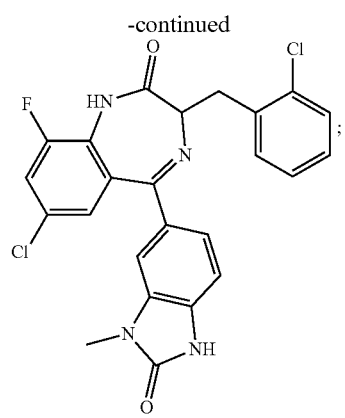
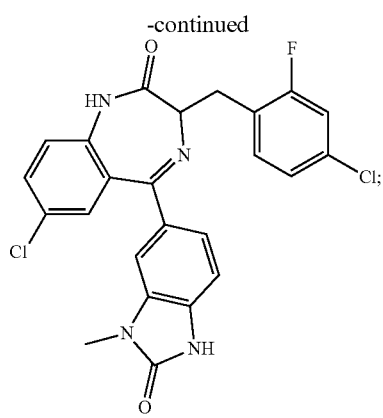
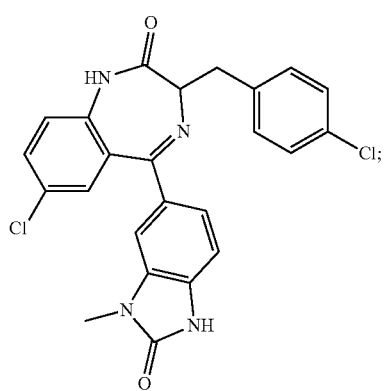
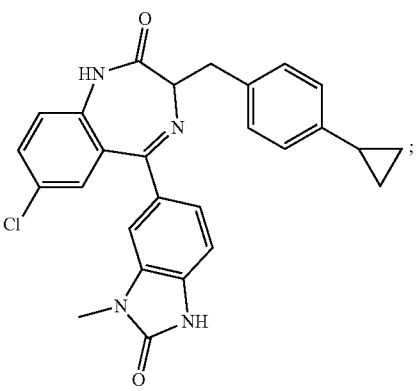
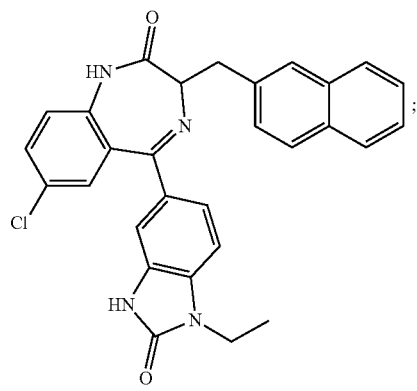
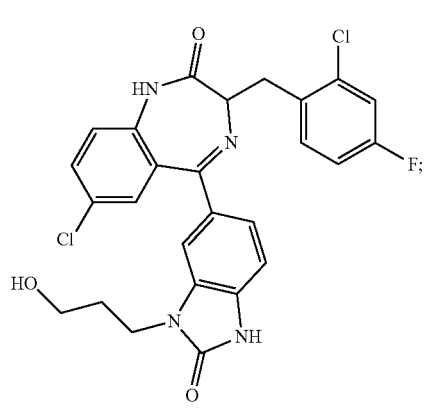
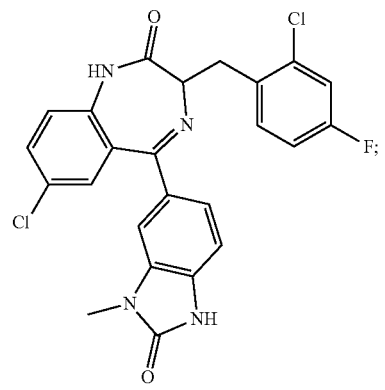
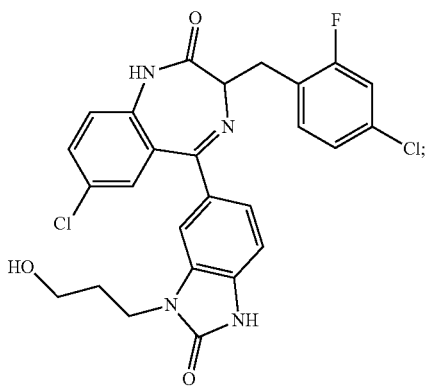

107
-continued
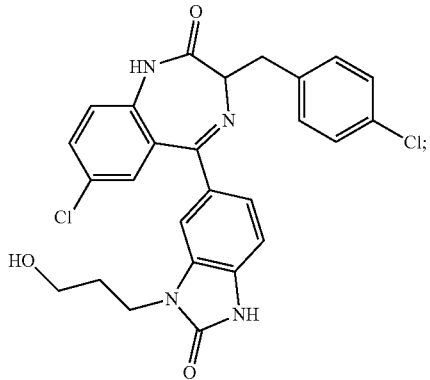
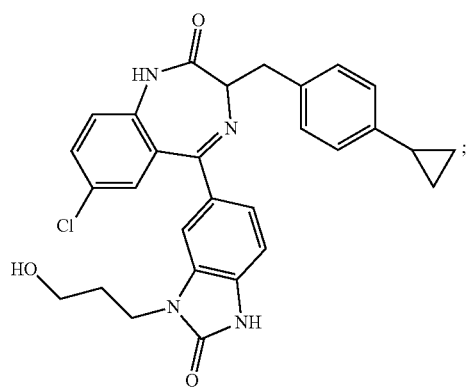
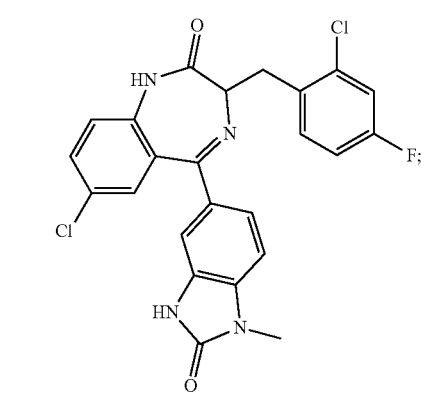
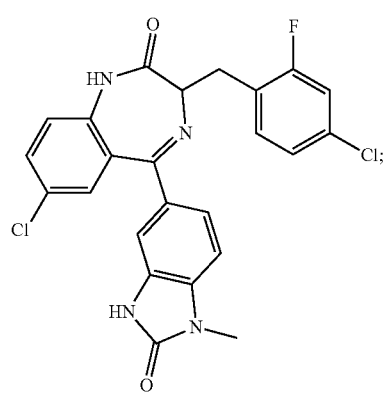
108
-continued
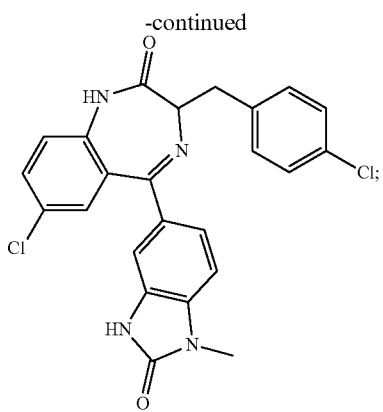
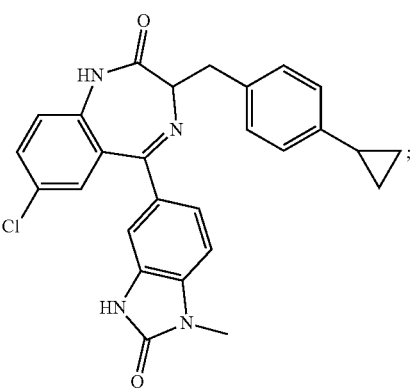
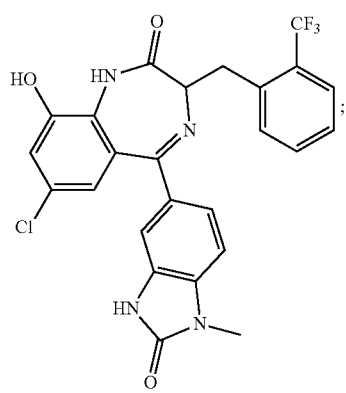
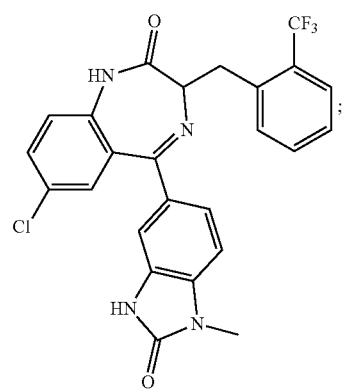

109
-continued
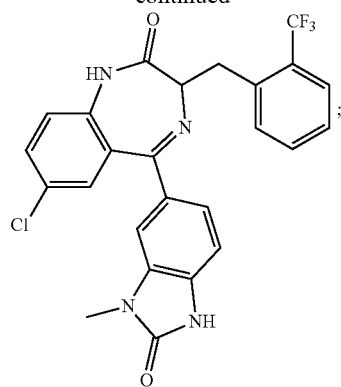
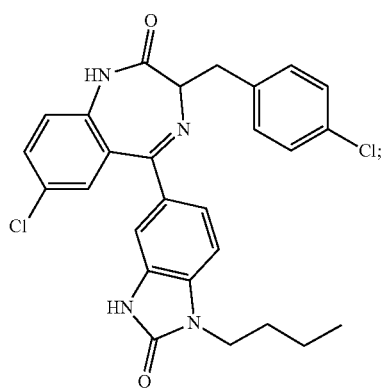
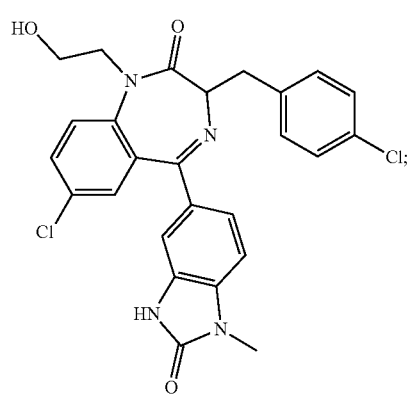
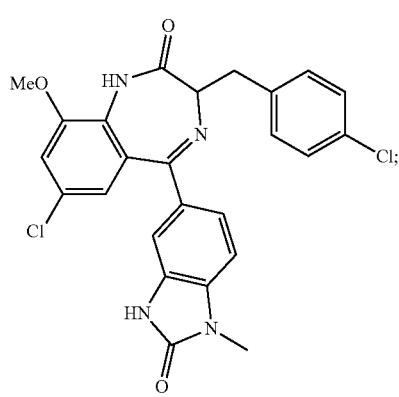
110
-continued
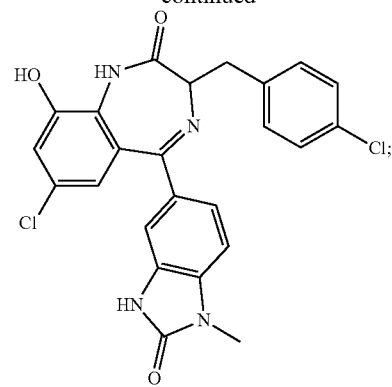
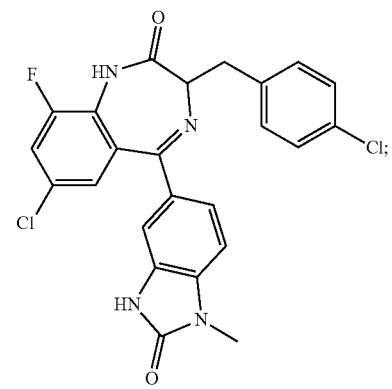
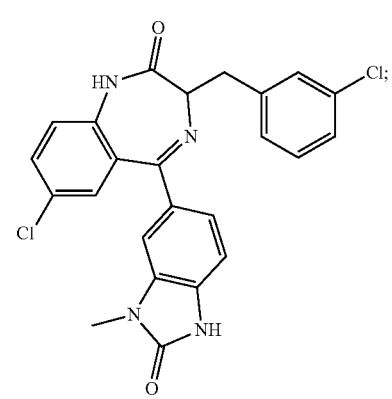
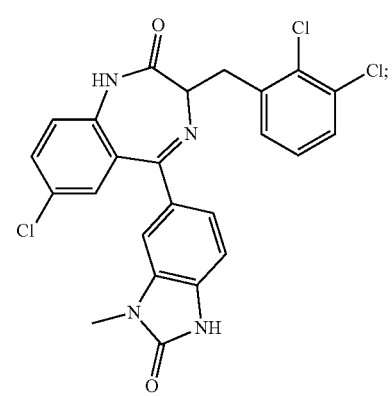

111
-continued
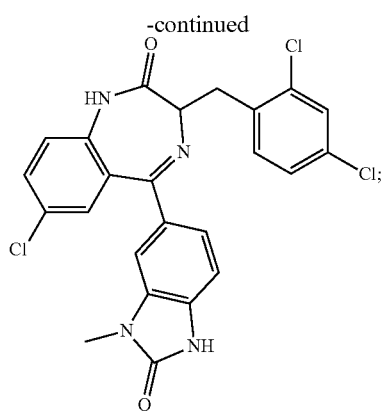
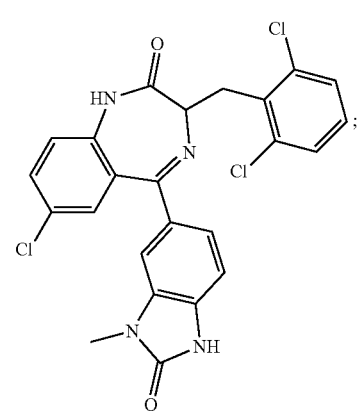
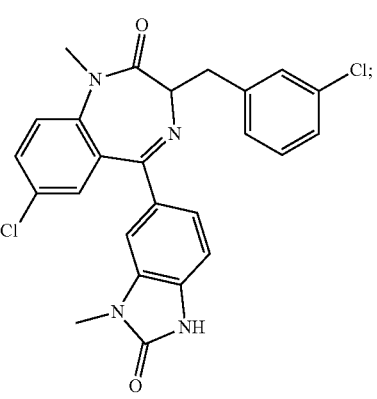
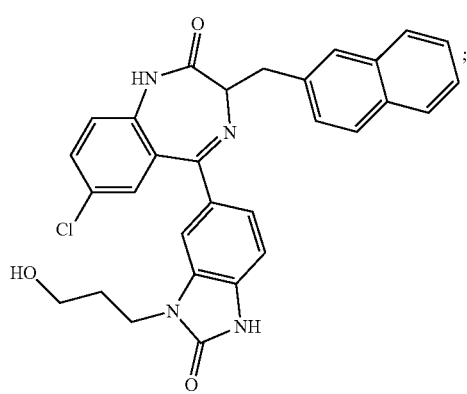
112
-continued
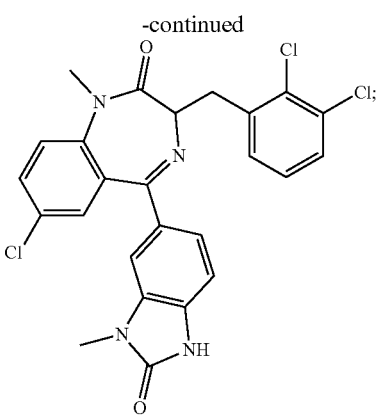
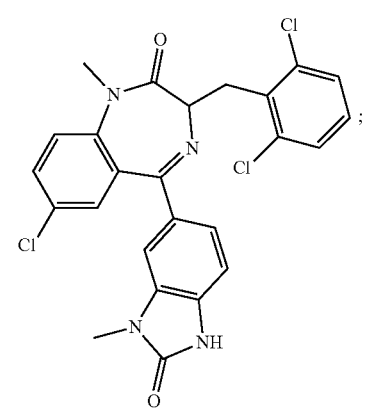
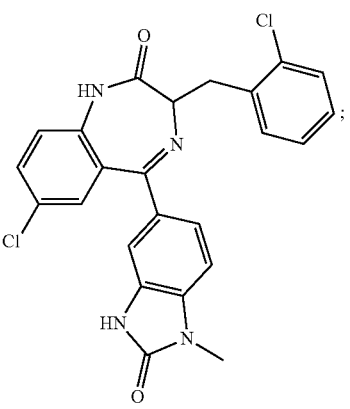

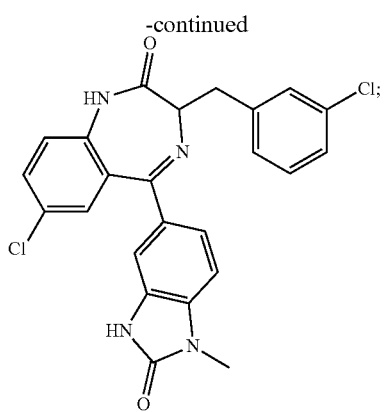
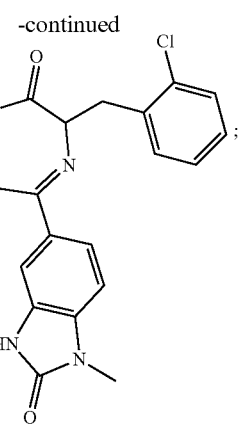
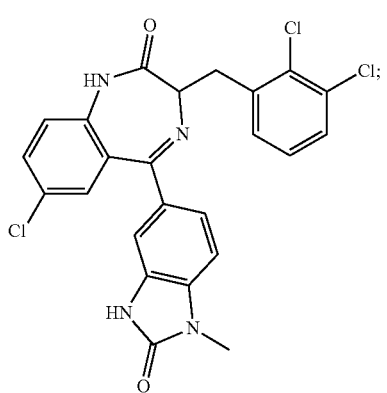
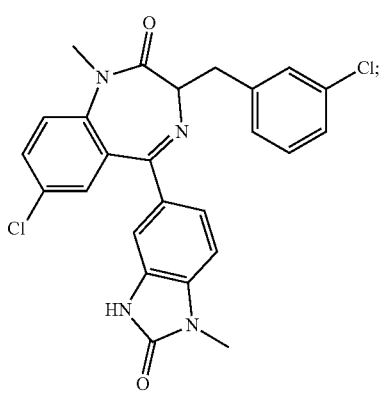
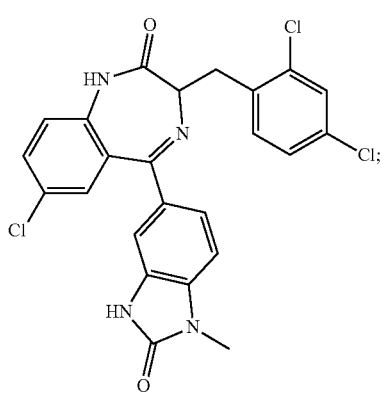
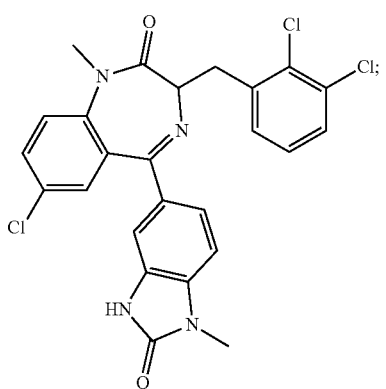
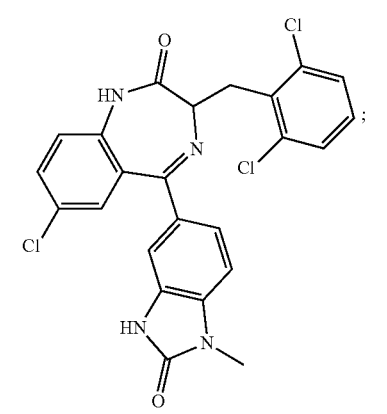
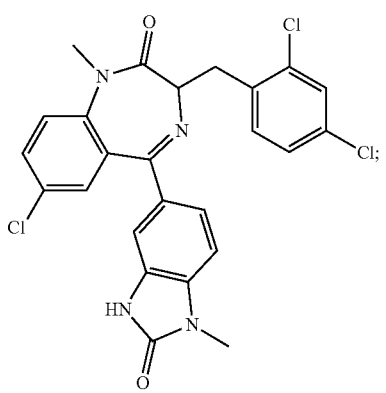

115
-continued
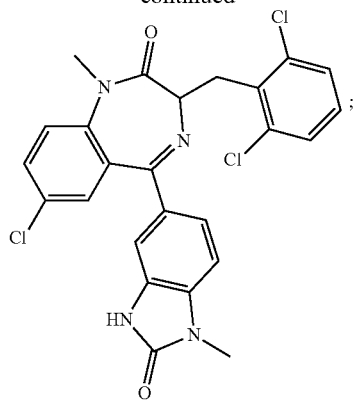
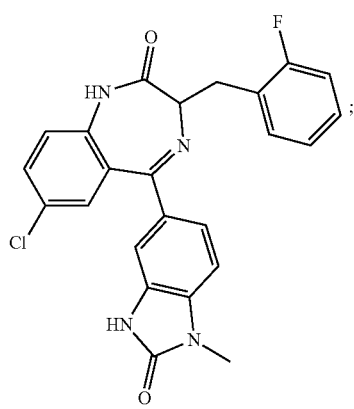
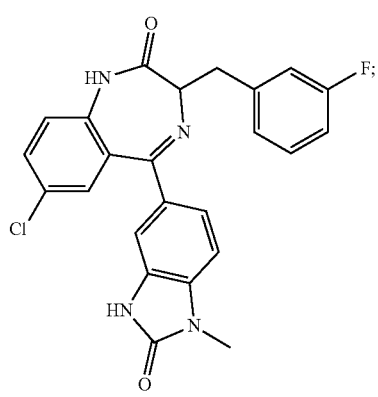
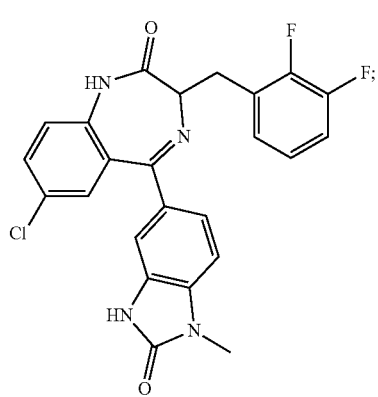
116
-continued
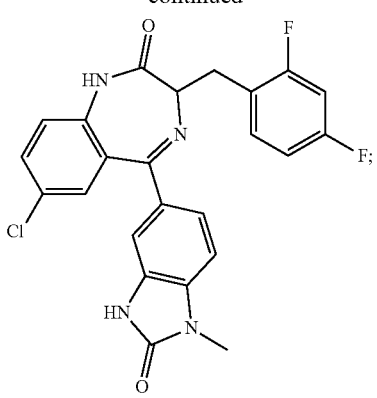
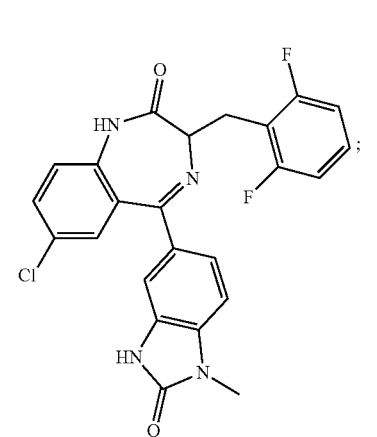
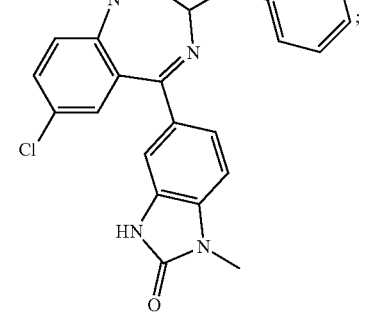
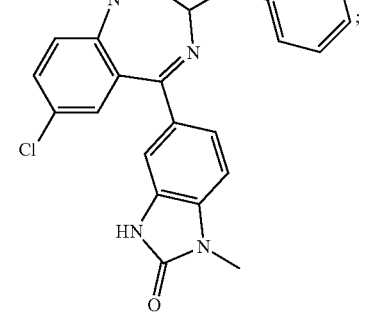

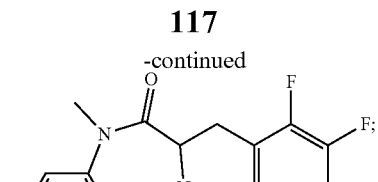
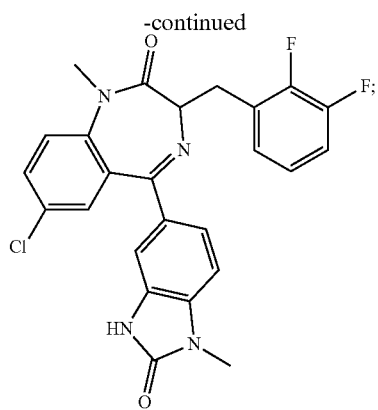
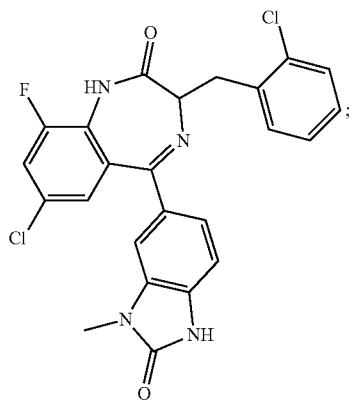
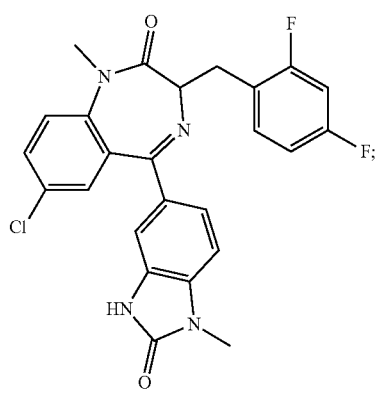
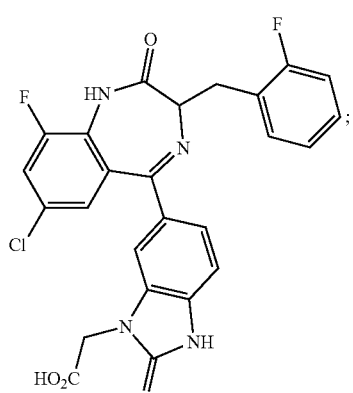
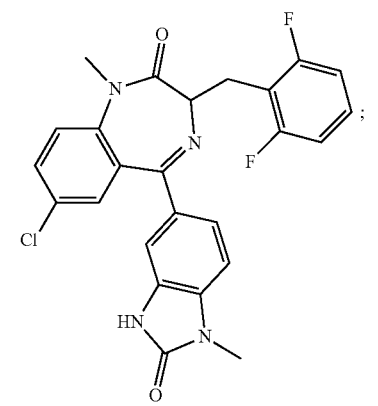
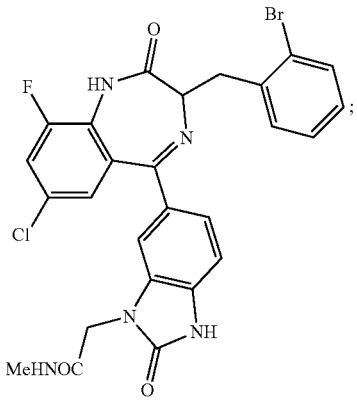
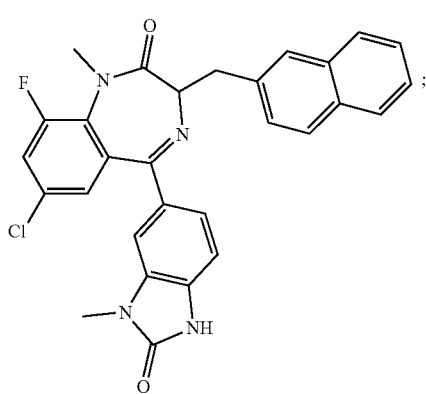
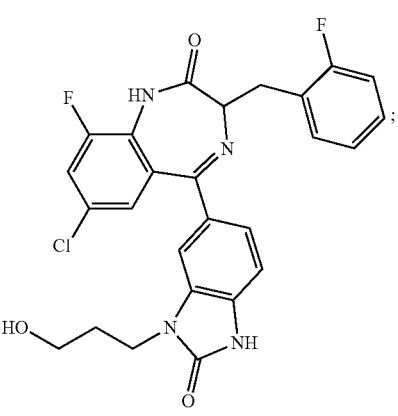

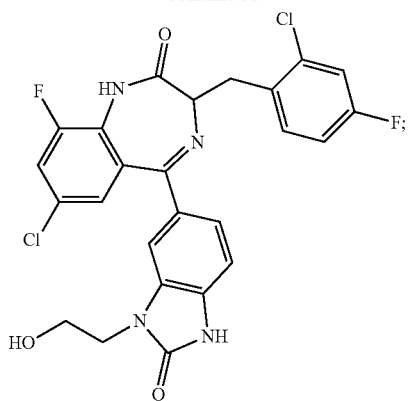
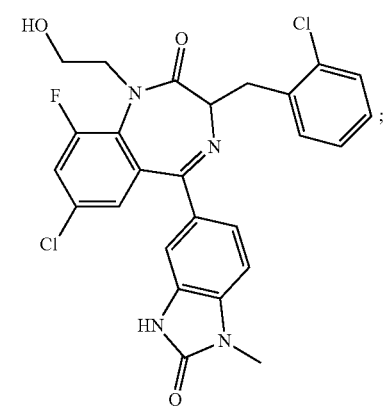
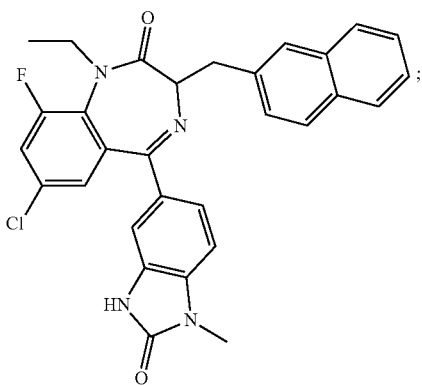
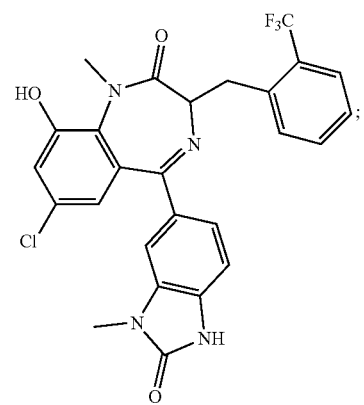
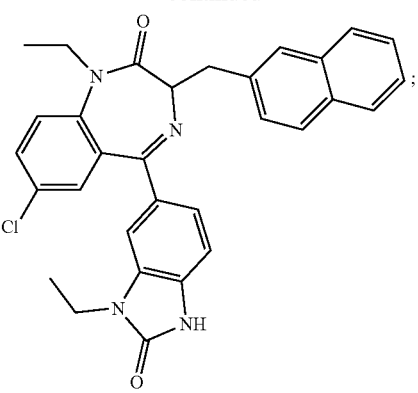
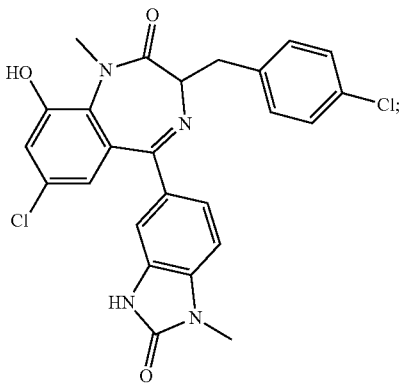
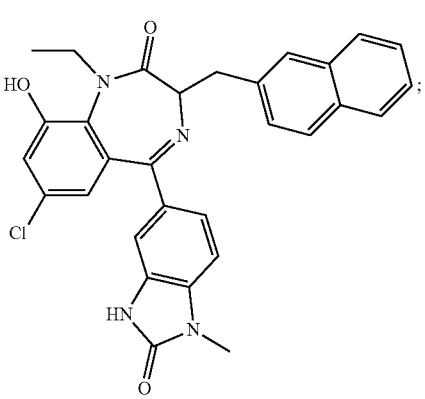
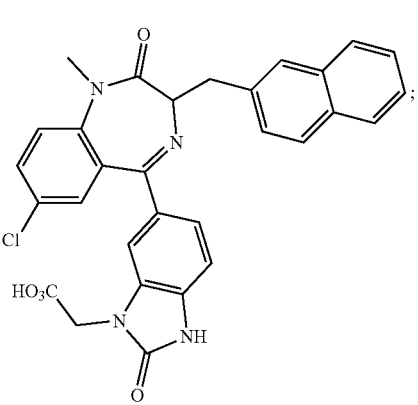

-continued
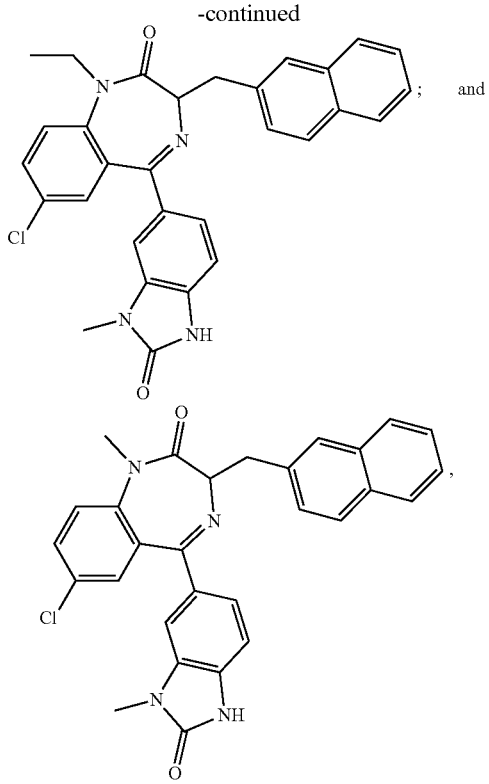
or a pharmaceutically acceptable salt thereof.
* * * * *

UNITED STATES PATENT AND TRADEMARK OFFICE
CERTIFICATE OF CORRECTION

PATENT NO. : 8,673,897 B2
APPLICATION NO. : 13/395566
DATED : May 27, 2014
INVENTOR(S) : Glick et al.

Page 1 of 2

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 106 days.

In the Claims:

Column 111, Lines 50-65, Claim 16, replace the structure:

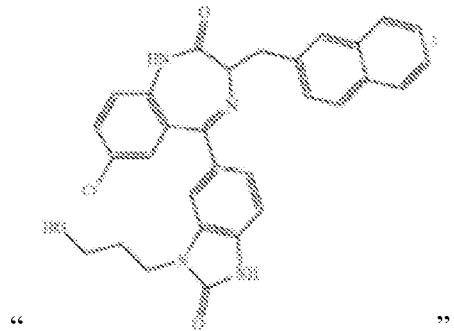

"                              "

and insert the structure

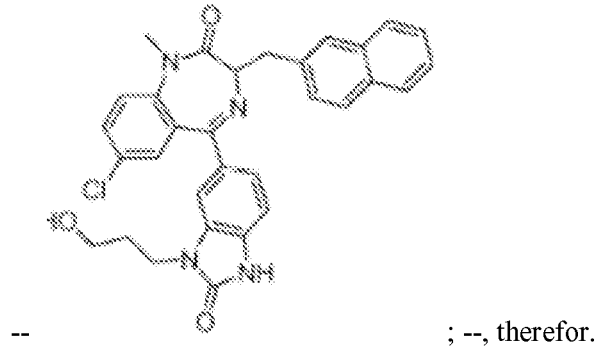

--                              ; --, therefor.

Signed and Sealed this
Twenty-third Day of February, 2016

Michelle K. Lee
*Director of the United States Patent and Trademark Office*

CERTIFICATE OF CORRECTION (continued)
U.S. Pat. No. 8,673,897 B2

Column 120, Lines 50-65, Claim 16, replace the structure:

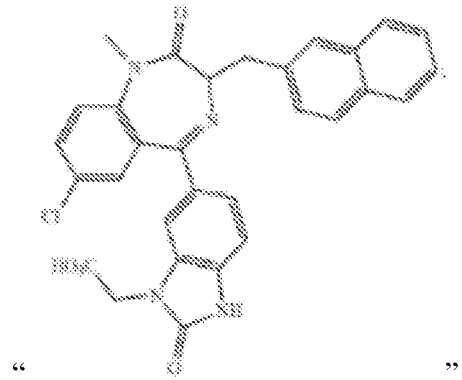

" "

and insert the structure

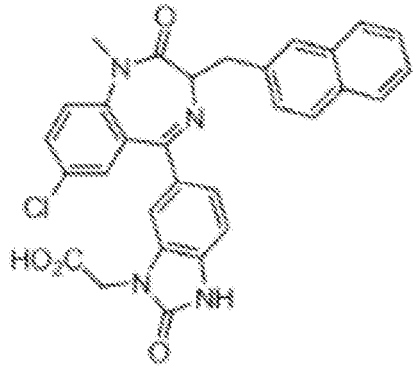

-- ; --, therefor.